US007341856B2

(12) United States Patent
Dhugga et al.

(10) Patent No.: US 7,341,856 B2
(45) Date of Patent: Mar. 11, 2008

(54) PRODUCTION OF POLYHYDROXYALKANOATE IN PLANTS

(75) Inventors: Kanwarpal S. Dhugga, Johnston, IA (US); Chun Ping Li, Johnston, IA (US); Jian G. Dong, Johnston, IA (US); William D. Hitz, Wilmington, DE (US); Matthias Liebergesell, West Des Moines, IA (US); Scott E. Nichols, Westchester, PA (US); Kristen K. Briggs, Del Mar, CA (US)

(73) Assignees: Pioneer Hi-Bred International, Inc., Johnston, IA (US); E.I. du Pont de Nemours and Company, Wilmington, DE (US)

( * ) Notice: Subject to any disclaimer, the term of this patent is extended or adjusted under 35 U.S.C. 154(b) by 23 days.

(21) Appl. No.: 11/487,811

(22) Filed: Jul. 17, 2006

(65) Prior Publication Data

US 2006/0252139 A1 Nov. 9, 2006

Related U.S. Application Data

(62) Division of application No. 10/089,281, filed as application No. PCT/US00/26963 on Sep. 29, 2000.

(60) Provisional application No. 60/156,807, filed on Sep. 29, 1999.

(51) Int. Cl.
*C12N 9/00* (2006.01)
*C07H 21/04* (2006.01)

(52) U.S. Cl. ...................................... 435/183; 536/23.2

(58) Field of Classification Search ..................... None
See application file for complete search history.

(56) References Cited

U.S. PATENT DOCUMENTS

| | | | |
|---|---|---|---|
| 5,245,023 | A | 9/1993 | Peoples et al. |
| 6,143,952 | A | 11/2000 | Srienc et al. |

FOREIGN PATENT DOCUMENTS

| | | |
|---|---|---|
| WO | WO 94/11519 | 5/1994 |
| WO | WO 98/00557 | 1/1998 |
| WO | WO 98/00557 A2 | 1/1998 |
| WO | WO 99/00505 A1 | 1/1999 |
| WO | WO 99/35278 A1 | 7/1999 |
| WO | WO 99/45122 A1 | 9/1999 |
| WO | WO 00/55328 A1 | 9/2000 |

OTHER PUBLICATIONS

Broun, P., et al., "Catalytic Plasticity of Fatty Acid Modification Enzymes Underlying Chemical Diversity of Plant Lipids," *Science*, Nov. 1998, pp. 1315-1317, vol. 282.

Fukui, T., et al., "Expression and Characterization of (*R*)-Specific Enoyl Coenzyme A Hydratase Involved in Polyhydroxyalkanoate Biosynthesis by *Aeromonas caviae," Journal of Bacteriology*, Feb. 1998, pp. 667-673, vol. 180(3), American Society for Microbiology, USA.

Hiltunen, J., et al., "Peroxisomal Multifunctional Beta-Oxidation Protein of *Saccharomyces cerevisiae," The Journal of Biological Chemistry*, Apr. 1992, pp. 6646-6653, vol. 267(10), The American Society for Biochemistry and Molecular Biology, Inc., USA.

Koski, M., et al., "A Two-domain Structure of One Subunit Explains Unique Features of Eukaryotic Hydratase 2," *The Journal of Biological Chemistry*, 2004, pp. 24666-24672, vol. 279(23).

McConnell, J., et al., "Role of *Phabulosa* and *Phavoluta* in Determining Radial Patterning in Shoots," *Nature*, Jun. 2001, pp. 709-713, vol. 411, Macmillan Magazines Ltd.

Mittendorf, V., et al., "Synthesis of Medium-Chain-Length Polyhydroxyalkanoates in *Arabidopsis thaliana* Using Intermediates of Peroxisomal Fatty Acid Beta-Oxidation," *Proc. Natl. Acad. Sci. USA*, Nov. 1998, pp. 13397-13402, vol. 95, The National Academy of Sciences, USA.

Williams, M., et al., "Production of a Polyhydroxyalkanoate Biopolymer in Insect Cells with a Modified Eucaryotic Fatty Acid Synthase," *Applied and Environmental Microbiology*, Jul. 1996, pp. 2540-2546, vol. 62(7), American Society for Microbiology, USA.

Caira, F., et al., "Differential Regulation by a Peroxisome Proliferator of the Different Multifunctional Proteins in a Guinea Pig: cDNA Cloning of the Guinea PigD-Specific Multifunctional Protein 2," *Biochem. J.*, 1998, pp. 1361-1368, vol. 330, Great Britain.

Corton, J., et al., "Rat 17 β-Hydroxysteroid Dehydrogenase Type IV is a Novel Peroxisome Proliferator-Inducible Gene," *Mol. Pharmacol.*, 1996, pp. 1157-1166, vol. 50.

Dieuaide-Noubhani, M., et al., "Further Characterization of the Peroxisomal 3-Hydroxyacyl-CoA Dehydrogenases from Rat Liver," *Eur. J. Biochem.*, 1996, pp. 660-666, vol. 240.

Filppula, S., et al., "Changing Stereochemistry for a Metabolic Pathway in Vivo," *J. Biol. Chem.*, 1995, pp. 27453-27457, vol. 270(46), The American Society for Biochemistry and Molecular Biology, Inc.

Kato, M., et al., "Production of a Novel Copolyester of 3-Hydroxybutyric Acid and Medium-Chain-Length 3-Hydroxyalkanoic Acids by *Pseudomonas* sp. 61-3 from Sugars," *Appl. Microbiol. Biotechnol.*, 1996, pp. 363-370, vol. 45.

Lee, E. et al., "Biosynthesis of Copolyesters Consisting of 3-Hydroxybutyric Acid and Medium-Chain-Length 3-Hydroxyalkanoic Acids From 1,3-Butanediol or from 3-Hydroxybutyrate by *Pseudomonas* sp. A33," *Appl. Microbiol. Biotechnol.*, 1995, pp. 901-909, vol. 42.

Liebergesell, M., et al., "Analysis of Polyhydroxyalkanoic Acid-Biosynthesis Genes of Anoxygenic Phototrophic Bacteria Reveals Synthesis of a Polyester Exhibiting an Unusual Composition," *Appl. Microbiol. Biotechnol.*, 1993, pp. 292-300, vol. 40.

(Continued)

*Primary Examiner*—Elizabeth Slobodyansky
(74) *Attorney, Agent, or Firm*—Alston & Bird LLP

(57) ABSTRACT

The invention relates to the genetic manipulation of plants to produce polyhydroxyalkanoate, particularly in the peroxisomes. Methods for producing such polymers in plants and host cells are provided. Such methods find use in producing biodegradable thermoplastics in plants and other organisms. Nucleotide molecules, expression cassettes, and genetically manipulated host cell, plants, plant tissues, and seeds are also provided.

2 Claims, 5 Drawing Sheets

OTHER PUBLICATIONS

Matsusaki, H., et al., "Cloning and Molecular Analysis of the Poly(3-hyroxybutyrate) and Poly(3-hydroxybutyrate-*co*-3-hydroxyalkanoate) Biosynthesis Genes in *Pseudomonas* sp. Strain 61-3," *J. Bacteriol.*, 1998, pp. 6459-6467, vol. 180(24).
Palosaari, P., et al., "Amino Acid Sequence Similarities of the Mitochondrial Short Chain $\Delta^3$, $\Delta^2$-Enoyl-CoA Isomerase and Peroxisomal Multifunctional $\Delta^3$, $\Delta^2$-Enoyl-CoA Isomerase, 2-Enoyl-CoA Hydratase, 3-Hydroxyacyl-CoA Dehydrogenase Enzyme in Rat Liver," *J. Biol. Chem.*, 1991, pp. 10750-10753, vol. 266(17), The American Society for Biochemistry and Molecular Biology, Inc.
Qin, Y., et al., "Peroxisomal Multifunctional Enzyme ofβ-Oxidation Metabolizing D-3-Hydroxyacyl-CoA Esters in Rat Liver: Molecular Cloning, Expression and Characterization," *Biochem. J.*, 1997, pp. 21-28, vol. 321, Great Britain.
Solaiman, D., et al., "PCR Cloning of *Pseudomonas Resinovorans* Polyhyroxyalkanoate Biosynthesis Genes and Expression *Escherichia coli," Biotechnol. Lett*, 2000, pp. 789-794, vol. 22.
Steinbüchel, A., "PHB and Other Polyhydroxyalkanoic Acids," *Polyhydroxyalkanoic Acids*, 1996, pp. 403-464, vol. 6.
Timm, A. and A. Steinbüchel, "Cloning and Molecular Analysis of the Poly(3-hydroxyalkanoic acid) Gene Locus of *Pseudomonas Aeruginosa* PAOI," *Eur. J. Biochem.*, 1992, pp. 15-30, vol. 209.
EMBL Database Report for Accession No. AI657354, May 6, 1999 (XP-002167910).
EMBL Database Report for Accession No. BE056943, Jun. 20, 2000 (XP-002167911).
GenBank Accession No. AF129396, Oct. 19, 2000.
GenBank Accession No. A49465, Mar. 7, 1997.
GenBank Accession No. AB009273, Sep. 17, 1998.
GenBank Accession No. AF042276, Jan. 5, 1999.
GenBank Accession No. AF078795, Dec. 9, 1998.
GenBank Accession No. AJ006237, Oct. 7, 1998.
GenBank Accession No. D43764, May 1, 1999.
GenBank Accession No. D88825, Aug. 19, 1997.
GenBank Accession No. E13102, Jun. 24, 1998.
GenBank Accession No. E15860, Jul. 28, 1999.
GenBank Accession No. J04987, Apr. 24, 1993.
GenBank Accession No. J05003, Apr. 26, 1993.
GenBank Accession No. L07893, Aug. 13, 1993.
GenBank Accession No. M58445, Apr. 26, 1993.
GenBank Accession No. M86456, Apr. 27, 1993.
GenBank Accession No. S83279, Mar. 12, 1997.
GenBank Accession No. U04848, Nov. 5, 1994.
GenBank Accession No. U37486, Oct. 3, 1996.
GenBank Accession No. U66242, Aug. 28, 1996.
GenBank Accession No. X65124, Apr. 18, 2005.
GenBank Accession No. X66592, Jul. 21, 1995.
GenBank Accession No. X78116, Sep. 13, 1996.
GenBank Accession No. X84260, Feb. 11, 1995.
GenBank Accession No. X94978, Apr. 18, 2005.
GenBank Accession No. Y13623, Apr. 18, 2005.
GenBank Accession No. Z28233, Apr. 18, 2005.
GenBank Accession No. Z28234, Apr. 18, 2005.
GenBank Accession No. Z28235, Mar. 18, 1998.
GenBank Accession No. Z73544, Aug. 26, 1997.

CONSTRUCT 1 (WILD TYPE yMFP):
FULL-LENGTH OF YEAST MULTIFUNCTIONAL PROTEIN

CONSTRUCT 2 (REDUCTASE):
C-TRUNCATED VERSION OF yMFP LACKING 271 AMINO ACIDS

COSTRUCT 3 (HYDRATASE):
N-TRUNCATED VERSION OF yMFP LACKING 318 AMINO ACIDS

COSTRUCT 4 (HYDRATASE):
N-TERMINALLY TRUNCATED VERSION OF yMFP LACKING 477 AMINO ACIDS

CONSTRUCT 5 (HYDRATASE):
MAIZE MFP-2

PRODUCTION OF POLYHYDROXYALKANOATE IN PLANTS

CROSS-REFERENCE TO RELATED APPLICATIONS

This application is a division of U.S. application Ser. No. 10/089,281, filed Sep. 11, 2002, now U.S. Pat. No. 7,176, 349 which is the U.S. National Stage of International Application No. PCT/US00/26963, filed Sep. 29, 2000, which claims the benefit of U.S. Provisional Application Ser. No. 60/156,807, filed Sep. 29, 1999; all of which are hereby incorporated herein by reference in their entirety.

FIELD OF THE INVENTION

The present invention relates to the genetic manipulation of plants for the production of biodegradable thermoplastics, particularly polyhydroxyalkanoate copolymers.

BACKGROUND OF THE INVENTION

Composed of polymers of a variety of organic compounds, plastics can be molded, extruded, cast into various shapes and films, and even drawn into fibers. It is such versatility that has led to incorporation of plastics into a seemingly endless number of products. Thus, plastic products have become an integral part of everyday life in industrialized society, and the demand for these products is expected to grow as the world population grows and developing countries move up the economic ladder. However, synthetic plastics are slow to degrade in landfills. If and when they do breakdown, the monomers and their derivatives resulting from degradation may actually be more hazardous to human health than the undegraded polymers (Selenskas et al. (1995) *Amer. J. Indust. Med.* 28:38R-398; Tosti et al. (1993) *Toxicol. Indust. Health* 9:493-502; Yin et al. (1996) *J. Food Drug Anal.* 4:313-318). These concerns have raised to a new level the urgency of exploring the use of the environmentally friendly, compostable polymers as substitutes for synthetic plastics. Polyhydroxyalkanoates (PHAs) are polyesters of hydroxyalkanoic acids that are synthesized by a variety of bacteria as storage polymers under stressful conditions (Steinbuchel, A. (1991) *Biomaterials: Novel materials from biological materials*, D. Byrom, ed. (New York: Macmillan Publishers Ltd.), pp. 123-213). Since PHAs have thermoplastic properties, that is they become soft when heated and hard when cooled, and are fully biodegradable, they offer an attractive alternative to synthetic plastics (Brandl et al. (1995) *Can. J. Microbiol.* 41: 143-153; Byrom, D. (1993) *Int. Biodeterior. Biodegrad.* 31:199-208; Lee, S. Y. (1996) *Biotechnol. Bioeng.* 49:1-14; Nawrath et al. (1993) *Abst. Pap. Amer. Chem. Soc.* 206:22-27; Poirier et al. (1995) *Bio/technology Nat. Publ. Co.* 13:142-150; Steinbuechel, A. (1992) *Curr. Opin. Biotechnol.* 3:291-297). Unlike man-made plastics, the production of PHA by living organisms is not dependent on finite natural resources like petroleum.

Currently, only one type of polyhydroxyalkanoate (PHA), Biopol, a copolymer made by fermentation, is commercially available (Poirier et al. (1995) *Bio/technology Nat. Publ. Co.* 13:142-150). However, at approximately $7 per pound, this polymer is much too expensive in comparison to the synthetic plastics that have similar properties but are cheaper with a price of approximately $0.5 per pound (Poirier et al. (1995) *Bio/technology Nat. Publ. Co.* 13:142-150). The higher cost of Biopol results primarily from its cost of production, the main contributing factor being the substrate (Poirier et al. (1995) *Bio/technology Nat. Publ. Co.* 13:142-150). If the PHAs can be produced in plants, the cost of production can be lowered substantially because these polymers would compete with seed oil as natural storage constituents of the cell. The current market price of plant seed oil is between 26 and 28 cents per pound (Anonymous (1998) *Economic Research Service* (Washington, D.C. 20036: U.S. Department of Agriculture). Only about 40% of the energy required to extend a fatty acid chain by two carbons is expended on extending a PHA chain by the same length. Starting with acetyl-CoA, a two carbon extension in oil biosynthesis requires two NADPH and one ATP. In comparison, only one NADPH is needed to accomplish the same for PHA biosynthesis (FIG. 1). Theoretically, more than two units of PHA should be formed for every unit of oil replaced.

Until recently, the only PHA that has been produced in plants was polyhydroxybutyrate (PHB), a homopolymer of 3-hydroxybutyric acid (John et al. (1996) *Proc. Natl. Acad Sci. USA* 93:12768-12773; Nawrath et al. (1994) *Proc. Natl. Acad. Sci. USA* 91:12760-12764; Padgette et al. (1997) *Plant Physiol.* 114 (Suppl.) 3S; Poirier et al. (1992) *Science* 256.520-523)). Because this polymer is crystalline and brittle with a melting point too close to its degradation point, PHB is difficult to mold into desirable products (Lee, S. Y. (1996) *Biotechnol. Bioeng.* 491:1-14). Many bacteria make copolymers of 3-hydroxyalkanoic acids with a carbon chain length greater than or equal to five (Steinbuchel, A. (1991) *Biomaterials: Novel materials from biological materials*, D. Byrom, ed. (New York: Macmillan Publishers Ltd.), pp. 123-213). Such copolymers are polyesters composed of different 3-hydroxyalkanoic acid monomers. Depending on the composition, these copolymers can have properties ranging from firm to elastic (Anderson et al. (1990) *Microbiol. Rev.* 54:450-472; Lee, S. Y. (1996) *Biotechnol. Bioeng* 49:1-14). Unlike PHB, the PHA copolymers are suitable for a variety of applications because they exhibit a wide range of physical properties.

Initial attempts at producing PHA in the cytosol proved toxic to the plant (Poirier et al. (1992) *Science* 256:520-523). This problem was overcome by targeting the PHA-producing enzymes to plastids (Nawrath et al. (1994) *Proc. Natl. Acad. Sci. USA* 91: 12760-12764). In either cellular compartment, however, only PHB was accumulated, not any of the copolymers. With both of these methods, the genes from *Ralstonia eutropha* (also known as *Alcaligenes eutrophus*) were used. The PHA synthase of this bacterium can utilize only short chain ($C_3$-$C_5$) monomers (Steinbuchel, A. (1991) *Biomaterials: Novel materials from biological materials*, D. Byrom, ed. (New York: Macmillan Publishers Ltd.), pp. 123-213).

Recently, the synthesis of PHA containing 3-hydroxyalkanoic acid monomers ranging from 6 to sixteen carbon in *Arabidopsis thaliana* was reported (Mittendorf et al. (1998) *Proc. Natl. Acad. Sci. USA* 95:13397-13402). To accumulate PHA, the *Arabidopsis* plants were transformed with a nucleotide sequence encoding PHA synthase from *Pseudomonas aeuginosa* that was modified for peroxisome targeting by the addition of a nucleotide sequence encoding the C-terminal 34 amino acids of a *Brassica napus* isocitrate lyase. In these plants, PHA was produced in glyoxysomes, leaf-type peroxisomes and vacuoles. However, PHA production was very low in the *Arabidopsis* plants, suggesting that either the introduced PHA synthase did not function properly in the intended organelle or more likely that the necessary substrates for the introduced PHA synthase were present at levels that were limiting for PHA synthesis. While this report demonstrated that PHA can be produced in peroxisomes of plants, the level of PHA produced in the plants was far below levels necessary for the commercial production of PHA in plants.

SUMMARY OF THE INVENTION

Methods are provided for producing PHA and intermediate molecules thereof in plants. The methods find use in the production of high-quality, biodegradable thermoplastics. The invention provides environmentally friendly alternatives to petroleum-based methods for producing plastics. The methods involve genetically manipulating a plant to produce enzymes for PHA synthesis in its peroxisomes. The methods comprise stably integrating in the genome of a plant nucleotide sequences encoding enzymes involved in the synthesis of PHA, preferably PHA copolymers.

Also provided are plants, plant tissues, plant cells, and seeds thereof, that are genetically manipulated to produce at least one enzyme involved in the synthesis of PHA in plant peroxisomes.

Nucleotide molecules and expression cassettes comprising nucleotide sequences encoding enzymes that can be employed in the synthesis of PHA in the peroxisomes of plants are provided. In particular, the invention provides nucleotide molecules encoding a maize MFP2-like polypeptide, and fragments and variants thereof. Additionally, the invention provides nucleotide molecules comprising nucleotide sequences which encode for either the hydratase or the dehydrogenase domain of the yeast multifunctional protein-2 (MFP2). Such nucleotide molecules encode novel enzymes which find use in PHA synthesis in host cells and plants, particularly in peroxisomes of plants. Isolated polypeptides encoded by the nucleotide molecules of the invention and host cells transformed with such nucleotide molecules are additionally provided.

DETAILED DESCRIPTION OF THE INVENTION

Figure 1:
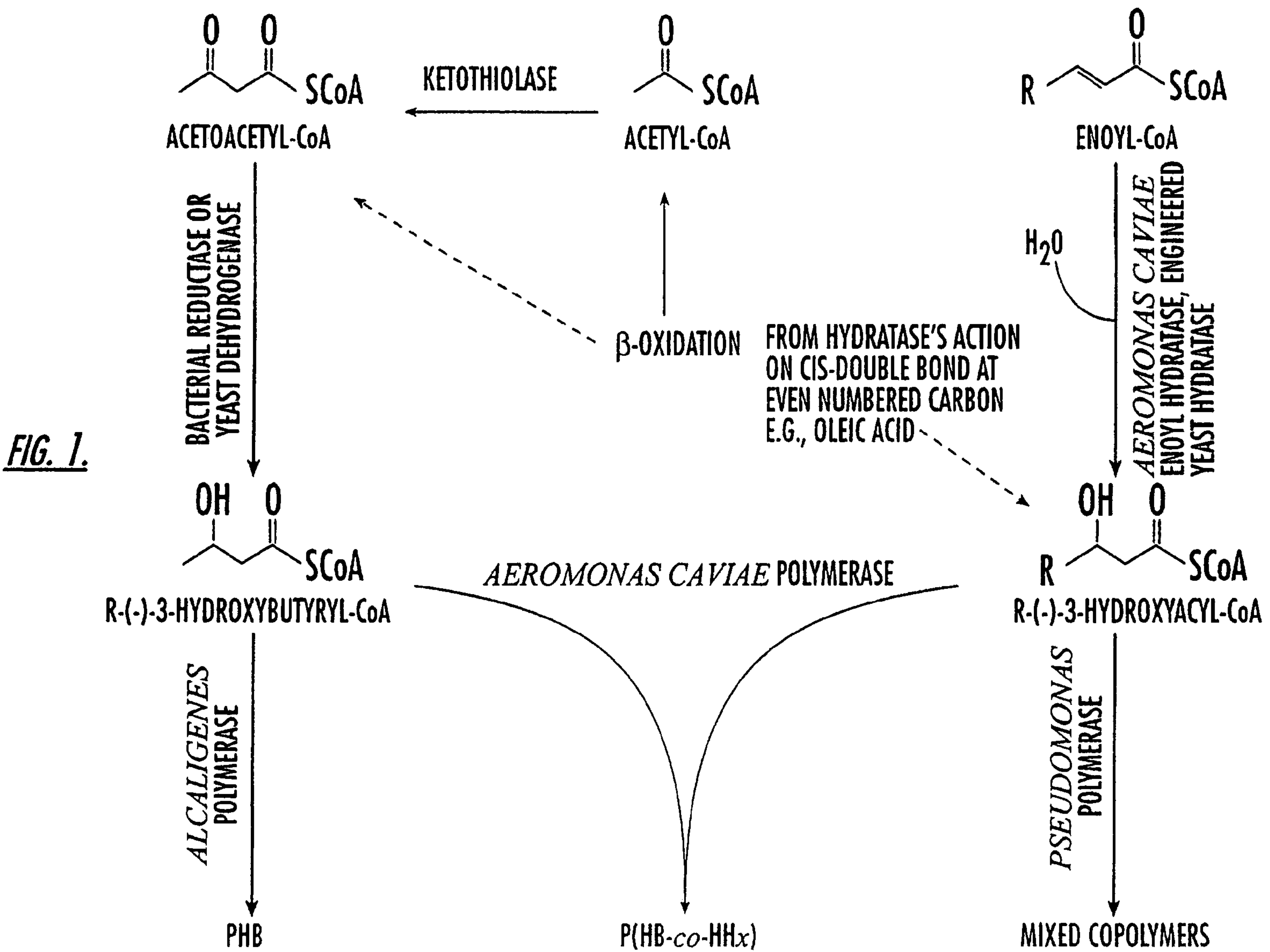
FIG. 1 schematically depicts possible biosynthetic steps for producing PHA in plant peroxisomes utilizing enzymes from bacteria.

A number of terms used herein are defined and clarified in the following section.

By "PHA copolymer" is intended a polymer composed of at least two different 3-hydroxyalkanoic acid monomers.

By "PHA homopolymer" is intended a polymer that is composed of a single 3-hydroxyalkanoic acid monomer.

By "intermediate molecule" is intended a precursor in the biosynthetic pathway for PHA in a plant. Because PHA is not known to occur naturally in a plant, the biosynthetic pathway for PHA in plant additionally encompasses enzymes and products thereof that are involved in PHA synthesis which result from the genetic manipulation of the plant. Intermediate molecules of the present invention include, but are not limited to, fatty acids and β-oxidation products derived therefrom, acetyl-CoA, acetoacetyl-CoA and other 3-ketoacyl-CoAs, 3-hydroxybutyryl-CoA, and other 3-hydroxyacyl-CoAs.

By "modified or unusual" fatty acids is intended fatty acids that have structural features such as, for example, an epoxy group, a triple bond, and methyl branching. Such "modified or unusual" fatty acids include, but are not limited to, vernolic acid, petroselinic acid, sterculic acid, chaulmoogric acid, erucic acid, ricinoleic acid, labellenic acid, crepenynic acid, and stearolic acid.

The present invention is drawn to methods and compositions for producing PHA in plants. Particularly, the present invention provides improved methods for producing PHA in plant peroxisomes. The methods involve increasing the level of PHA produced in a plant by increasing the synthesis of at least one intermediate molecule in PHA synthesis. Thus, the methods involve modifying the metabolic functions of the peroxisome to allow for increased production of PHA in a plant. Furthermore, the invention provides methods for producing PHA copolymers in plant peroxisomes.

Methods for producing PHB in the cytosol or plastids of plants and for producing PHA in plant peroxisomes are known in the art. However, such methods do not achieve the synthesis of high levels of PHA in plants. An object of the present invention is to provide improved methods for producing PHA, preferably PHA copolymers, in plants. The present invention involves genetically modifying plants in such a manner as to alter the metabolic functions of the peroxisome to increase the flux of carbon toward PHA synthesis. Such plants find use in preferred methods for producing high levels of PHA in plants, particularly in seeds, more particularly in oilseeds.

Methods for producing PHA in plants are provided. The methods involve genetically manipulating the genome of a plant to direct the synthesis of PHA to the peroxisomes, preferably peroxisomes in developing seeds. The invention encompasses plants and seeds thereof, that have been genetically manipulated to produce enzymes involved in PHA synthesis and expression cassettes containing coding sequences for such enzymes. The invention further encompasses genetically manipulated plant cells and plant tissues.

Peroxisomes, which are also known as microbodies, are small spherical organelles. In plants, there are generally two types of peroxisomes, leaf-type peroxisomes and glyoxysomes. Glyoxysomes are present in seeds containing oil, particularly during germination (Heldt (1997) *Plant Biochemistry and Plant Molecular Biology*, Oxford University Press, NY). In the present invention, "peroxisome" is intended to encompass all peroxisomes found in plant cells, including, but not limited to, leaf-type peroxisomes, microbodies, and glyoxysomes.

Methods are provided for producing PHA in a plant involving genetically manipulating the plant to produce in its peroxisomes at least two enzymes in the PHA biosynthetic pathway. The plants of the invention each comprise in their genomes at least two stably incorporated DNA constructs, each DNA construct comprising a coding sequence for an enzyme involved in PHA synthesis operably linked to a promoter that drives the expression of a gene in a plant. Plants of the invention are genetically manipulated to produce a PHA synthase (also known as a PHA polymerase) that catalyzes polymer synthesis. Preferably, such a PHA synthase catalyzes the synthesis of copolymers. More preferably such a PHA synthase catalyzes the synthesis of copolymers comprised of 3-hydroxybutanoic acid monomers and at least one additional monomer having a chain length of greater than four carbons. Most preferably such a PHA synthase catalyzes the synthesis of copolymers comprised of 3-hydroxybutanoic acid monomers and at least one additional monomer having a hydroxyacyl-chain length of from about 5 to about 18 carbons. Preferred PHA synthases include PHA synthases encoded by nucleotide sequences isolatable from *Pseudomonas oleovorans* (GenBank Accession No. M58445, SEQ ID NO: 8), *Pseudomonas putida* (GenBank Accession No. AF042276, SEQ ID NO: 9), *Pseudomonas aeruginosa* (EMBL Accession No. X66592, SEQ ID NO: 10), *Aeromonas caviae* (DDBJ Accession No. D88825, SEQ ID NO: 11), and *Thiocapsa pfennigii* (EMBL Accession No. A49465, SEQ ID NO: 12). The preferred PHA synthases additionally include the PHA synthases encoded by nucleotide sequences isolatable from *Pseudomonas fluorescens* (See U.S. Provisional Patent Application No. 60/156,770 filed Sep. 29, 1999; herein incorporated by reference.). In certain methods of the invention, the majority of PHA copolymers produced are comprised of monomers of chain-length $C_4$ to $C_{18}$.

The DNA constructs of the invention each comprise a coding sequence for an enzyme involved in PHA synthesis operably linked to a promoter that drives expression in a plant cell. Preferably, the promoters are selected from seed-preferred promoters, chemical-regulatable promoters, germination-preferred promoters, and leaf-preferred promoters. If necessary for directing the encoded proteins to the peroxisome, the DNA construct can include an operably linked peroxisome-targeting signal sequence.

It is recognized that for producing high levels of PHA copolymers in certain plants, particularly in their peroxisomes, it may be necessary to genetically manipulate plants to produce additional enzymes involved in PHA synthesis. Generally, the additional enzymes are directed to the peroxisome to increase the synthesis of at least one intermediate molecule. For example, such an intermediate molecule can be the substrate for a PHA synthase including, but not limited to, an R-(−)-3-hydroxyacyl-CoA. The methods of the invention comprise genetically modifying plants to produce, in addition to the PHA synthase described supra, one, two, three, four, or more additional enzymes involved in PHA synthesis. Preferably, each DNA construct comprising the coding sequence of one of these additional enzymes is operably linked to a promoter that drives expression in a plant and also to a nucleotide sequence encoding a peroxisome-targeting signal sequence. Depending on the plant, the addition of one or more of these enzymes may be necessary to achieve high-level PHA synthesis in the plant. The additional enzymes include, but are not limited to, an enzyme that catalyzes the synthesis of R-(−)-3-hydroxyacyl-CoA, a 3-ketoacyl-CoA reductase, and an acetyl-CoA:acetyl transferase.

Additionally, the plant of the invention can comprise in its genome a DNA construct comprising a coding sequence for second PHA synthase. Preferably, the second PHA synthase is capable of synthesizing PHB. Preferred second PHA synthases include those encoded by nucleotide sequences isolatable from *Ralstonia eutropha* (GenBank Accession No. J05003, SEQ ID NO: 13), *Acinetobacter* sp. (GenBank Accession No. U04848, SEQ ID NO: 14), *Alcaligenes latus* (GenBank Accession No. AF078795, SEQ ID NO: 15), *Azorhizobium caulinodans* (EMBL Accession No. AJ006237, SEQ ID NO: 16), *Comamonas acidovorans* (DDBJ Accession No. AB009273, SEQ ID NO: 17), *Methylobacterium extorquens* (GenBank Accession No. L07893, SEQ ID NO: 18), *Paracoccus denitrificans* (DDBJ Accession No. D43764, SEQ ID NO: 19), and *Zoogloea ramigera* (GenBank U66242, SEQ ID NO: 20)

The methods of the invention additionally comprise growing the plant under conditions favorable for PHA production, harvesting the plant, or one or more parts thereof, and isolating the PHA from the plant or part thereof. Such parts include, but are not limited to, seeds, leaves, stems, roots, fruits, and tubers. The PHA can be isolated from the plant or part thereof by methods known in the art. See, U.S. Pat. Nos. 5,942,597; 5,918,747; 5,899,339; 5,849,854; and 5,821,299; herein incorporated by reference. See also, EP 859858A1, WO 97/07229, WO 97/07230, and WO 97/15681; herein incorporated by reference.

The invention provides methods for producing increased levels of PHA in the peroxisomes of plants that involve increasing the synthesis of one or more intermediate molecules in the peroxisome. The methods involve diverting the flux of carbon in the peroxisome to favor PHA synthesis over endogenous metabolic processes such as, for example, β-oxidation. In a first aspect of the invention, plants are genetically manipulated to increase the synthesis of R-(−)-3-hydroxyacyl-CoAs. In a second aspect of the invention, plants are genetically manipulated to increase the synthesis of a specific R-(−)-3-hydroxyacyl-CoA, R-(−)-3-hydroxybutyryl-CoA. In a third aspect of the invention, the first and second aspects are combined to provide plants that are genetically manipulated to increase the synthesis of both R-(−)-3-hydroxyacyl-CoAs and R-(−)-3-hydroxybutyryl-CoA.

Further, it is recognized that each of the aspects of the invention can be used to produce PHA with substantially different monomer compositions. In particular, the level of 3-hydroxybutanoic acid in the PHA produced in a plant will vary with each aspect. For each particular type of plant, PHA produced by plants of the second or third aspect of the invention is expected to have a higher 3-hydroxybutanoic acid monomer content than PHA produced by plants of the first aspect. Similarly, PHA produced by plants of the second aspect is expected to have a higher 3-hydroxybutanoic acid monomer content than PHA produced by plants of the third aspect.

In a first embodiment of the invention, methods are provided for producing PHA involving genetically manipulating a plant for increased synthesis of R-(−)-3-hydroxyacyl-CoA, a key intermediate molecule in PHA synthesis in the peroxisome. The methods comprise stably integrating into the genome of a plant a first DNA construct comprising a coding sequence for a PHA synthase, and a second DNA construct comprising a coding sequence for an enzyme that catalyzes the formation R-(−)-3-hydroxyacyl-CoA, a substrate of PHA synthase. In β-oxidation in plant peroxisomes, acyl-CoA oxidase catalyzes the conversion of fatty acyl-CoA into 2-enoyl-CoA which is subsequently converted to S-(+)-3-hydroxyacyl-CoA via the 2-enoyl-CoA hydratase of a multifunctional protein. While some R-(−)-3-hydroxyacyl-CoA may be present in peroxisomes, the level is believed to be very low and insufficient to allow for the synthesis of an economically acceptable level of PHA in a plant. Furthermore, all known PHA synthases require that 3-hydroxyacyl- CoA monomers be in R-(−)-form for PHA synthesis. To overcome the substrate limitation for PHA synthesis, the present invention discloses methods for PHA synthesis which involve providing a plant with an enzyme in its peroxisomes that catalyzes the formation of R(−)-3-hydroxyacyl-CoA. By genetically manipulating a plant to increase the synthesis of R-(−)-3-hydroxyacyl-CoA, the present invention overcomes a major impediment to achieving high-level production in plants of PHA, particularly copolymers. Such an enzyme can be an enoyl-CoA hydratase that catalyzes the synthesis of R-(−)-3-hydroxyacyl-CoA, particularly an 2-enoyl-CoA hydratase from *Aeromonas caviae* (DDBJ Accession No. E15860, SEQ ID NO: 21).

Alternatively, two proteins from yeast and one from maize can each be utilized as the enzyme. One such protein is the yeast multifunctional protein (encoded by GenBank Accession No. M86456, SEQ ID NO: 3) which possesses an 2-enoyl-CoA hydratase activity and a 3-hydroxyacyl dehydrogenase (reductase) activity. Similarly, the invention provides an isolated MFP2-like polypeptide (previously designated as a multifunctional protein-2 or MFP-2) from maize (SEQ ID NO: 2) which also possesses an 2-enoyl-CoA hydratase activity. The invention further provides isolated nucleotide molecules encoding such a maize MFP2-like polypeptide (SEQ ID NO: 1). The hydratase of the yeast multifunctional protein and maize MFP2-like polypeptide is known to yield R-(−)-3-hydroxyacyl-CoA products. If necessary, the dehydrogenase activity of the yeast multifunctional protein can be eliminated or neutralized by methods known to those of ordinary skill in the art such as, for example, site-directed mutagenesis, and truncation of the coding sequence to only the portion necessary to encode the desired hydratase activity. The invention provides isolated nucleotide molecules comprising nucleotide sequences which encode either the hydratase or reductase of the yeast multifunctional protein (SEQ ID NOs: 4 and 6). Additionally provided are isolated polypeptides encoded by such sequences (SEQ ID NOs: 5 and 7).

Other multifunctional proteins known in the art can be utilized in the methods of the present invention. Any multifunctional protein possessing a domain comprising a 2-enoyl-CoA hydratase that is capable of catalyzing the synthesis of R-(−)-3-hydroxyacyl-CoA can be employed in the methods of the invention.

The other yeast protein that can be utilized as the enzyme that catalyzes the formation of R-(−)-3-hydroxyacyl-CoA is an enzyme identified as a 3-hydroxybutyryl-CoA dehydrogenase (Leaf et al. (1996) *Microbiology* 142:1169-1180). The gene encoding this enzyme can be cloned from *Saccharomyces cervisae*, sequenced and employed in the methods of the present invention. It is recognized that the nucleotide sequence encoding this enzyme can be modified to alter the amino acid sequence of the enzyme in such a manner as to favorably affect the production of R-(−)-3-hydroxyacyl-CoA in a plant. Such modifications can affect characteristics of the enzyme such as, for example, substrate specificity, product specificity, product inhibition, substrate binding affinity, product binding affinity, and the like. A method such as, for example, DNA shuffling can be employed to modify this enzyme in the desired manner. Any method known in the art for altering the characteristics of an enzyme to favorably affect the mass action ratio toward the desired product is encompassed by the methods of the present invention. Such methods typically involve modifying at least a portion of the nucleotide sequence encoding the enzyme and include, but are not limited to, DNA shuffling, site-directed mutagenesis, and random mutagenesis.

In a second embodiment of the invention, methods are provided for producing PHA involving genetically manipulating a plant for increased synthesis of R-(−)-3-hydroxybutyryl-CoA, a substrate of PHA synthase, in peroxisomes. The methods of the invention provide a plant that is genetically manipulated for increased synthesis of a substrate for a PHA synthase and thus provide a plant that is genetically manipulated for high-level PHA synthesis in its peroxisomes. The methods involve stably integrating into the genome of a plant a first DNA construct comprising a coding sequence for a PHA synthase, and a second DNA construct comprising a coding sequence for 3-ketoacyl-CoA reductase and a third DNA construct comprising a coding sequence for an acetyl-CoA:acetyl transferase. The first, second, and third DNA constructs each additionally comprise an operably linked promoter that drives expression in a plant cell, and if necessary, an operably linked peroxisome-targeting signal sequence. Acetyl-CoA:acetyl transferase, also referred to as ketothiolase, catalyzes the synthesis of acetoacetyl-CoA from two molecules of acetyl-CoA. Acetoacetyl-CoA can then be converted into R-(−)-3-hydroxybutyryl-CoA via a reaction catalyzed by a 3-ketoacyl-CoA reductase, particularly an acetoacetyl-CoA reductase.

Preferred 3-ketoacyl-CoA reductases of the invention are those that utilize NADH and include, but are not limited to, at least a portion of the multifunctional proteins from yeast (encoded by GenBank Accession No. M86456, SEQ ID NO: 3) and rat (encoded by GenBank Accession No. U37486, SEQ ID NO: 22), wherein such a portion comprises a 3-ketoacyl-CoA reductase domain. Any multifunctional protein having a 3-ketoacyl-CoA reductase (dehydrogenase) domain can be employed in the methods of the invention. However, in the methods of the invention, NADPH-dependent 3-ketoacyl-CoA reductases can also be employed including, but not limited to, the 3-ketoacyl-CoA reductases encoded by GenBank Accession No. J04987 (SEQ ID NO: 23).

Preferred acetyl-CoA:acetyl transferases of the invention include a radish acetyl-CoA:acetyl transferase encoded by the nucleotide sequence having EMBL Accession No. X78116 (SEQ ID NO: 24).

If necessary to increase the level of NADPH in the peroxisome, the methods of the second embodiment can additionally involve, stably integrating into the genome of a plant a fourth DNA construct comprising a nucleotide sequence encoding an NADH kinase or an $NAD^+$ kinase and an operably linked promoter that drives expression in a plant cell. Such NADH and $NAD^+$ kinases catalyze the synthesis of NADPH and $NADP^+$, respectively. Nucleotide sequences encoding such kinases include, but are not limited to, DDJB Accession No. E13102 (SEQ ID NO: 25) and EMBL Accession Nos. Z73544 (SEQ ID NO: 26) and X84260 (SEQ ID NO: 27). The fourth construct can additionally comprise an operably linked peroxisome-targeting signal sequence. By targeting such NADH and $NAD^+$ kinases to the peroxisome, the level of NADPH and $NADP^+$ can be increased in the plant peroxisome for use by enzymes, such as, for example, an NADPH-dependent 3-ketoacyl-CoA reductase.

In a third embodiment of the invention, methods are provided for producing PHA in a plant involving genetically manipulating a plant for increased synthesis of R-(−)-3-hydroxybutyryl-CoA and other R-(−)-3-hydroxyacyl-CoA molecules. Such methods provide a plant that is genetically manipulated to overcome substrate limitations for PHA copolymer synthesis in its peroxisomes. The methods involve stably integrating into the genome of a plant a first, a second, a third, and a fourth DNA construct comprising a coding sequence for an enzyme involved in PHA synthesis in a plant. The first DNA construct comprises a coding sequence for a PHA synthase that is capable of catalyzing the synthesis of PHA copolymers. The second DNA construct comprises a coding sequence for an enzyme that catalyzes the synthesis of R-(–)-3-hydroxyacyl-CoA. The third DNA construct comprises a coding sequence for a 3-ketoacyl-CoA reductase, and the fourth DNA construct comprises a coding sequence for an acetyl-CoA:acetyl transferase. If desired, a fifth DNA construct can also be stably integrated into the genome of the plant. The fifth DNA construct comprises a nucleotide sequence encoding a NADH kinase or an $NAD^+$ kinase.

Preferred enzymes of the third embodiment include the enzymes of the first and second embodiments, described supra. The DNA constructs each additionally comprise an operably linked promoter and, if necessary, an operably linked peroxisome-targeting signal to direct the encoded protein to the peroxisome. By targeting such enzymes to the peroxisome, the plant is capable of increased synthesis of intermediate molecules, particularly intermediate molecules that are substrates for a PHA synthase that catalyzes the formation of copolymers.

Methods are provided for increasing the synthesis of PHA in a plant. Such methods find use with methods known in the art for producing PHA in plants, particularly in peroxisomes. The methods of the invention involve increasing the synthesis of an intermediate molecule in PHA synthesis. Preferably, such an intermediate molecule is limiting for PHA synthesis in the peroxisome and that increasing the synthesis of such a molecule in the peroxisome increases the level of PHA produced in a plant. It is recognized that increasing the synthesis of an intermediate molecule in a plant peroxisome might not lead to an increased level of the intermediate molecule in the plant because the intermediate molecule can be further metabolized into, for example, PHA.

The methods for increasing the synthesis of PHA in a plant involve stably incorporating into the genome of a plant at least one DNA construct comprising a coding sequence for an enzyme involved in the synthesis of an intermediate molecule, operably linked to a promoter that drives expression in a plant. If necessary for peroxisome-targeting of the encoded enzyme, the DNA construct additionally comprises a peroxisome-targeting signal operably linked to the coding sequence.

The methods of the invention can be used to increase the synthesis of any intermediate molecule in PHA synthesis. Preferred intermediate molecules include those that can be limiting for PHA synthesis, particularly in the peroxisome, such as, for example, R-(–)-3-hydroxybutyryl-CoA, other R-(–)-3-hydroxyacyl-CoAs, acetoacetyl-CoA, and other 3-ketoacyl-CoAs.

A plant can be genetically manipulated to produce any one or more of the enzymes involved in the synthesis of the intermediate molecule in the plant including, but not limited to, the enzymes for PHA synthesis of the present invention described supra. Preferred enzymes for increasing the synthesis of an intermediate molecule include enzymes, described supra, that catalyze the formation of R-(–)-3-hydroxyacyl-CoA, 3-ketoacyl-CoA reductases that utilize NADH and acetyl-CoA:acetyl transferases.

In a fourth embodiment of the invention, methods are provided for increasing in a plant the synthesis of a R-(–)-3-hydroxyacyl-CoA, key intermediate molecule in PHA synthesis. The level in the peroxisome of R-(–)-3-hydroxyacyl-CoA, a substrate of PHA synthase, is known to be very low and is believed to limit the level of PHA produced in the peroxisome. Thus, increasing the synthesis of R-(–)-3-hydroxyacyl-CoA can increase the synthesis of PHA in a plant. The methods comprise genetically manipulating plants to produce an enzyme that catalyzes the synthesis of R-(–)-3-hydroxyacyl-CoA, preferably an enzyme selected from a 2-enoyl-CoA hydratase from *Aeromonas caviae* (encoded by DDBJ Accession No. E15860, SEQ ID NO: 21), a maize MFP2-like polypeptide (SEQ ID NO: 2), a modified yeast multifunctional protein (SEQ ID NO: 5) possessing a 2-enoyl-CoA hydratase activity and a 3-hydroxyacyl-CoA dehydrogenase activity wherein the latter activity is neutralized, or a modified yeast 3-hydroxyacyl-CoA dehydrogenase, wherein the enzyme utilizes NADH and its mass action ratio has been shifted in favor of R-(–)-3-hydroxyacyl-CoA over 3-ketoacyl-CoA.

Methods are provided for producing novel enzymes for the synthesis of PHA, particularly in peroxisomes, more particularly in plant peroxisomes. The methods find use in providing novel peroxisome-localized enzymes for PHA synthesis in plant peroxisomes. Additionally, the methods find further use in providing DNA constructs that can be used to transform a plant for the production of a PHA synthesis enzyme in its peroxisomes. The methods involve modifying the coding sequence of a multifunctional protein, particularly an MFP2, more particularly an MFP2 from yeast (encoded by GenBank Accession No. M86456, SEQ ID NO: 3) or rat (encoded by GenBank Accession No. U37486, SEQ ID NO: 22). The coding sequence is modified to eliminate or substantially reduce of one of the two separate enzymatic activities of the protein encoded thereby. The coding sequence can be modified by methods known in the art including, but not limited, to site-directed mutagenesis and deletion of a portion of the coding sequence. If necessary, an initiation codon, a stop codon or both can be added to facilitate translation in a host cell. The methods can further involve preparing a DNA construct by operably linking a nucleotide sequence encoding a peroxisome-targeting signal to the modified coding sequence. If desired for expression in a plant or host cell, the DNA construct can additionally comprise an operably linked promoter that drives expression in the plant or cell. The novel enzymes of the invention can be produced by transforming a plant or host cell with such a DNA construct.

Figure 2:
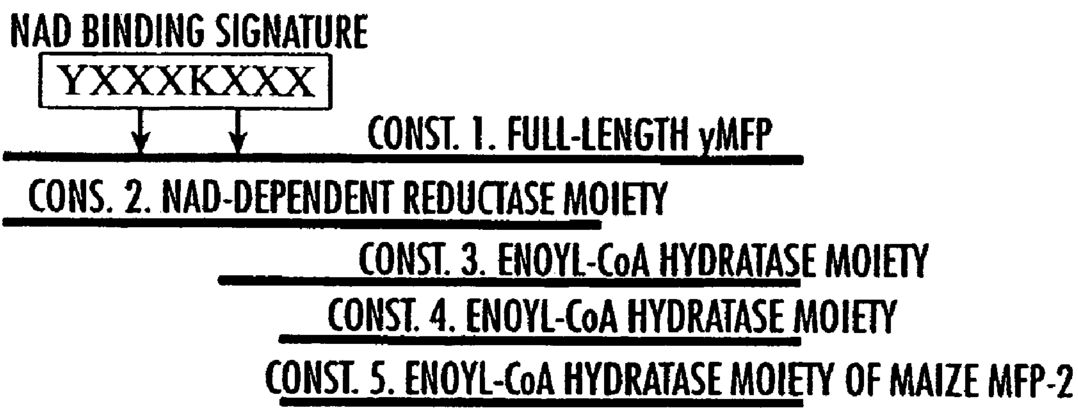
FIG. 2 schematically illustrates the full-length yeast multifunctional protein (yMFP), truncated versions of yMFP, and the maize MFP2-like polypeptide.

In a fifth embodiment of the invention, methods are provided for producing a peroxisome-targeted 2-enoyl-CoA hydratase employing the coding sequence of a yeast MFP2 (GenBank Accession No. M86456, SEQ ID NO: 3). The methods involve modifying the coding sequence to eliminate the dehydrogenase (also referred to as reductase) activity of the encoded protein. This can be accomplished by, for example, deleting from the 5' end of the coding sequence a portion that encoded at least part of the dehydrogenase domain (FIG. 2, SEQ ID NO: 4). To facilitate translation of the encoded protein, an initiation codon can be added to the truncated nucleotide sequence (SEQ ID NO: 4). A DNA construct can be prepared by operably linking a nucleotide sequence encoding a plant peroxisome-targeting signal to such a truncated coding sequence. Such a DNA construct can additionally comprise an operably linked promoter that drives expression in a plant.

In a sixth embodiment of the invention, methods are provided for producing a NADH-dependent, peroxisome-targeted 3-ketoacyl-CoA reductase employing the coding sequence of a yeast multifunctional protein (GenBank Accession No. M86456, SEQ ID NO: 3). The methods involve modifying the coding sequence of a multifunctional protein to eliminate the hydratase activity of the encoded protein. Because the reductase of the yeast multifunctional protein is known to be NADH dependent, a peroxisome-targeted 3-ketoacyl-CoA reductase is expected to be NADH dependent. Such an NADH-dependent reductase finds use in the high-level synthesis of PHA in plant peroxisomes where NADPH, but not NADH, is known to be limiting. This can be accomplished by, for example, deleting from the 3' end of the coding sequence a portion that encoded at least a part of the hydratase domain (FIG. 2, SEQ ID NO: 6). To facilitate translation of the desired polypeptide, an appropriate stop codon can be operably linked to the 3' end of the truncated coding sequence (SEQ ID NO: 6). In addition, a DNA construct can be prepared by operably linking a nucleotide sequence encoding a plant peroxisome-targeting signal to such a truncated coding sequence. Such a DNA construct can additionally comprise an operably linked promoter that drives expression in a plant.

Methods are provided for increasing the level in a plant of at least one intermediate molecule in PHA synthesis in the plant. Such intermediate molecules include molecules naturally synthesized by the plant as well as those that are synthesized by the plant after being genetically manipulated to comprise at least one enzyme involved in PHA synthesis that does not occur naturally in the plant. The methods involve the buildup of intermediate molecules as well as the use of additional enzymes for the production of specialty chemicals. Thus, plants containing intermediate molecules or PHA can be obtained. It is recognized that methods of the present invention can be used in combination with methods for producing PHA homopolymers, copolymers or both.

To increase the level of at least one intermediate molecule in a plant, the plant can be genetically manipulated to produce any one or more of the enzymes involved in the synthesis of the intermediate molecule in the plant including, but not limited to, the enzymes for PHA synthesis of the present invention described supra. Preferred enzymes for increasing the synthesis of an intermediate molecule include enzymes, described supra, that catalyze the formation of R-(−)-3-hydroxyacyl-CoA, 3-ketoacyl-CoA reductases that utilize NADH and acetyl-CoA:acetyl transferases.

Further, it is recognized that it may be necessary to lower or eliminate the activity of an endogenous enzyme in a plant that in some way limits the synthesis of the desired intermediate molecule. Such an endogenous enzyme may, for example, catabolize or modify the intermediate molecule in an undesirable way. Methods for lowering or eliminating the activity of an enzyme in a plant include, but are not limited to, sense and antisense suppression methods. For example, the activity of the 2-enoyl-CoA hydratase of an endogenous multifunctional protein that catalyzes the formation of S-(+)-3-hydroxyacyl-CoA can be reduced or eliminated in the peroxisome to favor, instead, the synthesis of R-(−)-3-hydroxyacyl-CoA therein.

While the methods of the invention can be used with any plant, preferred plants are oilseed plants genetically manipulated to produce PHA copolymers in their peroxisomes, particularly in seeds. More preferably, the oilseed plants have been genetically manipulated to have seeds with increased levels of short-chain fatty acids, modified or unusual fatty acids, cytosolic acyl-CoA oxidase activity, or combinations thereof. Such oilseed plants have increased rates of β-oxidation in their seeds and find use in methods of producing high levels of PHA copolymers, particularly in seeds.

While the compositions and methods disclosed herein are drawn to the production of PHA and PHA intermediates in plants, the present invention is not limited to methods involving PHA production in plant and cells thereof. Those skilled in the art will recognize that the compositions and methods can be employed with any host cell for the production of PHA and intermediates thereof. Host cells include, but are not limited to, plant cells, animal cells, bacterial cells and fungal cells, particularly yeast cells.

Compositions comprising nucleic acid molecules which comprise coding sequences for enzymes involved in the synthesis of PHA in the peroxisomes of plants are provided. Compositions of the invention include nucleotide molecules encoding a maize MFP2-like polypeptide and fragments and variants thereof. In particular, the present invention provides for isolated nucleic acid molecules comprising nucleotide sequences encoding the amino acid sequence set forth in SEQ ID NO: 2. Further provided are polypeptides having an amino acid sequence encoded by a nucleic acid molecule described herein, for example that set forth in SEQ ID NO: 1, and fragments and variants thereof.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein of the invention. Alternatively, fragments of a nucleotide sequence that are useful as hybridization probes generally do not retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a nucleotide sequence of the invention that encodes a biologically active portion of a multifunctional protein will encode at least 15, 25, 30, 50, 100, 150, 200, 250 or 300 contiguous amino acids, or up to the total number of amino acids present in a full-length multifunctional protein of the invention (for example, 314 amino acids for SEQ ID NO: 2). Fragments of a multifunctional protein nucleotide sequence that are useful as hybridization probes for PCR primers generally need not encode a biologically active portion of a multifunctional protein.

Thus, a fragment of a multifunctional protein nucleotide sequence may encode a biologically active portion of a multifunctional protein, or it may be a fragment that can be used as a hybridization probe or PCR primer using methods disclosed below. A biologically active portion of a multifunctional protein can be prepared by isolating a portion of one of the multifunctional protein nucleotide sequences of the invention, expressing the encoded portion of the multifunctional protein (e.g., by recombinant expression in vitro), and assessing the activity of the encoded portion of the multifunctional protein. Nucleic acid molecules that are fragments of a multifunctional protein nucleotide sequence comprise at least 16, 20, 50, 75, 100, 150, 200, 250, 300, 350, 400, 450, 500, 550, 600, 650, 700, 800, 900, 1,000, 1,100, 1,200 or 1,300 nucleotides, or up to the number of nucleotides present in a full-length multifunctional protein nucleotide sequence disclosed herein (for example, 1362 nucleotides for SEQ ID NO: 1).

By “variants” is intended substantially similar sequences. For nucleotide sequences, conservative variants include those sequences that, because of the degeneracy of the genetic code, encode the amino acid sequence of one of the multifunctional proteins or other enzymes involved in PHA synthesis of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a multifunctional protein or other enzyme of the invention. Generally, variants of a particular nucleotide sequence of the invention will have at least about 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequence set forth herein. Sequences isolated based on their sequence identity to the entire maize MFP2-like polypeptide nucleotide sequence set forth herein or to fragments thereof are encompassed by the present invention. Such sequences include sequences that are orthologs of the disclosed sequences. By “orthologs” is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the maize MFP2-like polypeptide nucleotide sequence of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, New York).

For example, the entire maize MFP2-like polypeptide nucleotide sequence disclosed herein, or one or more portions thereof, may be used as a probe capable of specifically hybridizing to corresponding MFP2 sequences and messenger RNAs. To achieve specific hybridization under a variety of conditions, such probes include sequences that are unique among MFP2 sequences and are preferably at least about 10 nucleotides in length, and most preferably at least about 20 nucleotides in length. Such probes may be used to amplify corresponding MFP2 sequences from a chosen organism by PCR. This technique may be used to isolate additional coding sequences from a desired organism or as a diagnostic assay to determine the presence of coding sequences in a organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By “stringent conditions” or “stringent hybridization conditions” is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for an MFP2 and which hybridize under stringent conditions to the MFP2 sequence disclosed herein, or to fragments thereof, are encompassed by the present invention. Such sequences will be at least about 50% to 60% homologous, about 60%, to 70% homologous, and even at least about 75%, 80%, 85%, 90%, 91%, 92%, 93%, 94%, 95%, 96%, 97%, 98%, 99% or more homologous with the disclosed sequences. That is, the sequence identity of sequences may range, sharing at least about 50% to 60%, about 65% or 70%, and even at least about 75%, 80%, 85%, 90%, 91%, 92%, 93%, 94%, 95%, 96%, 97%, 98%, 99% or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res*. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol*. 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "DNA constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the DNA constructs of the present invention encompass all nucleotide constructs that can be employed in the methods of the present invention including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

In the practice of embodiments of the invention, heterologous DNA can be employed. By "heterologous DNA" is intended DNA that is foreign to the genome of an organism. Such foreign DNA encompasses any DNA present in the genome of an organism that originated in the present organism or one of its progenitors by artificial methods such as, for example, transformation. Such foreign DNA also encompasses DNA native to an organism introduced into the genome of the organism via non-natural methods such as, for example, transformation. Related terms include "heterologous protein" and "heterologous enzyme" which are encoded by "heterologous DNA." It is recognized that such a heterologous enzyme or protein can possess an amino acid sequence that is identical to that of a native enzyme or protein of an organism. Further, a "heterologous coding sequence" is coding sequence composed of heterologous DNA.

It is recognized that enzymes similar to those described herein, referred to as "variant enzymes," may be utilized. By "variant enzyme" or "variant protein" is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess at least one desired biological activity of the native protein, that is, for example, 2-enoyl-CoA hydratase or 3-ketoacyl-CoA reductase activity as described herein for MFP2. Such variants may result from, for example, genetic polymorphism or from human manipulation. Biologically active variants of a native enzyme or protein of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the polypeptide can be prepared by mutations in the nucleotide sequence encoding the native protein of interest which is also referred to as the coding sequence of the native protein. Thus, proteins and their respective coding sequences include the native forms as well as variants thereof.

A variety of methods can be used to produce variant enzymes such as, for example, mutagenesis of the coding sequences of the native enzyme. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

In constructing variants of the enzyme of interest, modifications to the nucleotide sequences encoding the variants will be made such that variants continue to possess the desired activity. Obviously, any mutations made in the DNA encoding the variant protein must not place the sequence out of reading frame and preferably will not create complementary regions that could produce secondary mRNA structure. See EP Patent Application Publication No. 75,444.

In some cases it may be necessary to utilize a protein that possesses more than one enzymatic function. If only one or subset of enzymatic activities of such a protein is desired, it will be necessary to "neutralize," that is eliminate or substantially minimize, the undesirable enzymatic activity or activities. Those skilled in the art of modifying proteins and enzymes know that a variety of methods can be used singly or in combination to neutralize an enzymatic activity. Generally such methods involve modifying the coding sequences of the protein such that the desired activity or activities are retained and the undesirable activity or activities are eliminated. Such modifications to the coding sequence include deletions, substitutions, and insertions.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by enzyme activity assays, such as, for example, a PHA synthase assay, an enoyl-CoA hydratase assay, a ketoacyl-CoA reductase assay and an acetyl-CoA: acetyl transferase assay. See, for example, Schubert et al. (1988) *J. Bacteriol*. 170:5837-5847 (PHA synthase), Valentin and Steinbuechel (1994) *Appl. Microbiol. Biotechnol*. 40:699-709 (PHA synthase), Moskowitz and Merrick (1969) *Biochemistry* 8:2748-2755 (enoyl-CoA hydratase), Lynen and Wieland (1955) *Meth. Enzymol*. 1:566-573 (ketoacyl-CoA reductase), Nishimura et al. (1978) *Arch Microbiol*. 116:21-27 (acetyl-CoA:acetyl transferase) and Iwahashi et al. (1989) *J. Biochem*. 105:588-593 (NAD/NADH kinase); all of which are herein incorporated by reference.

Nucleotide sequence encoding the enzymes of the invention may be derived from a mutagenic and recombinogenic procedure such as DNA shuffling. With such a procedure, one or more different coding sequences of an enzyme of the invention can be manipulated to create a new enzyme possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, nucleotide sequence motifs encoding a domain of interest in an enzyme of the invention may be shuffled to obtain a new gene coding for an enzyme with an improved or modified property of interest, such as an increased Km or modification that results in changes in substrate or product specificities of the enzyme. Such changes in substrate and product specificities include, but are not limited, to changes related to stereochemistry of the substrate utilized and/or the product formed. For example, an enzyme may only catalyze the formation of a (+)-epimer of a particular product. However, after shuffling one or more nucleotide sequences encoding such an enzyme, a variant enzyme is produced that produces only the (−)-epimer of the same product. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech*. 15:436-438; Moore et al. (1997) *J. Mol. Biol*. 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458, herein incorporated by reference.

In embodiments of the invention, it is necessary to direct an enzyme for PHA synthesis to the peroxisomes of a plant. Methods for directing an enzyme to the peroxisome are well known in the art. Typically, such methods involve operably linking a nucleotide sequence encoding a peroxisome-targeting signal to the coding sequence of the enzyme or modifying the coding sequence of the enzyme to additionally encode the peroxisome-targeting signal without substantially affecting the intended function of the encoded enzyme. See, for example, Olsen et al. (1993) *Plant Cell* 5:941-952, Mullen et al. (1997) *Plant Physiol*. 115:881-889, Gould et al. (1990) *EMBO J*. 9:85-90, Flynn et al. (1998) *Plant J*. 16:709-720; Preisig-Muller and Kindl (1993) *Plant Mol. Biol*. 22:59-66 and Kato et al. (1996) *Plant Cell* 8:1601-1611; herein incorporated by reference.

It is recognized that an enzyme of the invention may be directed to the peroxisome by operably linking a peroxisome-targeting signal to the C-terminus or the N-terminus of the enzyme. It is further recognized that an enzyme which is synthesized with a peroxisome-targeting signal may be processed proteolytically in vivo resulting in the removal of the peroxisome-targeting signal from the amino acid sequence of the mature, peroxisome-localized enzyme.

It is recognized that it may be necessary to reduce or eliminate the activity of one or more enzymes in a plant that interfere with PHA production by the methods of the present invention. The activity of such an interfering enzyme may be reduced or eliminated by reducing or eliminating the synthesis of the interfering enzyme. Methods for reducing or eliminating the synthesis of a particular protein or enzyme in a plant, such as, for example, sense and antisense suppression methods, are known in the art.

Antisense suppression methods involve the use of DNA construct that is portion complementary to at least a portion of a transcript encoding the protein of interest. The antisense DNA construct is designed for the production of antisense transcripts when transcribed in a plant. Such antisense transcripts are capable of hybridizing with the corresponding native or sense transcript of the protein of interest. Modifications of the antisense sequences may be made as long as the sequences hybridize to and interfere with expression of the corresponding sense transcript. In this manner, antisense constructions having 70%, preferably 80%, more preferably 85% sequence identity to the corresponding sense transcript may be used. Furthermore, portions of the antisense nucleotides may be used to disrupt the expression of the target gene. Generally, sequences of at least 50 nucleotides, 100 nucleotides, 200 nucleotides, or greater may be used.

Sense suppression methods, also known as cosuppression methods, involve the use of DNA construct that is designed to produce of a transcript that is in the same orientation, the sense orientation, as the transcript of the protein of interest.

Methods for suppressing the production of a protein in a plant using nucleotide sequences in the sense orientation to are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

In the methods of the present invention, expression cassettes can be utilized. The cassette will include 5' and 3' regulatory sequences operably linked to the gene of interest. Generally, the expression cassette is provided with a plurality of restriction sites for insertion of the sequence to be under the transcriptional regulation of the regulatory regions. The expression cassette may additionally contain selectable marker genes.

By "operably linked" is intended the joining of two or more contiguous nucleotide sequences in such a manner that the desired functions or functions are achieved. "Operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. In the case of protein coding sequences, "operably linked" includes joining two protein coding sequences in such a manner that both sequences are in the same reading frame for translation. For example, a nucleotide sequence encoding a peroxisome-targeting signal may be joined to the 3' end of a coding sequence of a protein of the invention in such manner that both sequences are in the same reading frame for translation to yield a the protein of the invention with a C-terminal addition of the peroxisome-targeting signal.

The cassette may additionally contain at least one additional gene to be cotransformed into the organism. Alternatively, the additional gene(s) can be provided on multiple expression cassettes.

The expression cassette will include in the 5'-to-3' direction of transcription, a transcriptional and translational initiation region, a nucleotide sequence of interest, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced.

While it may be preferable to express the sequences using heterologous promoters, the native promoter sequences may be used. Such constructs would change expression levels of MFP2 in the plant or plant cell. Thus, the phenotype of the plant or plant cell is altered.

The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet*. 262:141-144; Proudfoot (1991) *Cell* 64:671-674; Sanfacon et al. (1991) *Genes Dev*. 5:141-149; Mogen et al. (1990) *Plant Cell*. 2:1261-1272; Munroe et al. (1990) *Gene* 91:151-158; Ballas et al. (1989) *Nucleic Acids Res*. 17:7891-7903; Joshi et al. (1987) *Nucleic Acids Res*. 15:9627-9639.

The coding sequences of the enzymes for PHA biosynthesis used in the practice of the invention can be optimized for enhanced expression in plants of interest. That is, the coding sequences can be synthesized using plant-preferred codons for improved expression. See, for example, Campbell and Gowri (1990) *Plant Physiol*. 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res*. 17:477-498, herein incorporated by reference. Thus, the nucleotide sequences can be optimized for expression in any plant. It is recognized that all or any part of the nucleotide sequence may be optimized or synthetic. That is, synthetic or partially optimized sequences may also be used.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5'-leader sequences in the expression cassette construct. Such leader sequences can act to enhance translation. Translation leaders are known in the art and include: picornavirus leaders, for example, EMCV leader (Encephalomyocarditis 5'-noncoding region) (Elroy-Stein, O., Fuerst, T. R., and Moss, B. (1989) *Proc. Natl. Acad. Sci. USA* 86:6126-6130); potyvirus leaders, for example, TEV leader (Tobacco Etch Virus) (Allison et al. (1986); MDMV leader (Maize Dwarf Mosaic Virus); *Virology* 154:9-20), and human immunoglobulin heavy-chain binding protein (BiP), (Macejak, D. G., and P. Sarnow (1991) *Nature* 353:90-94; untranslated leader from the coat protein mRNA of alfalfa mosaic virus (AMV RNA 4), (Jobling, S. A., and Gehrke, L., (1987) *Nature* 325:622-625; tobacco mosaic virus leader (TmV), (Gallie, D. R. et al. (1989) *Molecular Biology of RNA*, pages 237-256; and maize chlorotic mottle virus leader (MCMV) (Lommel, S. A. et al. (1991) *Virology* 81:382-385). See also, Della-Cioppa et al. (1987) *Plant Physiology*, 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, re-substitutions, e.g., transitions and transversions, may be involved. Such a fragment of DNA that has been manipulated by any method known to those skill in the art is referred to herein as a "DNA construct." The term "DNA construct" also encompasses expression cassettes, chimeric genes, synthetic genes, genes with modified coding sequences, and the like.

A number of promoters can be used in the practice of the invention. The promoters may be selected based on the desired timing, localization and level of expression genes encoding enzymes in a plant. Constitutive, seed-preferred, germination-preferred, tissue-preferred and chemical-regulatable promoters can be used in the practice of the invention. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol*. 12:619-632 and Christensen et al. (1992) *Plant Mol. Biol*. 18:675-689); pEMU (Last et al. (1991) *Theor. Appl. Genet*. 81:581-588); MAS (Velten et al. (1984) *EMBO J*. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

The methods of the invention are useful for producing PHA copolymers in seeds. Toward this end, the coding sequences for the enzymes of the invention may be utilized in expression cassettes or DNA constructs with seed-preferred promoters, seed-development promoters (those promoters active during seed development), as well as seed-germination promoters (those promoters active during seed germination). Such seed-preferred promoters include, but are not limited to, d to, Cim1 (cytokinin-induced message); cZ19B1 (maize 19 kDa zein); and celA (cellulose synthase) (see the copending application entitled "Seed-Preferred Promoters," U.S. application Ser. No. 09/377,648, filed Aug. 19, 1999, herein incorporated by reference). Gama-zein is a preferred endosperm-specific promoter. Glob-1 is a preferred embryo-specific promoter. For dicots, particular promoters include those from the following genes: phaseolin, napin, β-conglycinin, soybean lectin, and the like. For monocots, particular promoters include those from the following genes: maize 15 Kd zein, 22 KD zein, 27 kD zein, waxy, shrunken 1, shrunken 2, and globulin 1.

For tissue-preferred expression, the coding sequences of the invention can be operably linked to tissue-preferred promoters. For example, leaf-preferred promoters may be utilized if expression in leaves is desired. Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Other tissue-preferred promoters include, for example, Kawamata et al. (1997) *Plant Cell Physiol.* 38(7):792-803; Hansen et al. (1997) *Mol Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al (1996) *Plant Physiol.* 112(2):513-524; Lam (1994) *Results Probl Cell Differ.* 20:181-196; Orozco et al. (1993) *Plant Mol Biol.* 23(6):1129-1138; and Guevara-Garcia et al. (1993) *Plant J.* 4(3):495-505.

In the practice of the invention, it may be desirable to use chemical-regulatable promoters to control the expression of gene in a plant. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzene-sulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulatable promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

It is further recognized that the components of the expression cassette may be modified to increase expression. For example, truncated sequences, nucleotide substitutions or other modifications may be employed. See, for example Perlak et al.(1991) *Proc. Natl. Acad. Sci. USA* 88:3324-3328; Murray et al. (1989) *Nucleic Acid Research* 17:477-498; and WO 91/16432.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The modified plant may be grown into plants in accordance with conventional ways. See, for example, McCormick et al. (1986) *Plant Cell. Reports* 5:81-84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

In the methods of the present invention, plants genetically manipulated to produce PHA are utilized. By "genetically manipulated" is intended modifying the genome of an organism, preferably a plant, including cells and tissue thereof, by any means known to those skilled in the art. Modifications to a genome include both losses and additions of genetic material as well as any sorts of rearrangements in the organization of the genome. Such modifications can be accomplished by, for example, transforming a plant's genome with a DNA construct containing nucleotide sequences which are native to the recipient plant, non-native or a combination of both, conducting a directed sexual mating or cross pollination within a single species or between related species, fusing or transferring nuclei, inducing mutagenesis and the like.

In the practice of certain specific embodiments of the present invention, a plant is genetically manipulated to produce more than one heterologous enzyme involved in PHA synthesis. Those of ordinary skill in the art realize that this can be accomplished in any one of a number of ways.

For example, each of the respective coding sequences for such enzymes can be operably linked to a promoter and then joined together in a single continuous fragment of DNA comprising a multigenic expression cassette. Such a multigenic expression cassette can be used to transform a plant to produce the desired outcome. Alternatively, separate plants can be transformed with expression cassettes containing one or a subset of the desired set of coding sequences. Transformed plants that express the desired activity can be selected by standard methods available in the art such as, for example, assaying enzyme activities, immunoblotting using antibodies which bind to the enzymes of interest, assaying for the products of a reporter or marker gene, and the like. Then, all of the desired coding sequences can be brought together into a single plant through one or more rounds of cross pollination utilizing the previously selected transformed plants as parents.

Methods for cross pollinating plants are well known to those skilled in the art, and are generally accomplished by allowing the pollen of one plant, the pollen donor, to pollinate a flower of a second plant, the pollen recipient, and then allowing the fertilized eggs in the pollinated flower to mature into seeds. Progeny containing the entire complement of heterologous coding sequences of the two parental plants can be selected from all of the progeny by standard methods available in the art as described supra for selecting transformed plants. If necessary, the selected progeny can be used as either the pollen donor or pollen recipient in a subsequent cross pollination.

The invention can be practiced with any plant species including, but not limited to, monocots and dicots. Examples of plants of interest include, but are not limited to, corn or maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Preferably, plants of the present invention are crop plants (for example, maize, alfalfa, sunflower, *Brassica* sp., soybean, cotton, safflower, peanut, sorghum, wheat, rice, potatoes, millet, tobacco, etc.), more preferably maize and oilseed plants, yet more preferably maize plants. Such oilseed plants include, but are not limited to, *Brassica* sp., sunflower, safflower, soybean, peanut, cotton, flax, coconut and oil palm.

The following examples are offered by way of illustration and not by way of limitation.

EXPERIMENTAL

EXAMPLE 1

Engineering Plants to Produce PHA Copolymers

Bacteria can produce PHA copolymers because these substrates are apparently derived from the β-oxidation cycle; as bacterial cells are uncompartmented, both β-oxidation and PHA synthesis take place in the cytosol. In plants, however, β-oxidation is confined primarily to peroxisomes and thus offers a suitable site for copolymer production. Using methods known to those of ordinary skill in the art, signal sequences for targeting proteins to peroxisomes can be added to PHA-producing enzymes, allowing the localization of these enzymes in the peroxisomes. Such signal sequences for targeting proteins to plant peroxisomes are well known (Mullen et al. (1997) *Plant Journal* 12:313-322; Trelease et al. (1996) *Protoplasma* 195:156-167).

An intermediate in β-oxidation is S-(+)-3-hydroxyacyl-CoA. However, its configuration is unsuitable for PHA synthases, which require R-(−)-3-hydroxyacyl-CoA as a substrate (Gemgross et al. (1995) *Proc. Natl. Acad. Sci. USA* 92:6279-6283; Steinbuchel, A. (1991) *Biomaterials. Novel materials from biological materials*, D. Byrom, ed. (New York: Macmillan Publishers Ltd.), pp. 123-213). Moreover, the concentration of R-(−)-3-hydroxyacyl-CoA in the peroxisomes must be very low, as the enzyme catalyzing the proximal and distal reactions of this intermediate is multifunctional in nature (Engeland et al. (1991) *Eur. J. Biochem.* 200:171-178; Guhnemann Schafer et al. (1995) *Biochim. Biophys. Acta*. 1256:181-186). As acyl-CoA oxidase appears to be an independent enzyme (i.e., not a component of a multi-enzyme complex) in β-oxidation, its product, 2-enoyl-CoA, might be readily available for hydration into the R-(−)-epimer, provided that a hydratase capable of catalyzing this reaction is available (FIG. 1).

A multifunctional protein from yeast reportedly has only the activities of enoyl-CoA hydratase and R-(−)-3-hydroxyacyl-CoA dehydrogenase (Hiltunen et al. (1992) *J. Biol. Chem.* 267:6646-6653). Interestingly, this enoyl-CoA hydratase forms R-(−)-3-hydroxyacyl-CoA in contrast to its plant counterpart (Guhnemann et al. (1994) *Eur. J. Biochem.* 226:909-915; Kindl, H. (1993) *Biochimie* 75:22R-230). Engineering the yeast multifunctional protein (encoded by GenBank Accession No. M86456, SEQ ID NO: 3) to carry only the hydratase activity and then targeting it to the plant peroxisomes along with a PHA synthase should lead to PHA copolymer formation.

Leaf et al. ((1996) *Microbiology* 142:1169-1180) were able to produce PHB granules in the cytosol of yeast transformed with only PHB synthase. Although they were unable to pinpoint the compartment in which it was localized, they identified a 3-hydroxybutyryl-CoA dehydrogenase that catalyzed the reversible reaction between acetoacetyl-CoA and R-(−)-3-hydroxybutyryl-CoA. No further information (i.e. gene or protein sequence) is available on this enzyme yet. Once the gene for 3-hydroxyacyl-CoA dehydrogenase enzyme becomes available, it can be used in producing substrate for PHA copolymer formation in peroxisomes. It is recognized that the coding sequence of this enzyme can be manipulated to alter characteristics of the encoded enzyme to favor the synthesis R-(−)-3-hydroxyacyl-CoA over 3-ketoacyl-CoA in plant peroxisomes by techniques well known to those skilled in the art. Such techniques include, for example, e.g., DNA shuffling (Crameri et al. (1998) *Nature* 391:288-291; Stemmer, W. P. C. (1994)

*Proc. Natl. Acad. Sci. USA* 91:10747-10751; Stemmer, W. P. C. (1994) *Nature* 370:389-391).

Mammalian mitochondrial enoyl-CoA hydratase is an independent enzyme (Minami-lshi et al. (1989) *Eur. J. Biochem*. 185:73-78) which catalyzes the formation of S-(+)-3-hydroxyacyl-CoA (encoded by GenBank Accession No. U37486, SEQ ID NO: 22). The DNA encoding this enzyme can be subjected to shuffling to alter the activity of this enzyme to form the R-(−) instead of the S-(+)-epimer. Then, the shuffled DNA can be modified further to include nucleotide sequences which encodes a signal sequence for targeting to the peroxisomes.

Recently, a 2-enoyl-CoA hydratase from *Aeromonas caviae* was reported to hydrate 2-enoyl-CoA to R-3-hydroxyacyl-CoA (DDBJ Accession No. E15860, SEQ ID NO: 21) (Fukui et al. (1998) *J. Bacteriol*. 180:667-673). This enzyme can be modified to include a signal sequence for targeting to plant peroxisomes. Together with a peroxisome-localized PHA synthase, such an enoyl-CoA hydratase can catalyze the biosynthesis of copolymers.

EXAMPLE 2

Production of Specific Types of PHA in Plants

It is desirable to produce a pure copolymer of a defined monomer composition. A relatively pure copolymer would have predictable properties in comparison to a mixture of copolymers as the composition of the latter can vary according to the environment. The ability of *Pseudomonas* sp. to make copolymers of PHAs from various substrates is well known to those skilled in the art. However, the PHA synthases from these species have a broad substrate range (Caballero et al. (1995) *Int. J. Biol. Macromol*. 17:86-92; Huisman et al. (1989) *Appl. Environ. Microbiol*. 55:1949-1954;; Lee et al. (1995) *Appl. Environ. Microbiol*. 42:901-909; Ramsay et al. (1990) *Appl. Environ. Microbiol*. 56:2093-2098; Steinbuechel et al. (1992) *Appl. Environ. Microbiol*. 37:691-697; Timm et al. (1992) *Eur. J. Biochem*. 209: 1R-30). When a genomic fragment containing the PHA synthase gene from *Thiocapsa pfennigii* (see, WO 96/08566) was introduced into *Pseudomonas putida* or *A. eutrophus* strains deficient in PHA synthase, majority of the copolymer made was polyhydroxybutyrate-co-hydroxyhexanoate (HB-co-HHX) (Liebergesell et al. (1993) *Appl. Environ. Microbiol*. 40:292-300; Valentin et al. (1994) *Appl. Environ. Microbiol* 40:710-716). These are the first reports of an enzyme overcoming the barrier between short- and medium-chain monomers with respect to substrate specificity for copolymer synthesis.

Recently, a PHA synthase has been identified from *A. caviae* (DDBJ Accession No. D88825, SEQ ID NO: 11) that also makes primarily poly(hydroxybutyrate-co-hydroxyhexanoate) copolymer when the bacteria are grown in cultures containing octanoate or (Fukui et al. (1997) *J. Bacteriol*. 179:4821-4830). This enzyme, when transformed into an *A. eutrophus* strain that is deficient in PHB synthase, confers upon it the ability to make poly(hydroxybutyrate-co-hydroxyhexanoate), indicating that this enzyme is specific for these two substrates (Fukui et al. (1997) *J. Bacteriol*. 179: 4821-4830). Copolymers consisting mainly of poly(hydroxybutyrate-co-hydroxyhexanoate) can be produced if either *T. pfennigii* or *A. caviae* synthase is targeted to the plant peroxisomes along with an enoyl-CoA hydratase, 3-ketoacyl-CoA reductase, or 3-hydroxyacyl-CoA dehydrogenase that is capable of producing the R-(−) epimer (FIG. 3).

Figure 3:
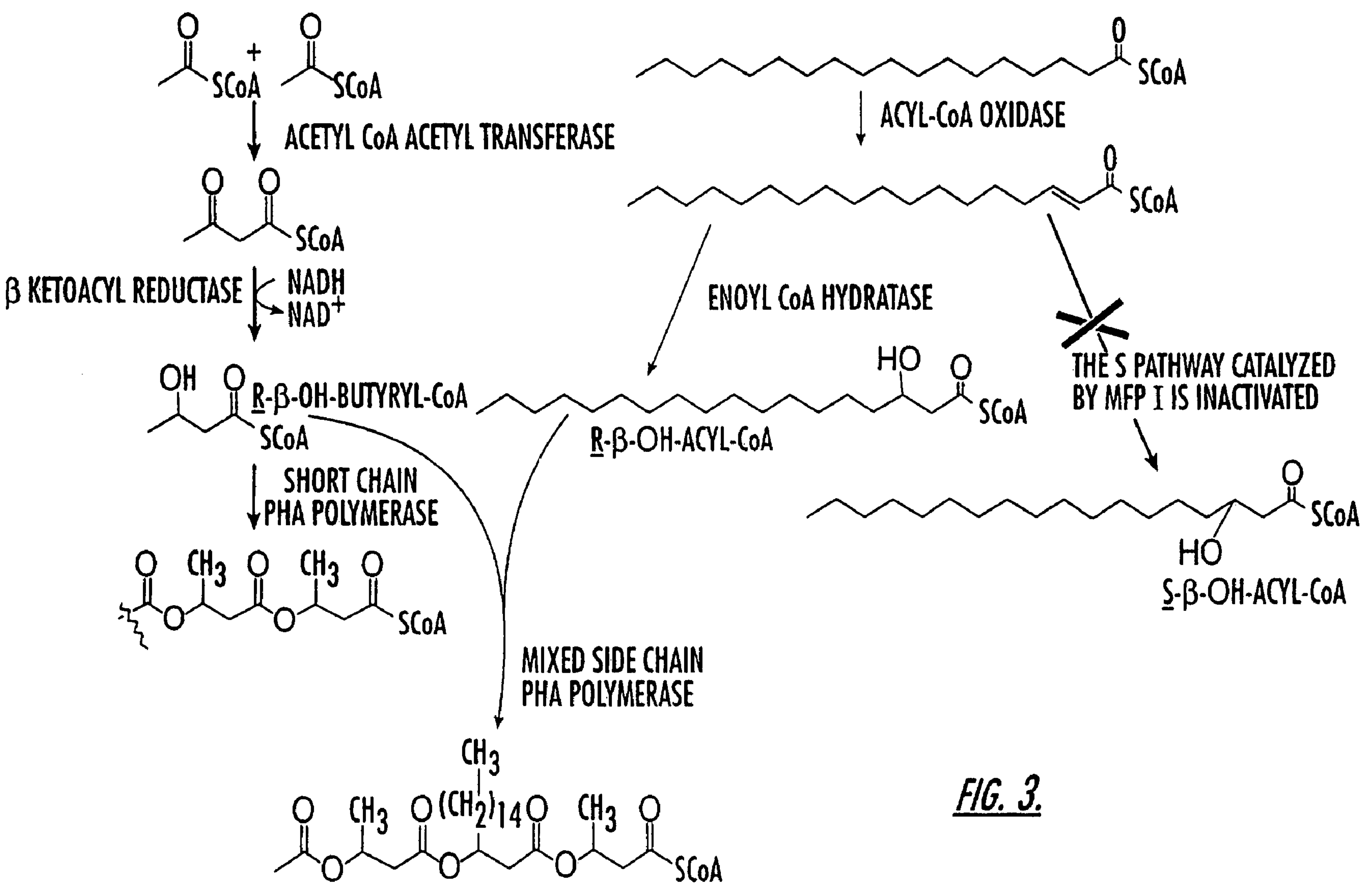
FIG. 3 schematically depicts the biosynthetic pathways for the synthesis PHB and PHA copolymers which are composed of 3-hydroxybutanoic acid monomers and other 3-hydroxyalkanoate monomers.

By introducing the other two enzymes (ketothiolase and reductase) of the PHA biosynthetic pathway into the peroxisomes, a large portion of acetyl-CoA should be partitioned to the synthesis of PHA (FIGS. 1 and 3). As ketothiolase is the most limiting enzyme in β-oxidation and is not associated with other enzymes (Kindl, H. (1987) *Lipids: Structure and Function*, P. K. Stumpf, ed. (Orlando, Fla.: Academic Press, Inc.), pp. 31-52), 3-ketobutyryl-CoA, the penultimate product of the last cycle of β-oxidation, should be readily available to the introduced reductase for conversion into 3-hydroxybutyryl-CoA. Assuming the dominant fatty acid being degraded through β-oxidation is $C_{18}$, 3-ketobutyryl-CoA would constitute >20% of the carbon flux through β-oxidation. Even if the reductase can use 25% of this intermediate, that would entail a diversion of 5% carbon from fatty acids passing through β-oxidation toward PHA formation. Introducing ketothiolase would further augment the level of 3-ketobutyryl-CoA in peroxisomes.

Expression of PHB biosynthetic machinery in the peroxisomes along with that in the plastids as well as cytosol can lead to more PHB deposition in seeds. Previously, it has been reported that the expression of PHB biosynthetic enzymes in the cytosol of plants resulted in plants being of reduced vigor or "sick" (Poirier et al. (1992) *Science* 256: 520-523). In this study, only reductase and synthase were expressed, however, allowing the cytosolic ketothiolase to supply acetoacetyl-CoA for PHB synthesis. Acetoacetyl-CoA, however, is a substrate for the synthesis of other cellular components, such as secondary metabolites and phytohormones. Enough acetoacetyl-CoA may have been diverted toward the formation of PHB that the homeostatic limits for normal cell metabolism were diminished. Alternatively, PHB granules might have physically caused disturbance in the leaf cytosol, affecting metabolism in general. The physiology of leaves may limit their usefulness as a site of PHB synthesis. A mature leaf is a source of photosynthate and as such produces and supplies photosynthate to sinks within the plant. On the other hand, a developing seed is a strong sink. Due to the myriad physiological differences between a source leaf and a strong sink like a developing seed, expression of genes encoding enzymes involved in PHB synthesis in the cytosol of a developing seed may not be as toxic as in that of a leaf. Expression of these genes in the peroxisomes of seeds can be driven by seed-preferred, chemical-regulatable or germination-preferred promoters. If these genes need to be expressed during both seed fill and germination or during only a limited portion of the seed fill period, a chemical-regulatable promoter may be desirable.

It is further recognized that in the practice of the invention, it can be advantageous to make use of transgenic or naturally occurring lines of oilseed plants that are known to have higher rates of β-oxidation in their seeds to achieve optimal PHA production in a plant.

EXAMPLE 3

Engineering a Peroxisomal 2-Enoyl-CoA Hydratase from a Yeast Multifunctional Protein To produce PHA in plant peroxisomes, it is essential to effectively divert 2-enoyl-CoA from β-oxidation and to the synthesis of R-(−)-3-hydroxyacyl-CoA, the substrate of PHA synthase. In contrast to the multifunctional protein in other organisms, yeast multifunctional protein (encoded by GenBank Accession No. M86456, SEQ ID NO: 3) converts trans-2-enoyl-CoA to R-(−)-3-hydroxyacyl-CoA. The hydratase domain of the yeast multifunctional protein utilizes a broader chain-length range of substrates than does the hydratase isolated from *Aeromonas caviae* (Fukui et al. (1998) *J. Bacteriol*. 180:667-673). Such a hydratase with such a broad substrate range finds use in the production of a wide variety of copolymers in plants.

Thus, the R-specific enoyl-CoA hydratase of the yeast multifunctional protein can used to produce R-(−)-3-hydroxyacyl-CoA for PHA synthesis in plant peroxisomes. Since the R-(−)-3-hydroxyacyl-CoA dehydrogenase of the yeast multifunctional protein requires NADH and the NADH-binding sites are located in the N-terminal portion of the polypeptide, the hydratase is likely located in the C-terminal portion of the yeast multifunctional protein. Filppula et al. ((1995) *J. Biol. Chem*. 270:27453-27457) constructed a C-terminally truncated form of the yeast multifunctional protein and showed that the mutant enzyme contained only R-(−)-3-hydroxyacyl-CoA dehydrogenase activity and thus demonstrated that the deleted C-terminal portion of the full-length yeast multifunctional protein is essential for hydratase activity. Qin et al. (1997) *Biochem. J*. 321: 21-28 described an N-truncated rat multifunctional protein with 318 amino acid residue deletion. This mutant enzyme remained full hydratase activity while its dehydrogenase activity was completely lost. These observations are in agreement with the prediction that an N-terminally truncated form of yeast multifunctional protein possess hydratase activity and lack dehydrogenase activity.

To engineer a 2-enoyl-CoA hydratase that catalyzes the synthesis of R-(−)-hydroxyacyl-CoA, the nucleotide sequence encoding the yeast multifunctional protein (GenBank Accession No. M86456, SEQ ID NO: 3) can be modified by site-directed mutagenesis and/or N-terminal truncation to remove the dehydrogenase activity. After analyzing the primary structure of the yeast multifunctional protein, two putative NADH-binding domains (residues 152-180 and residues 456-484) were identified. These two putative NADH-binding domains each possess the conserved Y and K that are a signature NADH-binding-sites. Y165 and K169 lie in the first domain while Y478 and K482 are found in the second domain, although it is unknown whether the first domain, the second one or both of them serves for NAD/NADH-binding. To eliminate dehydrogenase activity, the NADH binding sites can be disrupted to generate mutant yeast multifunctional proteins such as, for example, a first mutant enzyme having the two amino acid substitutions, Y165F and K169A and a second mutant enzyme having the two amino acid substitutions Y478F and K482A and a third mutant enzyme having the four amino acid substitutions, Y165F, K169A, Y478F, and K482A. Alternatively, two N-terminally truncated versions of the yeast multifunctional protein can be constructed by eliminating one and both NADH-binding sites (FIG. 2). Methods for assaying such enzyme activities are known in the art. See, for example, Moskowitz and Merrick (1969) *Biochemistry* 8:2748-2755 (enoyl-CoA hydratase), and Lynen and Wieland (1955) *Meth. Enzymol*. 1:566-573 (ketoacyl-CoA reductase) and Example 6 infra.

An N-terminally truncated version of the yeast multifunctional protein is set forth in SEQ ID NO: 5. A nucleotide sequence for the truncated yeast multifunctional protein is set forth in SEQ ID NO: 4. A similar approach can be used to modify any multifunctional protein known in the art.

The resulting 2-enoyl-CoA hydratase enzyme can then be modified for targeting to the peroxisome by operably linking a peroxisome-targeting signal sequence to the coding sequence for the mutant enzyme.

EXAMPLE 4

Engineering a Peroxisomal 3-ketoacyl-CoA Reductase from a Yeast Multifunctional Protein R-(−)-3-hydroxybutyryl-coenzyme A dehydrogenase (also known as acetoacetyl-CoA reductase) is encoded by phaB in PHA biosynthesis in a number of microorganisms. Such R-(−)-3-hydroxybutyryl-coenzyme A dehydrogenases all utilize NADPH as the electron donor. In one report an acetoacetyl-CoA reductase was shown to be NADH-dependent, but it produced S-(+)-3-hydroxybutyryl-CoA as its product (Liebergesell and Steinbuchel (1992) *Eur. J. Biochem*. 209:135-150). Another report showed that an NADH-dependent acetoacetyl-CoA reductase was isolated from *Parracoccus denitrificans* (Yabutani (1995) *FEMS Microbiol. Lett*. 133:85-90). Subsequent characterization confirmed that it utilized NADPH, but not NADH as an electron donor (Madison and Huisman (1999) *Microbiol. Mol. Biol. Rev*. 63:21-53).

In plant peroxisomes, it is postulated that NADPH pool is limited while NADH predominates. It is doubtful that the phaB gene product, an NADPH-dependent reductase, will function in peroxisomes. Therefore, a new enzyme that utilizes NADH as the electron donor is desired. The desired enzyme must also be able to convert 3-acetoacetyl-CoA and to R-(−)-3-hydroxybutyryl-CoA. Preferably, the desired enzyme is also capably of converting any 3-ketoacyl-CoA to an R-(−)-3-hydroxyacyl-CoA.

Using protein engineering methods, the coding sequence of the yeast multifunctional protein can be modified to produce the desired enzyme. The dehydrogenase moiety of the yeast multifunctional protein utilizes R-(−)-3-hydroxyacyl-CoA and requires NADH as its electron acceptor. Since the dehydrogenase of the yeast multifunctional protein enzyme utilizes substrates of fatty acyl-CoAs with $C_4$ or longer chain length, the desired enzyme is expected to catalyze the NADH-dependent reduction of acetoacetyl-CoA to R-(−)-3-hydroxybutyryl-CoA. Based on sequence analysis of primary structure of the protein, two NADH-binding sites residing at the N-terminal portion were identified. For example, to produce the desired 3-ketoacyl-CoA reductase, the nucleotide sequence encoding the of yeast multifunctional protein can be truncated to produce a nucleotide sequence that encodes a C-terminally truncated version of the yeast multifunctional protein which lacks the final 271 amino acid of amino acid sequence of the yeast multifunctional protein. The C-terminally truncated version of the yeast multifunctional protein is set forth in SEQ ID NO: 7. A nucleotide sequence encoding the truncated yeast multifunctional protein is set forth in SEQ ID NO: 6.

The desired 3-ketoacyl-CoA reductase can then be modified, if necessary, for targeting to the peroxisome by operably linking a peroxisome-targeting signal sequence to the coding sequence for the desired enzyme.

EXAMPLE 5

A Novel Maize Protein with Homology to Yeast MFP2

To search for homologous sequences in maize, the nucleotide sequence encoding the yeast MFP2 (GenBank Accession No. M86456, SEQ ID NO: 3) was used to search a Pioneer Hi-Bred maize EST database. An EST clone with substantial homology to the yeast sequence was identified. The 1362 bp maize EST clone was sequenced and found to be full-length (SEQ ID NO: 1) with an open reading frame encoding a polypeptide of 314 amino acids (SEQ ID NO: 2). Interestingly, in comparison, the yeast MFP2 is comprised of an amino acid sequence which is 900 amino acids in length. Further sequence analysis revealed that the maize amino acid sequence corresponds to the C-terminal portion of the yeast MFP2 that is believed to be a 2-enoyl-CoA hydratase domain (FIG. 2) Unlike the yeast MFP2, the smaller maize MFP2-like polypeptide lacks the dehydrogenase domain of the yeast and mammalian MFP2s and does not appear to contain a peroxisome-targeting sequence.

Thus, on the basis of homology to the yeast MFP2, the maize MFP2-like polypeptide is predicted to encode a 2-enoyl-CoA hydratase. Such a hydratase can be targeted to the peroxisome for use in PHA production therein by operably linking a peroxisome-targeting signal sequence to the coding sequence for the maize polypeptide.

The present invention discloses a novel protein from maize with homology to MFP2s. While MFP2s are found in several fungi and in several mammals including, but not limited to, mouse, guinea pig, human and pig, no plant sequence has yet been publically disclosed. It has been generally believed that MFPs are unique to fungi and animals. The discovery of the maize MFP2-like polypeptide, which shares substantial homology with the yeast MFP2, indicates, however that, at least, the hydratase domain of MFP2 is also found in plants.

While the maize MFP2-like polypeptide shares significant homology to MFP2s from fungi and mammals, the maize protein possesses several notable differences. In addition to the lack of a dehydrogenase domain, the maize MFP2-like polypeptide does not contains any known peroxisomal-targeting sequences in its N-terminal or C-terminal portions. This is different from yeast and mammalian MFP2s which are considered to be localized in peroxisomes and play roles in fatty acid β-oxidation. Thus, the maize MFP2-like polypeptide is likely to play a physiological role in plants that is distinct from that of known MFP2s.

EXAMPLE 6

Assaying the Activities of PHA Synthesis Enzymes

Figure 4:
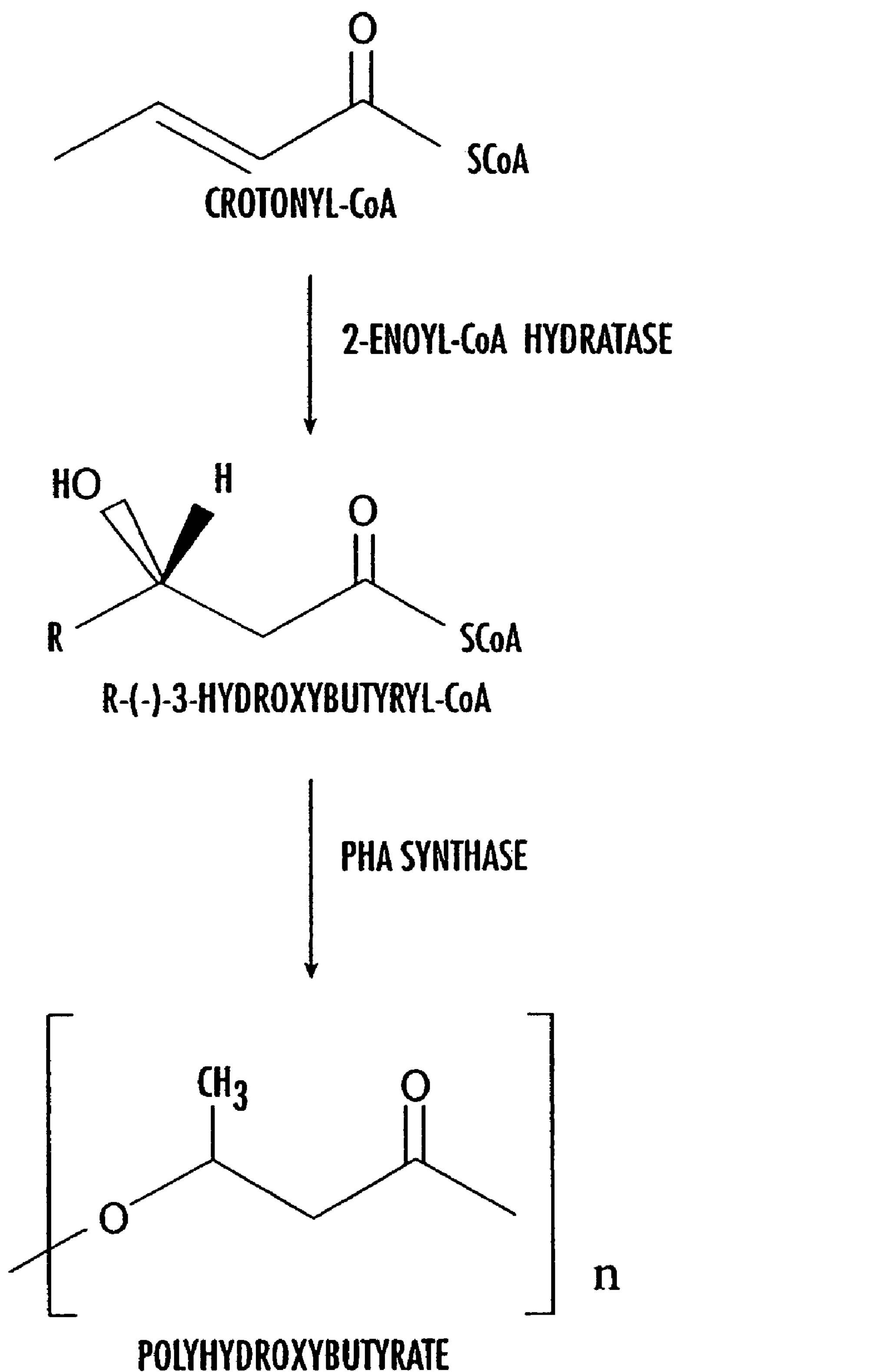
FIG. 4 schematically illustrates a functional assay for a 2-enoyl-CoA hydratase that catalyzes the synthesis of R-(−)-3-hydroxyacyl-CoA. This hydratase converts crotonyl-CoA to R-(−)-3-hydroxyacyl-CoA which is then utilized as the substrate by PHA synthase to form polymers. PHA synthase utiltizes R-(−)-3-hydroxyacyl-CoAs, but not S-3-hydroxyacyl-CoAs. Detection of polymer formation in the presence of crotonyl-CoA demonstrates that R-(−)-3-hydroxyacyl-CoA was produced.

To test the activity of the maize MFP2-like polypeptide and the truncated yeast MFP2 (hydratase domain) prepared as described supra, their respective nucleotide sequences (SEQ ID NOs: 1 and 4) and that of the full-length yeast MFP2 (SEQ ID NO: 3) were cloned into appropriate bacterial expression vectors and used to transform *E. coli* using standard techniques known in the art for expressing recombinant proteins and transforming bacteria. Total protein extracts were isolated from IPTG-induced *E. coli* (strain BL21) harboring a plasmid comprising the nucleotide sequence of SEQ ID NO: 3 (pYMFP), the nucleotide sequence of SEQ ID NO: 4 (PYHL) or the nucleotide sequence of SEQ ID NO: 1 (pMHL). The activities of the truncated proteins were tested using the functional assay schematically illustrated in FIG. 4. The reaction mixture consisted of 20 μl of PHA synthase preparation (19 mg/ml), 50 μl of *E. coli* extract, 50 mM Tris-HCl, pH 7.5 and μM of crotonyl-CoA, acetoacetyl-CoA (AcAcCoA), or 3-hydroxybutryl-CoA (3HB-CoA) in total volume of 300 μl. The reaction was started by the addition of the substrate and incubated at 37° C. for two hours.

Figure 5:
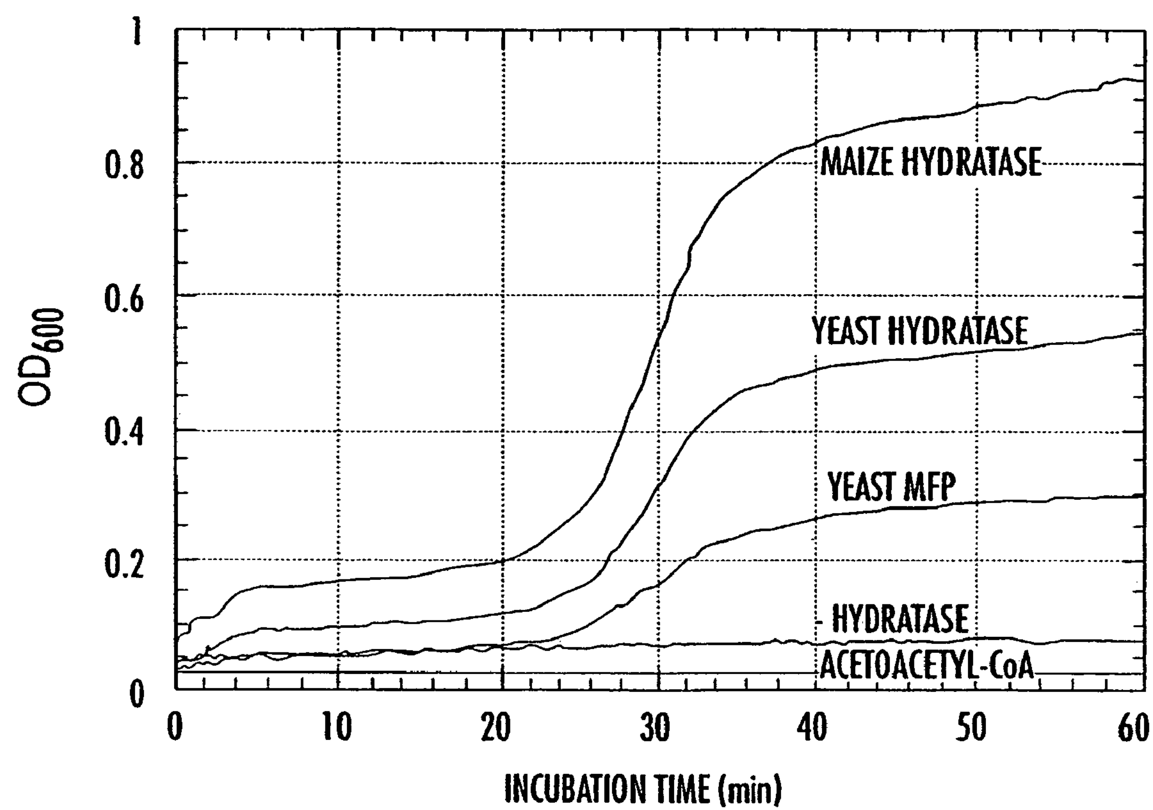
FIG. 5 is a graphical depiction of the results of a functional assay for the activity of a 2-enoyl-CoA hydratase that catalyzes the synthesis R-(−)-3-hydroxyacyl-CoA.

The results are presented in Table 1 and FIG. 5. With crotonyl-CoA as a substrate, polymer formation was detected in cultures of *E. coli* that were transformed with a nucleotide sequences encoding either the full-length yeast MFP2 (pYMFP), the truncated yeast MFP2 (yYHL), or the maize MFP2-like polypeptide (yMHL). The vector-only control (Table 1, reaction 1) indicated that polymer was not formed in the presence of crotonyl-CoA without one of the three nucleotide sequences (SEQ ID NOs: 1, 3, and 4). Thus, proteins encoded by each of the nucleotide sequences can catalyze the conversion of a crotonyl-CoA, which is a 2-enoyl-CoA, into R-(−)-3-hydroxyacyl-CoA, which can then be used for PHA synthesis as a substatrate for PHA synthase.

Comparison of the relative hydratase activities, as measured by PHA formation, for the proteins encoded by SEQ ID NOs: 1, 3 and 4 is provided in FIG. 5. The highest relative hydratase activity was detected in the cultures expressing the maize MFP2-like polypeptide (maize hydratase), followed by the truncated yeast MFP2 (yeast hydratase) and the full-length yeast MFP2 (yeast MFP). The results indicate that the removal an N-terminal portion of an MFP2 can lead to increased hydratase activity, as determined by increased PHA production, when compared to the hydratase activity of the full-length MFP2.

In general, results presented in Table 1 and FIG. 5 demonstrate that both the maize MFP2-like peptide and the truncated yeast MFP2 possess a hydratase activity that can be used for PHA synthesis in a host cell. Given that 2-enoyl-CoA substrates are found in the peroxisome, the maize MFP2-like polypeptide and the truncated yeast MFP2 of the invention can be targeted to peroxisome, along with other necessary enzymes, for PHA synthesis therein. The results further demonstrate that a truncated MFP2 can provide an improvement in PHA production in an living organism, when compared to the full-length MFP.

TABLE 1

Functional Assay for the Presence of an 2-enoyl-CoA Hydratase Activity

| Reaction | Substrate | Hydratase | Polymer Formed |
|---|---|---|---|
| 1 | crotonyl-CoA | vector only | No |
| 2 | crotonyl-CoA | pMHL | Yes |
| 3 | crotonyl-CoA | pYHL | Yes |
| 4 | crotonyl-CoA | pYMFP | Yes |
| 5 | 3HB-CoA | 50 μl buffer | Yes |
| 6 | AcAcCoA | 50 μl buffer | No |
| 7 | AcAcCoA | pMHL | No |

EXAMPLE 7

Transformation and Regeneration of Transgenic Maize Plants by Particle Bombardment Immature maize embryos from greenhouse donor plants are bombarded with a plasmid comprising a nucleotide sequence of the invention encoding an enzyme involved in PHA synthesis operably linked to a seed-preferred promoter and the selectable marker gene PAT (Wohlleben et al. (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the nucleotide sequence of the invention encoding an enzyme involved in PHA synthesis linked to a seed-preferred promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water

10 μl (1 μg) DNA in Tris EDTA buffer (1 μg total DNA)

100 μl 2.5 M $CaCl_2$

10 μl 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for PHA content and/or the activity or level of the enzyme of the invention.

Bombardment and Culture Media

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant*. 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

EXAMPLE 8

Production of Transgenic Maize Plants via *Agrobacterium*-Mediated Transformation For *Agrobacterium*-mediated transformation of maize with a nucleotide sequence of the invention encoding an enzyme involved in PHA synthesis, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the nucleotide sequence of the invention to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

EXAMPLE 9

Production of Transformed Soybean Plants

Soybean embryos are bombarded with a plasmid comprising a nucleotide sequence of the invention encoding an enzyme involved in PHA synthesis operably linked to a seed-preferred as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70-73, U.S. Pat. No. 4,945,050). A Du Pont Biolistic PDS 1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette comprising the nucleotide sequence of the invention operably linked to the seed-preferred promoter can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl $CaCl_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 10

Genetic Transformation of Sunflower Plants

Sunflower meristem tissues are transformed with an expression cassette comprising a nucleotide sequence of the invention encoding an enzyme involved in PHA synthesis operably linked to a seed-preferred promoter as follows (see also European Patent Number EP 0 486233, herein incorporated by reference, and Malone-Schoneberg et al. (1994) *Plant Science* 103:199-207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al.(1990) *Plant Cell Rep*. 9: 55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant*. 15: 473-497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid (GA3), pH 5.6, and 8 g/l Phytagar.

The explants are subjected to microprojectile bombardment prior to *Agrobacterium* treatment (Bidney et al. (1992) *Plant Mol. Biol*. 18: 301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA 105 is used in all transformation experiments. A binary plasmid vector comprising the expression cassette that contains the nucleotide sequence of the invention encoding an enzyme involved in PHA synthesis operably linked to the seed-preferred promoter is introduced into *Agrobacterium* strain EHA105 via freeze-thawing as described by Holsters et al. (1978) *Mol. Gen. Genet*. 163:181-187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying, for example, for PHA production as described supra.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by analysis in leaf extracts of enzyme activity of the enzyme encoded by the nucleotide sequence of the invention of leaf extracts, while transgenic seeds harvested from NPTII-positive $T_0$ plants are identified by similar enzyme activity analyses of small portions of dry seed cotyledons.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. An isolated polypeptide comprising the amino acid sequence set forth in SEQ ID NO: 2.

2. An isolated polypeptide comprising an amino acid sequence having at least 95% sequence identity to the amino acid sequence set forth in SEQ ID NO:2, wherein said polypeptide has 2-enoyl-CoA hydratase activity.

* * * * *

UNITED STATES PATENT AND TRADEMARK OFFICE

CERTIFICATE OF CORRECTION

PATENT NO. : 7,341,856 B2
APPLICATION NO. : 11/487811
DATED : March 11, 2008
INVENTOR(S) : Dhugga et al.

It is certified that error appears in the above-identified patent and that said Letters Patent is hereby corrected as shown below:

On the Title Page

Item (62): "Division of application No. 10/089,281, filed as"

should read

--Division of application No. 10/089,281, now U.S. Pat. No. 7,176,349, filed as--

Signed and Sealed this

Tenth Day of February, 2009

JOHN DOLL
*Acting Director of the United States Patent and Trademark Office*

SEQUENCE LISTING

```
<160> NUMBER OF SEQ ID NOS: 27

<210> SEQ ID NO 1
<211> LENGTH: 1362
<212> TYPE: DNA
<213> ORGANISM: Zea mays
<220> FEATURE:
<221> NAME/KEY: CDS
<222> LOCATION: (233)..(1174)

<400> SEQUENCE: 1

gaattcccgg gtcgacccac gcgtccggtc ggcggggctg ccgcctgccg catcctcccc      60

tcgcccaccg tcgacgactt gatcccctcc caccgttgag gccgcctcct cacggcagcg     120

agccagcgac tcctctcttc gtctcctaca agtagccaga caccactccg actttgccgg     180

caacccgtcg acagcgacga ggcgcagcat aaggcatacg ggcacggcgg cc atg gcg     238
                                                          Met Ala
                                                            1

acc agc tcc aaa ccc gcc gcg ccc gtg gac ccc atg gtc gtg ctc gcc      286
Thr Ser Ser Lys Pro Ala Ala Pro Val Asp Pro Met Val Val Leu Ala
        5                  10                  15

cac gag ttc ccc gag gtg tca ttc gac tac gac gag agg gat gta gcg      334
His Glu Phe Pro Glu Val Ser Phe Asp Tyr Asp Glu Arg Asp Val Ala
    20                  25                  30

ttg tac gcg ctc ggg gtt ggt gcc tgc ggc gat gac gcc gtc gac gag      382
Leu Tyr Ala Leu Gly Val Gly Ala Cys Gly Asp Asp Ala Val Asp Glu
 35                  40                  45                  50

aag gag ctt cac ttc gtg tac cac agg gat ggg cag cca cac att aag      430
Lys Glu Leu His Phe Val Tyr His Arg Asp Gly Gln Pro His Ile Lys
                 55                  60                  65

acc ctt cct act ttt gtt tct tta ttt ccc aac aag aac agc aat ggg      478
Thr Leu Pro Thr Phe Val Ser Leu Phe Pro Asn Lys Asn Ser Asn Gly
             70                  75                  80

ctt gga ttt gtt gat gtg cct ggc ctt aac ttt gat gca agc ctt cta      526
Leu Gly Phe Val Asp Val Pro Gly Leu Asn Phe Asp Ala Ser Leu Leu
        85                  90                  95
```

-continued

```
ctg cat ggt caa caa tac ata gag atc tat agg cca atc cct tcg tat      574
Leu His Gly Gln Gln Tyr Ile Glu Ile Tyr Arg Pro Ile Pro Ser Tyr
    100                 105                 110

gtc agt gtt gta aac agg gtt aaa gta gtt ggt ttg cac gac aag ggg      622
Val Ser Val Val Asn Arg Val Lys Val Val Gly Leu His Asp Lys Gly
115                 120                 125                 130

aaa gca act att ctt gag ctc gaa act acc aca agc ctc aaa gag tca      670
Lys Ala Thr Ile Leu Glu Leu Glu Thr Thr Thr Ser Leu Lys Glu Ser
                135                 140                 145

ggg gaa att tta tgc atg aac agg agt act atc tac ttg cgt ggt gct      718
Gly Glu Ile Leu Cys Met Asn Arg Ser Thr Ile Tyr Leu Arg Gly Ala
            150                 155                 160

gga ggg ttt tca gac tct tca cgg cca tac tca tat gct acc tat cct      766
Gly Gly Phe Ser Asp Ser Ser Arg Pro Tyr Ser Tyr Ala Thr Tyr Pro
        165                 170                 175

gct aat caa gtt tct cgc att tct att cca aat tcg gca cct tct gca      814
Ala Asn Gln Val Ser Arg Ile Ser Ile Pro Asn Ser Ala Pro Ser Ala
    180                 185                 190

gta tgc gac gac cag aca aag caa tcc cag gca ttg tta tac agg cta      862
Val Cys Asp Asp Gln Thr Lys Gln Ser Gln Ala Leu Leu Tyr Arg Leu
195                 200                 205                 210

tct ggg gat tac aat cct ttg cat tca gac cca gat att gca cag ctt      910
Ser Gly Asp Tyr Asn Pro Leu His Ser Asp Pro Asp Ile Ala Gln Leu
                215                 220                 225

gct ggg ttc acc cgt cca atc ctg cac ggc ctc tgc acc cta gga ttc      958
Ala Gly Phe Thr Arg Pro Ile Leu His Gly Leu Cys Thr Leu Gly Phe
            230                 235                 240

gct gct cgc gcc gtc ata aaa tct ttc tgc aac ggc gaa ccg act gcg     1006
Ala Ala Arg Ala Val Ile Lys Ser Phe Cys Asn Gly Glu Pro Thr Ala
        245                 250                 255

gtg aag agc atc ttc ggc cgt ttc ctt ctg cac gtc tac ccc ggg gaa     1054
Val Lys Ser Ile Phe Gly Arg Phe Leu Leu His Val Tyr Pro Gly Glu
    260                 265                 270

acg ttg tcc act gag atg tgg ctt gac ggc cag aag gtg cac tac caa     1102
Thr Leu Ser Thr Glu Met Trp Leu Asp Gly Gln Lys Val His Tyr Gln
275                 280                 285                 290

acg aag gcc aag gag cgg aac cga gct gtc ctc tct gga tat gtg ttg     1150
Thr Lys Ala Lys Glu Arg Asn Arg Ala Val Leu Ser Gly Tyr Val Leu
                295                 300                 305

ctc cag cac atc ccc tcg tca ttg taagtaaaag ttttgtttct taaaattggt    1204
Leu Gln His Ile Pro Ser Ser Leu
            310

gcccgctgaa agcatttggc ttggctgtga taaattgagc acgaggtggg ctgccactgt   1264

aatgatagcc atgtatgggt ctgcacataa cacattcgta ctgtattgat aagaagcacg   1324

taccacttaa atacgcagat ccgaacgtct tgattttt                            1362


<210> SEQ ID NO 2
<211> LENGTH: 314
<212> TYPE: PRT
<213> ORGANISM: Zea mays

<400> SEQUENCE: 2

Met Ala Thr Ser Ser Lys Pro Ala Ala Pro Val Asp Pro Met Val Val
  1               5                  10                  15

Leu Ala His Glu Phe Pro Glu Val Ser Phe Asp Tyr Asp Glu Arg Asp
            20                  25                  30

Val Ala Leu Tyr Ala Leu Gly Val Gly Ala Cys Gly Asp Asp Ala Val
        35                  40                  45
```

-continued

```
Asp Glu Lys Glu Leu His Phe Val Tyr His Arg Asp Gly Gln Pro His
     50                  55                  60

Ile Lys Thr Leu Pro Thr Phe Val Ser Leu Phe Pro Asn Lys Asn Ser
 65                  70                  75                  80

Asn Gly Leu Gly Phe Val Asp Val Pro Gly Leu Asn Phe Asp Ala Ser
                 85                  90                  95

Leu Leu Leu His Gly Gln Gln Tyr Ile Glu Ile Tyr Arg Pro Ile Pro
            100                 105                 110

Ser Tyr Val Ser Val Val Asn Arg Val Lys Val Val Gly Leu His Asp
        115                 120                 125

Lys Gly Lys Ala Thr Ile Leu Glu Leu Glu Thr Thr Thr Ser Leu Lys
    130                 135                 140

Glu Ser Gly Glu Ile Leu Cys Met Asn Arg Ser Thr Ile Tyr Leu Arg
145                 150                 155                 160

Gly Ala Gly Gly Phe Ser Asp Ser Ser Arg Pro Tyr Ser Tyr Ala Thr
                165                 170                 175

Tyr Pro Ala Asn Gln Val Ser Arg Ile Ser Ile Pro Asn Ser Ala Pro
            180                 185                 190

Ser Ala Val Cys Asp Asp Gln Thr Lys Gln Ser Gln Ala Leu Leu Tyr
        195                 200                 205

Arg Leu Ser Gly Asp Tyr Asn Pro Leu His Ser Asp Pro Asp Ile Ala
    210                 215                 220

Gln Leu Ala Gly Phe Thr Arg Pro Ile Leu His Gly Leu Cys Thr Leu
225                 230                 235                 240

Gly Phe Ala Ala Arg Ala Val Ile Lys Ser Phe Cys Asn Gly Glu Pro
                245                 250                 255

Thr Ala Val Lys Ser Ile Phe Gly Arg Phe Leu Leu His Val Tyr Pro
            260                 265                 270

Gly Glu Thr Leu Ser Thr Glu Met Trp Leu Asp Gly Gln Lys Val His
        275                 280                 285

Tyr Gln Thr Lys Ala Lys Glu Arg Asn Arg Ala Val Leu Ser Gly Tyr
    290                 295                 300

Val Leu Leu Gln His Ile Pro Ser Ser Leu
305                 310
```

<210> SEQ ID NO 3
<211> LENGTH: 3252
<212> TYPE: DNA
<213> ORGANISM: Saccharomyces cerevisiae

<400> SEQUENCE: 3

```
tagaactctc ggcggttatt tgccaatttt tactccaacg gggatcaaca tcagcaagaa     60

agcaaaggag gatggggtaa aaaaacaagg aagacaagta aagaaattat ataagaagtc    120

gtttctggct gctttactcc cagtgttgaa aggtagaagg acttatcagc taatttatta    180

agcaaggtac acatatacga gctaaacaaa cattcgattt atttcttatt tgagtaagcc    240

atgcctggaa atttatcctt caaagataga gttgttgtaa tcacgggcgc tggagggggc    300

ttaggtaagg tgtatgcact agcttacgca agcagaggtg caaaagtggt cgtcaatgat    360

ctaggtggca ctttgggtgg ttcaggacat aactccaaag ctgcagactt agtggtggat    420

gagataaaaa aagccggagg tatagctgtg gcaaattacg actctgttaa tgaaaatgga    480

gagaaaataa ttgaaacggc tataaaagaa ttcggcaggg ttgatgtact aattaacaac    540

gctggaatat taagggatgt ttcatttgca aagatgacag aacgtgagtt tgcatctgtg    600
```

-continued

```
gtagatgttc atttgacagg tggctataag ctatcgcgtg ctgcttggcc ttatatgcgc    660
tctcagaaat ttggtagaat cattaacacc gcttcccctg ccggtctatt tggaaatttt    720
ggtcaagcta attattcagc agctaaaatg ggcttagttg gtttggcgga aaccctcgcg    780
aaggagggtg ccaaatacaa cattaatgtt aattcaattg cgccattggc tagatcacgt    840
atgacagaaa acgtgttacc accacatatc ttgaaacagt taggaccgga aaaaattgtt    900
cccttagtac tctatttgac acacgaaagt acgaaagtgt caaactccat ttttgaactc    960
gctgctggat tctttggaca gctcagatgg gagaggtctt ctggacaaat tttcaatcca   1020
gaccccaaga catatactcc tgaagcaatt ttaaataagt ggaaggaaat cacagactat   1080
agggacaagc catttaacaa aactcagcat ccatatcaac tctcggatta taatgattta   1140
atcaccaaag caaaaaaatt acctcccaat gaacaaggct cagtgaaaat caagtcgctt   1200
tgcaacaaag tcgtagtagt tacgggtgca ggaggtggtc ttgggaagtc tcatgcaatc   1260
tggtttgcac ggtacggtgc gaaggtagtt gtaaatgaca tcaaggatcc tttttcagtt   1320
gttgaagaaa taaataaact atatggtgaa ggcacagcca ttccagattc ccatgatgtg   1380
gtcaccgaag ctcctctcat tatccaaact gcaataagta agtttcagag agtagacatc   1440
ttggtcaata acgctggtat tttgcgtgac aaatcttttt taaaaatgaa agatgaggaa   1500
tggtttgctg tcctgaaagt ccaccttttt tccacatttt cattgtcaaa agcagtatgg   1560
ccaatattta ccaaacaaaa gtctggattt attatcaata ctacttctac ctcaggaatt   1620
tatggtaatt ttggacaggc caattatgcc gctgcaaaag ccgccatttt aggattcagt   1680
aaaactattg cactggaagg tgccaagaga ggaattattg ttaatgttat cgctcctcat   1740
gcagaaacgg ctatgacaaa gactatattc tcggagaagg aattatcaaa ccactttgat   1800
gcatctcaag tctccccact tgttgttttg ttggcatctg aagaactaca aaagtattct   1860
ggaagaaggg ttattggcca attattcgaa gttggcggtg gttggtgtgg gcaaaccaga   1920
tggcaaagaa gttccggtta tgtttctatt aaagagacta ttgaaccgga agaaattaaa   1980
gaaaattgga accacatcac tgatttcagt cgcaacacta tcaacccgag ctccacagag   2040
gagtcttcta tggcaacctt gcaagccgtg caaaaagcgc actcttcaaa ggagttggat   2100
gatggattat tcaagtacac taccaaggat tgtatcttgt acaatttagg acttggatgc   2160
acaagcaaag agcttaagta cacctacgag aatgatccag acttccaagt tttgcccacg   2220
ttcgccgtca ttccatttat gcaagctact gccacactag ctatggacaa tttagtcgat   2280
aacttcaatt atgcaatgtt actgcatgga gaacaatatt ttaagctctg cacgccgaca   2340
atgccaagta atggaactct aaagacactt gctaaacctt tacaagtact tgacaagaat   2400
ggtaaagccg ctttagttgt tggtggcttc gaaacttatg acattaaaac taagaaactc   2460
atagcttata acgaaggatc gttcttcatc aggggcgcac atgtacctcc agaaaaggaa   2520
gtgagggatg ggaaaagagc caagtttgct gtccaaaatt ttgaagtgcc acatggaaag   2580
gtaccagatt ttgaggcgga gatttctacg aataaagatc aagccgcatt gtacaggtta   2640
tctggcgatt tcaatccttt acatatcgat cccacgctag ccaaagcagt taaatttcct   2700
acgccaattc tgcatgggct ttgtacatta ggtattagtg cgaaagcatt gtttgaacat   2760
tatggtccat atgaggagtt gaaagtgaga tttaccaatg ttgttttccc aggtgatact   2820
ctaaaggtta aagcttggaa gcaaggctcg gttgtcgttt ttcaaacaat tgatacgacc   2880
agaaacgtca ttgtattgga taacgccgct gtaaaactat cgcaggcaaa atctaaacta   2940
taatacaaaa aaagatttga ataatataaa aaatagcgat tatattcttt tcatttaaca   3000
```

```
gctttgttaa gccatatcct tacatacatc tttccctaca taactaacct acccatttta   3060

agtacttttt ctttacggac gcaacttttt tgtcatgtgt aatattaaca gttttaatct   3120

atatagagga agaggatgga taatattaca aagtgtatat aggttgtata tagatacatg   3180

catatgatgg gaagactatg aagagagaga tagtcatcat ggtaagacat ttatccagaa   3240

attcatgaat tc                                                       3252


<210> SEQ ID NO 4
<211> LENGTH: 1566
<212> TYPE: DNA
<213> ORGANISM: Saccharomyces cerevisiae
<220> FEATURE:
<221> NAME/KEY: CDS
<222> LOCATION: (1)..(1563)
<220> FEATURE:
<223> OTHER INFORMATION: Nucleotides 4-1566 of SEQ ID NO: 4  corresponds
      to nucleotides 1381-2943 of SEQ ID NO: 3.

<400> SEQUENCE: 4

atg gtc acc gaa gct cct ctc att atc caa act gca ata agt aag ttt       48
Met Val Thr Glu Ala Pro Leu Ile Ile Gln Thr Ala Ile Ser Lys Phe
  1               5                  10                  15

cag aga gta gac atc ttg gtc aat aac gct ggt att ttg cgt gac aaa       96
Gln Arg Val Asp Ile Leu Val Asn Asn Ala Gly Ile Leu Arg Asp Lys
             20                  25                  30

tct ttt tta aaa atg aaa gat gag gaa tgg ttt gct gtc ctg aaa gtc      144
Ser Phe Leu Lys Met Lys Asp Glu Glu Trp Phe Ala Val Leu Lys Val
         35                  40                  45

cac ctt ttt tcc aca ttt tca ttg tca aaa gca gta tgg cca ata ttt      192
His Leu Phe Ser Thr Phe Ser Leu Ser Lys Ala Val Trp Pro Ile Phe
     50                  55                  60

acc aaa caa aag tct gga ttt att atc aat act act tct acc tca gga      240
Thr Lys Gln Lys Ser Gly Phe Ile Ile Asn Thr Thr Ser Thr Ser Gly
 65                  70                  75                  80

att tat ggt aat ttt gga cag gcc aat tat gcc gct gca aaa gcc gcc      288
Ile Tyr Gly Asn Phe Gly Gln Ala Asn Tyr Ala Ala Ala Lys Ala Ala
                 85                  90                  95

att tta gga ttc agt aaa act att gca ctg gaa ggt gcc aag aga gga      336
Ile Leu Gly Phe Ser Lys Thr Ile Ala Leu Glu Gly Ala Lys Arg Gly
            100                 105                 110

att att gtt aat gtt atc gct cct cat gca gaa acg gct atg aca aag      384
Ile Ile Val Asn Val Ile Ala Pro His Ala Glu Thr Ala Met Thr Lys
        115                 120                 125

act ata ttc tcg gag aag gaa tta tca aac cac ttt gat gca tct caa      432
Thr Ile Phe Ser Glu Lys Glu Leu Ser Asn His Phe Asp Ala Ser Gln
    130                 135                 140

gtc tcc cca ctt gtt gtt ttg ttg gca tct gaa gaa cta caa aag tat      480
Val Ser Pro Leu Val Val Leu Leu Ala Ser Glu Glu Leu Gln Lys Tyr
145                 150                 155                 160

tct gga aga agg gtt att ggc caa tta ttc gaa gtt ggc ggt ggt tgg      528
Ser Gly Arg Arg Val Ile Gly Gln Leu Phe Glu Val Gly Gly Gly Trp
                165                 170                 175

tgt ggg caa acc aga tgg caa aga agt tcc ggt tat gtt tct att aaa      576
Cys Gly Gln Thr Arg Trp Gln Arg Ser Ser Gly Tyr Val Ser Ile Lys
            180                 185                 190

gag act att gaa ccg gaa gaa att aaa gaa aat tgg aac cac atc act      624
Glu Thr Ile Glu Pro Glu Glu Ile Lys Glu Asn Trp Asn His Ile Thr
        195                 200                 205

gat ttc agt cgc aac act atc aac ccg agc tcc aca gag gag tct tct      672
Asp Phe Ser Arg Asn Thr Ile Asn Pro Ser Ser Thr Glu Glu Ser Ser
```

-continued

```
    210                 215                 220

atg gca acc ttg caa gcc gtg caa aaa gcg cac tct tca aag gag ttg      720
Met Ala Thr Leu Gln Ala Val Gln Lys Ala His Ser Ser Lys Glu Leu
225                 230                 235                 240

gat gat gga tta ttc aag tac act acc aag gat tgt atc ttg tac aat      768
Asp Asp Gly Leu Phe Lys Tyr Thr Thr Lys Asp Cys Ile Leu Tyr Asn
                245                 250                 255

tta gga ctt gga tgc aca agc aaa gag ctt aag tac acc tac gag aat      816
Leu Gly Leu Gly Cys Thr Ser Lys Glu Leu Lys Tyr Thr Tyr Glu Asn
            260                 265                 270

gat cca gac ttc caa gtt ttg ccc acg ttc gcc gtc att cca ttt atg      864
Asp Pro Asp Phe Gln Val Leu Pro Thr Phe Ala Val Ile Pro Phe Met
        275                 280                 285

caa gct act gcc aca cta gct atg gac aat tta gtc gat aac ttc aat      912
Gln Ala Thr Ala Thr Leu Ala Met Asp Asn Leu Val Asp Asn Phe Asn
    290                 295                 300

tat gca atg tta ctg cat gga gaa caa tat ttt aag ctc tgc acg ccg      960
Tyr Ala Met Leu Leu His Gly Glu Gln Tyr Phe Lys Leu Cys Thr Pro
305                 310                 315                 320

aca atg cca agt aat gga act cta aag aca ctt gct aaa cct tta caa     1008
Thr Met Pro Ser Asn Gly Thr Leu Lys Thr Leu Ala Lys Pro Leu Gln
                325                 330                 335

gta ctt gac aag aat ggt aaa gcc gct tta gtt gtt ggt ggc ttc gaa     1056
Val Leu Asp Lys Asn Gly Lys Ala Ala Leu Val Val Gly Gly Phe Glu
            340                 345                 350

act tat gac att aaa act aag aaa ctc ata gct tat aac gaa gga tcg     1104
Thr Tyr Asp Ile Lys Thr Lys Lys Leu Ile Ala Tyr Asn Glu Gly Ser
        355                 360                 365

ttc ttc atc agg ggc gca cat gta cct cca gaa aag gaa gtg agg gat     1152
Phe Phe Ile Arg Gly Ala His Val Pro Pro Glu Lys Glu Val Arg Asp
    370                 375                 380

ggg aaa aga gcc aag ttt gct gtc caa aat ttt gaa gtg cca cat gga     1200
Gly Lys Arg Ala Lys Phe Ala Val Gln Asn Phe Glu Val Pro His Gly
385                 390                 395                 400

aag gta cca gat ttt gag gcg gag att tct acg aat aaa gat caa gcc     1248
Lys Val Pro Asp Phe Glu Ala Glu Ile Ser Thr Asn Lys Asp Gln Ala
                405                 410                 415

gca ttg tac agg tta tct ggc gat ttc aat cct tta cat atc gat ccc     1296
Ala Leu Tyr Arg Leu Ser Gly Asp Phe Asn Pro Leu His Ile Asp Pro
            420                 425                 430

acg cta gcc aaa gca gtt aaa ttt cct acg cca att ctg cat ggg ctt     1344
Thr Leu Ala Lys Ala Val Lys Phe Pro Thr Pro Ile Leu His Gly Leu
        435                 440                 445

tgt aca tta ggt att agt gcg aaa gca ttg ttt gaa cat tat ggt cca     1392
Cys Thr Leu Gly Ile Ser Ala Lys Ala Leu Phe Glu His Tyr Gly Pro
    450                 455                 460

tat gag gag ttg aaa gtg aga ttt acc aat gtt gtt ttc cca ggt gat     1440
Tyr Glu Glu Leu Lys Val Arg Phe Thr Asn Val Val Phe Pro Gly Asp
465                 470                 475                 480

act cta aag gtt aaa gct tgg aag caa ggc tcg gtt gtc gtt ttt caa     1488
Thr Leu Lys Val Lys Ala Trp Lys Gln Gly Ser Val Val Val Phe Gln
                485                 490                 495

aca att gat acg acc aga aac gtc att gta ttg gat aac gcc gct gta     1536
Thr Ile Asp Thr Thr Arg Asn Val Ile Val Leu Asp Asn Ala Ala Val
            500                 505                 510

aaa cta tcg cag gca aaa tct aaa cta taa                             1566
Lys Leu Ser Gln Ala Lys Ser Lys Leu
        515                 520
```

-continued

<210> SEQ ID NO 5
<211> LENGTH: 521
<212> TYPE: PRT
<213> ORGANISM: Saccharomyces cerevisiae
<220> FEATURE:
<223> OTHER INFORMATION: Nucleotides 4-1566 of SEQ ID NO: 4 corresponds to nucleotides 1381-2943 of SEQ ID NO: 3.

<400> SEQUENCE: 5

```
Met Val Thr Glu Ala Pro Leu Ile Ile Gln Thr Ala Ile Ser Lys Phe
  1               5                  10                  15

Gln Arg Val Asp Ile Leu Val Asn Asn Ala Gly Ile Leu Arg Asp Lys
             20                  25                  30

Ser Phe Leu Lys Met Lys Asp Glu Glu Trp Phe Ala Val Leu Lys Val
         35                  40                  45

His Leu Phe Ser Thr Phe Ser Leu Ser Lys Ala Val Trp Pro Ile Phe
     50                  55                  60

Thr Lys Gln Lys Ser Gly Phe Ile Ile Asn Thr Thr Ser Thr Ser Gly
 65                  70                  75                  80

Ile Tyr Gly Asn Phe Gly Gln Ala Asn Tyr Ala Ala Ala Lys Ala Ala
                 85                  90                  95

Ile Leu Gly Phe Ser Lys Thr Ile Ala Leu Glu Gly Ala Lys Arg Gly
            100                 105                 110

Ile Ile Val Asn Val Ile Ala Pro His Ala Glu Thr Ala Met Thr Lys
        115                 120                 125

Thr Ile Phe Ser Glu Lys Glu Leu Ser Asn His Phe Asp Ala Ser Gln
    130                 135                 140

Val Ser Pro Leu Val Val Leu Leu Ala Ser Glu Glu Leu Gln Lys Tyr
145                 150                 155                 160

Ser Gly Arg Arg Val Ile Gly Gln Leu Phe Glu Val Gly Gly Gly Trp
                165                 170                 175

Cys Gly Gln Thr Arg Trp Gln Arg Ser Ser Gly Tyr Val Ser Ile Lys
            180                 185                 190

Glu Thr Ile Glu Pro Glu Glu Ile Lys Glu Asn Trp Asn His Ile Thr
        195                 200                 205

Asp Phe Ser Arg Asn Thr Ile Asn Pro Ser Ser Thr Glu Glu Ser Ser
    210                 215                 220

Met Ala Thr Leu Gln Ala Val Gln Lys Ala His Ser Ser Lys Glu Leu
225                 230                 235                 240

Asp Asp Gly Leu Phe Lys Tyr Thr Thr Lys Asp Cys Ile Leu Tyr Asn
                245                 250                 255

Leu Gly Leu Gly Cys Thr Ser Lys Glu Leu Lys Tyr Thr Tyr Glu Asn
            260                 265                 270

Asp Pro Asp Phe Gln Val Leu Pro Thr Phe Ala Val Ile Pro Phe Met
        275                 280                 285

Gln Ala Thr Ala Thr Leu Ala Met Asp Asn Leu Val Asp Asn Phe Asn
    290                 295                 300

Tyr Ala Met Leu Leu His Gly Glu Gln Tyr Phe Lys Leu Cys Thr Pro
305                 310                 315                 320

Thr Met Pro Ser Asn Gly Thr Leu Lys Thr Leu Ala Lys Pro Leu Gln
                325                 330                 335

Val Leu Asp Lys Asn Gly Lys Ala Ala Leu Val Val Gly Gly Phe Glu
            340                 345                 350

Thr Tyr Asp Ile Lys Thr Lys Lys Leu Ile Ala Tyr Asn Glu Gly Ser
        355                 360                 365
```

-continued

```
Phe Phe Ile Arg Gly Ala His Val Pro Pro Glu Lys Glu Val Arg Asp
    370                 375                 380

Gly Lys Arg Ala Lys Phe Ala Val Gln Asn Phe Glu Val Pro His Gly
385                 390                 395                 400

Lys Val Pro Asp Phe Glu Ala Glu Ile Ser Thr Asn Lys Asp Gln Ala
                405                 410                 415

Ala Leu Tyr Arg Leu Ser Gly Asp Phe Asn Pro Leu His Ile Asp Pro
            420                 425                 430

Thr Leu Ala Lys Ala Val Lys Phe Pro Thr Pro Ile Leu His Gly Leu
        435                 440                 445

Cys Thr Leu Gly Ile Ser Ala Lys Ala Leu Phe Glu His Tyr Gly Pro
    450                 455                 460

Tyr Glu Glu Leu Lys Val Arg Phe Thr Asn Val Val Phe Pro Gly Asp
465                 470                 475                 480

Thr Leu Lys Val Lys Ala Trp Lys Gln Gly Ser Val Val Val Phe Gln
                485                 490                 495

Thr Ile Asp Thr Thr Arg Asn Val Ile Val Leu Asp Asn Ala Ala Val
            500                 505                 510

Lys Leu Ser Gln Ala Lys Ser Lys Leu
        515                 520


<210> SEQ ID NO 6
<211> LENGTH: 1887
<212> TYPE: DNA
<213> ORGANISM: Saccharomyces cerevisiae
<220> FEATURE:
<221> NAME/KEY: CDS
<222> LOCATION: (1)..(1887)
<220> FEATURE:
<223> OTHER INFORMATION: Nucleotides 1-1887 of SEQ ID NO: 6  corresponds
      to nucleotides 241- 2127  of SEQ ID NO: 3.

<400> SEQUENCE: 6

atg cct gga aat tta tcc ttc aaa gat aga gtt gtt gta atc acg ggc       48
Met Pro Gly Asn Leu Ser Phe Lys Asp Arg Val Val Val Ile Thr Gly
  1               5                  10                  15

gct gga ggg ggc tta ggt aag gtg tat gca cta gct tac gca agc aga       96
Ala Gly Gly Gly Leu Gly Lys Val Tyr Ala Leu Ala Tyr Ala Ser Arg
             20                  25                  30

ggt gca aaa gtg gtc gtc aat gat cta ggt ggc act ttg ggt ggt tca      144
Gly Ala Lys Val Val Val Asn Asp Leu Gly Gly Thr Leu Gly Gly Ser
         35                  40                  45

gga cat aac tcc aaa gct gca gac tta gtg gtg gat gag ata aaa aaa      192
Gly His Asn Ser Lys Ala Ala Asp Leu Val Val Asp Glu Ile Lys Lys
     50                  55                  60

gcc gga ggt ata gct gtg gca aat tac gac tct gtt aat gaa aat gga      240
Ala Gly Gly Ile Ala Val Ala Asn Tyr Asp Ser Val Asn Glu Asn Gly
 65                  70                  75                  80

gag aaa ata att gaa acg gct ata aaa gaa ttc ggc agg gtt gat gta      288
Glu Lys Ile Ile Glu Thr Ala Ile Lys Glu Phe Gly Arg Val Asp Val
                 85                  90                  95

cta att aac aac gct gga ata tta agg gat gtt tca ttt gca aag atg      336
Leu Ile Asn Asn Ala Gly Ile Leu Arg Asp Val Ser Phe Ala Lys Met
            100                 105                 110

aca gaa cgt gag ttt gca tct gtg gta gat gtt cat ttg aca ggt ggc      384
Thr Glu Arg Glu Phe Ala Ser Val Val Asp Val His Leu Thr Gly Gly
        115                 120                 125

tat aag cta tcg cgt gct gct tgg cct tat atg cgc tct cag aaa ttt      432
Tyr Lys Leu Ser Arg Ala Ala Trp Pro Tyr Met Arg Ser Gln Lys Phe
    130                 135                 140
```

-continued

```
ggt aga atc att aac acc gct tcc cct gcc ggt cta ttt gga aat ttt      480
Gly Arg Ile Ile Asn Thr Ala Ser Pro Ala Gly Leu Phe Gly Asn Phe
145                 150                 155                 160

ggt caa gct aat tat tca gca gct aaa atg ggc tta gtt ggt ttg gcg      528
Gly Gln Ala Asn Tyr Ser Ala Ala Lys Met Gly Leu Val Gly Leu Ala
                165                 170                 175

gaa acc ctc gcg aag gag ggt gcc aaa tac aac att aat gtt aat tca      576
Glu Thr Leu Ala Lys Glu Gly Ala Lys Tyr Asn Ile Asn Val Asn Ser
            180                 185                 190

att gcg cca ttg gct aga tca cgt atg aca gaa aac gtg tta cca cca      624
Ile Ala Pro Leu Ala Arg Ser Arg Met Thr Glu Asn Val Leu Pro Pro
        195                 200                 205

cat atc ttg aaa cag tta gga ccg gaa aaa att gtt ccc tta gta ctc      672
His Ile Leu Lys Gln Leu Gly Pro Glu Lys Ile Val Pro Leu Val Leu
    210                 215                 220

tat ttg aca cac gaa agt acg aaa gtg tca aac tcc att ttt gaa ctc      720
Tyr Leu Thr His Glu Ser Thr Lys Val Ser Asn Ser Ile Phe Glu Leu
225                 230                 235                 240

gct gct gga ttc ttt gga cag ctc aga tgg gag agg tct tct gga caa      768
Ala Ala Gly Phe Phe Gly Gln Leu Arg Trp Glu Arg Ser Ser Gly Gln
                245                 250                 255

att ttc aat cca gac ccc aag aca tat act cct gaa gca att tta aat      816
Ile Phe Asn Pro Asp Pro Lys Thr Tyr Thr Pro Glu Ala Ile Leu Asn
            260                 265                 270

aag tgg aag gaa atc aca gac tat agg gac aag cca ttt aac aaa act      864
Lys Trp Lys Glu Ile Thr Asp Tyr Arg Asp Lys Pro Phe Asn Lys Thr
        275                 280                 285

cag cat cca tat caa ctc tcg gat tat aat gat tta atc acc aaa gca      912
Gln His Pro Tyr Gln Leu Ser Asp Tyr Asn Asp Leu Ile Thr Lys Ala
    290                 295                 300

aaa aaa tta cct ccc aat gaa caa ggc tca gtg aaa atc aag tcg ctt      960
Lys Lys Leu Pro Pro Asn Glu Gln Gly Ser Val Lys Ile Lys Ser Leu
305                 310                 315                 320

tgc aac aaa gtc gta gta gtt acg ggt gca gga ggt ggt ctt ggg aag     1008
Cys Asn Lys Val Val Val Val Thr Gly Ala Gly Gly Gly Leu Gly Lys
                325                 330                 335

tct cat gca atc tgg ttt gca cgg tac ggt gcg aag gta gtt gta aat     1056
Ser His Ala Ile Trp Phe Ala Arg Tyr Gly Ala Lys Val Val Val Asn
            340                 345                 350

gac atc aag gat cct ttt tca gtt gtt gaa gaa ata aat aaa cta tat     1104
Asp Ile Lys Asp Pro Phe Ser Val Val Glu Glu Ile Asn Lys Leu Tyr
        355                 360                 365

ggt gaa ggc aca gcc att cca gat tcc cat gat gtg gtc acc gaa gct     1152
Gly Glu Gly Thr Ala Ile Pro Asp Ser His Asp Val Val Thr Glu Ala
    370                 375                 380

cct ctc att atc caa act gca ata agt aag ttt cag aga gta gac atc     1200
Pro Leu Ile Ile Gln Thr Ala Ile Ser Lys Phe Gln Arg Val Asp Ile
385                 390                 395                 400

ttg gtc aat aac gct ggt att ttg cgt gac aaa tct ttt tta aaa atg     1248
Leu Val Asn Asn Ala Gly Ile Leu Arg Asp Lys Ser Phe Leu Lys Met
                405                 410                 415

aaa gat gag gaa tgg ttt gct gtc ctg aaa gtc cac ctt ttt tcc aca     1296
Lys Asp Glu Glu Trp Phe Ala Val Leu Lys Val His Leu Phe Ser Thr
            420                 425                 430

ttt tca ttg tca aaa gca gta tgg cca ata ttt acc aaa caa aag tct     1344
Phe Ser Leu Ser Lys Ala Val Trp Pro Ile Phe Thr Lys Gln Lys Ser
        435                 440                 445

gga ttt att atc aat act act tct acc tca gga att tat ggt aat ttt     1392
Gly Phe Ile Ile Asn Thr Thr Ser Thr Ser Gly Ile Tyr Gly Asn Phe
```

```
    450                 455                 460

gga cag gcc aat tat gcc gct gca aaa gcc gcc att tta gga ttc agt     1440
Gly Gln Ala Asn Tyr Ala Ala Ala Lys Ala Ala Ile Leu Gly Phe Ser
465                 470                 475                 480

aaa act att gca ctg gaa ggt gcc aag aga gga att att gtt aat gtt     1488
Lys Thr Ile Ala Leu Glu Gly Ala Lys Arg Gly Ile Ile Val Asn Val
                485                 490                 495

atc gct cct cat gca gaa acg gct atg aca aag act ata ttc tcg gag     1536
Ile Ala Pro His Ala Glu Thr Ala Met Thr Lys Thr Ile Phe Ser Glu
            500                 505                 510

aag gaa tta tca aac cac ttt gat gca tct caa gtc tcc cca ctt gtt     1584
Lys Glu Leu Ser Asn His Phe Asp Ala Ser Gln Val Ser Pro Leu Val
        515                 520                 525

gtt ttg ttg gca tct gaa gaa cta caa aag tat tct gga aga agg gtt     1632
Val Leu Leu Ala Ser Glu Glu Leu Gln Lys Tyr Ser Gly Arg Arg Val
    530                 535                 540

att ggc caa tta ttc gaa gtt ggc ggt ggt tgg tgt ggg caa acc aga     1680
Ile Gly Gln Leu Phe Glu Val Gly Gly Gly Trp Cys Gly Gln Thr Arg
545                 550                 555                 560

tgg caa aga agt tcc ggt tat gtt tct att aaa gag act att gaa ccg     1728
Trp Gln Arg Ser Ser Gly Tyr Val Ser Ile Lys Glu Thr Ile Glu Pro
                565                 570                 575

gaa gaa att aaa gaa aat tgg aac cac atc act gat ttc agt cgc aac     1776
Glu Glu Ile Lys Glu Asn Trp Asn His Ile Thr Asp Phe Ser Arg Asn
            580                 585                 590

act atc aac ccg agc tcc aca gag gag tct tct atg gca acc ttg caa     1824
Thr Ile Asn Pro Ser Ser Thr Glu Glu Ser Ser Met Ala Thr Leu Gln
        595                 600                 605

gcc gtg caa aaa gcg cac tct tca aag gag ttg gat gat gga tta ttc     1872
Ala Val Gln Lys Ala His Ser Ser Lys Glu Leu Asp Asp Gly Leu Phe
    610                 615                 620

aag tac act acc aag                                                 1887
Lys Tyr Thr Thr Lys
625


<210> SEQ ID NO 7
<211> LENGTH: 629
<212> TYPE: PRT
<213> ORGANISM: Saccharomyces cerevisiae
<220> FEATURE:
<223> OTHER INFORMATION: Nucleotides 1-1887 of SEQ ID NO: 6  corresponds
      to nucleotides 241- 2127  of SEQ ID NO: 3.

<400> SEQUENCE: 7

Met Pro Gly Asn Leu Ser Phe Lys Asp Arg Val Val Val Ile Thr Gly
  1               5                  10                  15

Ala Gly Gly Gly Leu Gly Lys Val Tyr Ala Leu Ala Tyr Ala Ser Arg
             20                  25                  30

Gly Ala Lys Val Val Val Asn Asp Leu Gly Gly Thr Leu Gly Gly Ser
         35                  40                  45

Gly His Asn Ser Lys Ala Ala Asp Leu Val Val Asp Glu Ile Lys Lys
     50                  55                  60

Ala Gly Gly Ile Ala Val Ala Asn Tyr Asp Ser Val Asn Glu Asn Gly
 65                  70                  75                  80

Glu Lys Ile Ile Glu Thr Ala Ile Lys Glu Phe Gly Arg Val Asp Val
                 85                  90                  95

Leu Ile Asn Asn Ala Gly Ile Leu Arg Asp Val Ser Phe Ala Lys Met
            100                 105                 110

Thr Glu Arg Glu Phe Ala Ser Val Val Asp Val His Leu Thr Gly Gly
```

-continued

```
        115                 120                 125

Tyr Lys Leu Ser Arg Ala Ala Trp Pro Tyr Met Arg Ser Gln Lys Phe
    130                 135                 140

Gly Arg Ile Ile Asn Thr Ala Ser Pro Ala Gly Leu Phe Gly Asn Phe
145                 150                 155                 160

Gly Gln Ala Asn Tyr Ser Ala Ala Lys Met Gly Leu Val Gly Leu Ala
                165                 170                 175

Glu Thr Leu Ala Lys Glu Gly Ala Lys Tyr Asn Ile Asn Val Asn Ser
            180                 185                 190

Ile Ala Pro Leu Ala Arg Ser Arg Met Thr Glu Asn Val Leu Pro Pro
        195                 200                 205

His Ile Leu Lys Gln Leu Gly Pro Glu Lys Ile Val Pro Leu Val Leu
    210                 215                 220

Tyr Leu Thr His Glu Ser Thr Lys Val Ser Asn Ser Ile Phe Glu Leu
225                 230                 235                 240

Ala Ala Gly Phe Phe Gly Gln Leu Arg Trp Glu Arg Ser Ser Gly Gln
                245                 250                 255

Ile Phe Asn Pro Asp Pro Lys Thr Tyr Thr Pro Glu Ala Ile Leu Asn
            260                 265                 270

Lys Trp Lys Glu Ile Thr Asp Tyr Arg Asp Lys Pro Phe Asn Lys Thr
        275                 280                 285

Gln His Pro Tyr Gln Leu Ser Asp Tyr Asn Asp Leu Ile Thr Lys Ala
    290                 295                 300

Lys Lys Leu Pro Pro Asn Glu Gln Gly Ser Val Lys Ile Lys Ser Leu
305                 310                 315                 320

Cys Asn Lys Val Val Val Val Thr Gly Ala Gly Gly Gly Leu Gly Lys
                325                 330                 335

Ser His Ala Ile Trp Phe Ala Arg Tyr Gly Ala Lys Val Val Val Asn
            340                 345                 350

Asp Ile Lys Asp Pro Phe Ser Val Val Glu Glu Ile Asn Lys Leu Tyr
        355                 360                 365

Gly Glu Gly Thr Ala Ile Pro Asp Ser His Asp Val Val Thr Glu Ala
    370                 375                 380

Pro Leu Ile Ile Gln Thr Ala Ile Ser Lys Phe Gln Arg Val Asp Ile
385                 390                 395                 400

Leu Val Asn Asn Ala Gly Ile Leu Arg Asp Lys Ser Phe Leu Lys Met
                405                 410                 415

Lys Asp Glu Glu Trp Phe Ala Val Leu Lys Val His Leu Phe Ser Thr
            420                 425                 430

Phe Ser Leu Ser Lys Ala Val Trp Pro Ile Phe Thr Lys Gln Lys Ser
        435                 440                 445

Gly Phe Ile Ile Asn Thr Thr Ser Thr Ser Gly Ile Tyr Gly Asn Phe
    450                 455                 460

Gly Gln Ala Asn Tyr Ala Ala Ala Lys Ala Ala Ile Leu Gly Phe Ser
465                 470                 475                 480

Lys Thr Ile Ala Leu Glu Gly Ala Lys Arg Gly Ile Ile Val Asn Val
                485                 490                 495

Ile Ala Pro His Ala Glu Thr Ala Met Thr Lys Thr Ile Phe Ser Glu
            500                 505                 510

Lys Glu Leu Ser Asn His Phe Asp Ala Ser Gln Val Ser Pro Leu Val
        515                 520                 525

Val Leu Leu Ala Ser Glu Glu Leu Gln Lys Tyr Ser Gly Arg Arg Val
    530                 535                 540
```

```
Ile Gly Gln Leu Phe Glu Val Gly Gly Gly Trp Cys Gly Gln Thr Arg
545                 550                 555                 560

Trp Gln Arg Ser Ser Gly Tyr Val Ser Ile Lys Glu Thr Ile Glu Pro
                565                 570                 575

Glu Glu Ile Lys Glu Asn Trp Asn His Ile Thr Asp Phe Ser Arg Asn
            580                 585                 590

Thr Ile Asn Pro Ser Ser Thr Glu Glu Ser Ser Met Ala Thr Leu Gln
        595                 600                 605

Ala Val Gln Lys Ala His Ser Ser Lys Glu Leu Asp Asp Gly Leu Phe
    610                 615                 620

Lys Tyr Thr Thr Lys
625


<210> SEQ ID NO 8
<211> LENGTH: 6455
<212> TYPE: DNA
<213> ORGANISM: Pseudomonas oleovorans

<400> SEQUENCE: 8

gaattcctgc gcgtgcactc cccctccgcc gaggtccagg gccacggtaa ccccatcctg      60

cagttcggca agatcaacgt cggcctcagc ggcctggaac ctgccgggca atacgcactg     120

aaactgacct tcgacgacgg ccatgacagc ggcctgttca cctgggaata cctcgagcag     180

ctgtgcctgc gccaggaaca gctgtgggcc gagtacctcg acgaactgca caaggccggg     240

aaatcccgcg accctgccga gtcggtggtc aaactcatgc tctagcgcaa ggcctgcagg     300

atttagagcg cattttctaa aatcatctgt ttgaatgact tacagacagc ccagtgacgg     360

gctgtcttgc gcattacatg aaagtcgggt aaccaatggg ggtggcaagt tccctgcatc     420

aaattgcagg tagtcagaac cctcgcagca ccgctgttcc ttatcactgg tcacccgagt     480

agcagtaccg ggctcagaac tgtgcacccg ccacagcaac cggtactcgt ctcaggacaa     540

cggagcgtcg tagatgagta acaagaacaa cgatgagctg cagcggcagg cctcggaaaa     600

caccctgggg ctgaacccgg tcatcggtat ccgccgcaaa gacctgttga gctcggcacg     660

caccgtgctg cgccaggccg tgcgccaacc gctgcacagc gccaagcatg tggcccactt     720

tggcctggag ctgaagaacg tgctgctggg caagtccagc cttgccccgg aaagcgacga     780

ccgtcgcttc aatgacccgg catggagcaa caacccactt taccgccgct acctgcaaac     840

ctatctggcc tggcgcaagg agctgcagga ctggatcggc aacagcgacc tgtcgcccca     900

ggacatcagc cgcggccagt tcgtcatcaa cctgatgacc gaagccatgg ctccgaccaa     960

caccctgtcc aacccggcag cagtcaaacg cttcttcgaa accggcggca agagcctgct    1020

cgatggcctg tccaacctgg ccaaggacct ggtcaacaac ggtggcatgc ccagccaggt    1080

gaacatggac gccttcgagg tgggcaagaa cctgggcacc agtgaaggcg ccgtggtgta    1140

ccgcaacgat gtgctggagc tgatccagta caagcccatc accgagcagg tgcatgcccg    1200

cccgctgctg gtggtgccgc cgcagatcaa caagttctac gtattcgacc tgagcccgga    1260

aaagagcctg gcacgctact gcctgcgctc gcagcagcag accttcatca tcagctggcg    1320

caacccgacc aaagcccagc gcgaatgggg cctgtccacc tacatcgacg cgctcaagga    1380

ggcggtcgac gcggtgctgg cgattaccgg cagcaaggac ctgaacatgc tcggtgcctg    1440

ctccggcggc atcacctgca cggcattggt cggccactat gccgccctcg gcgaaaacaa    1500

ggtcaatgcc ctgaccctgc tggtcagcgt gctggacacc accatggaca accaggtcgc    1560
```

-continued

```
cctgttcgtc gacgagcaga ctttggaggc cgccaagcgc cactcctacc aggccggtgt   1620
gctcgaaggc agcgagatgg ccaaggtgtt cgcctggatg cgccccaacg acctgatctg   1680
gaactactgg gtcaacaact acctgctcgg caacgagccg ccggtgttcg acatcctgtt   1740
ctggaacaac gacaccacgc gcctgccggc cgccttccac ggcgacctga tcgaaatgtt   1800
caagagcaac ccgctgaccc gcccggacgc cctggaggtt tgcggcactc cgatcgacct   1860
gaaacaggtc aaatgcgaca tctacagcct tgccggcacc aacgaccaca tcaccccgtg   1920
gcagtcatgc taccgctcgg cgcacctgtt cggcggcaag atcgagttcg tgctgtccaa   1980
cagcggccac atccagagca tcctcaaccc gccaggcaac cccaaggcgc gcttcatgac   2040
cggtgccgat cgcccgggtg acccggtggc ctggcaggaa aacgccacca agcatgccga   2100
ctcctggtgg ctgcactggc aaagctggct gggcgagcgt gccggcgagc tggaaaaggc   2160
gccgacccgc ctgggcaacc gtgcctatgc cgctggcgag gcatccccgg gcacctacgt   2220
tcacgagcgt tgagctgcag cgccgtggcc acctgcggga cgccacggtg ttcatttcac   2280
cccatgagtc acgcgcatgc cgcaacccta catcttcagg accgtcgagc tggacaacca   2340
gtccatccgc accgccgtcc gcccgggcaa accgcacctg acgccgttgc tgatcttcaa   2400
cggcatcggt gccaacctgg agctggtgtt tccgttcatc gaggcactgg acccggacct   2460
ggaagtcatt gcctttgacg tacccggggt cggcggctcg tccacgccgc gccacccata   2520
ccgcttcccc gggttggcca agctgacggc acgcatgctc gactacctcg actacggcca   2580
ggtcaatgtc atcggtgtgt cttggggcgg cgccctggcc cagcagttcg cccacgatta   2640
ccccgaacgc tgcaagaaac tggtgctggc cgccaccgca gccggtgcgg tgatggtgcc   2700
aggcaagccc aaggtgttgt ggatgatggc cagcccacgg cgttacgtgc agccgtcgca   2760
tgtcatccgc attgcgccga cgatctatgg cggcggcttc cggcgtgacc ccgaactggc   2820
catgcagcac gcctccaagg tgcgctccgg cggcaagatg ggctactact ggcagctgtt   2880
cgccgggctc ggctggacca gcatccactg gctgcacaag atccagcaac cgaccctggt   2940
gctggccggc gacgacgacc cgctgatccc gctgatcaac atgcgcctgc tggcctggcg   3000
gattcccaat gcccagctac acattatcga cgacggtcat ttgttcctga tcacccgggc   3060
cgaggccgtc gccccgatca tcatgaagtt ccttcagcaa gaacgacagc gcgccgtcat   3120
gcaccctcgc ccggcttcgg gcgggtaaat cgatgcggcc ttcttcgcgg gcgcgcccgc   3180
tcccacaggg atggcgccga acctgtggga gcgggcatgc ccgcgaaggt ctcgacagcg   3240
aaatggctta gacgagggag tgttgccatg aaagacaaac cggccaaagg aacgccaacg   3300
cttcccgcca ccagcatgaa cgtgcagaac gccatcctcg gcctgcgcgg tcgtgacctg   3360
atttccacgc tgcgcaatgt cagccgccaa agcctgcgtc acccgctgca caccgcacat   3420
cacctgttgg ccctgggtgg ccagctgggc cgggtgatac tgggtgacac accgcttcag   3480
ccgaacccgc gcgatccgcg cttcagcgac ccgacatgga gccagaaccc gttctaccgg   3540
cgcggcctgc aagcctacct ggcctggcag aagcagaccc gcctgtggat cgaggaaagc   3600
cacctggacg acgatgaccg ggcccgtgcg cacttcctgt tcaacctgat caacgatgcc   3660
ctggcgccaa gcaactcgct gctcaacccg ctggcggtca aggaactgtt caacagcggt   3720
ggccagagcc tggtgcgcgg cgtggcccac ctgctcgatg acctgcgcca caatgacggc   3780
ctgccacgcc aggtcgacga gcgcgccttc gaagtgggcg gcaacctggc cgcgactgcc   3840
ggcgccgtgg tgtttcgcaa cgagctgctg gaactgatcc agtacaagcc gatgagcgaa   3900
aagcagcacg cccggccact gctggtggtg ccgccacaga tcaacaagtt ctacatcttc   3960
```

-continued

```
gacctcagct cgaccaacag cttcgtccag tacatgctca agaatggcct gcaggtgttc   4020
atggtcagct ggcgcaaccc cgacccgcgc caccgcgaat ggggcctgtc cagctacgtg   4080
caggccctgg aagaagcgct caacgcttgc cgcagcatta gcggcaaccg cgaccccaac   4140
ctgatgggcg cctgcgccgg cggcctgacc atggccgcac tgcagggcca cctgcaggcc   4200
aagcaccagc tgcgccgggt gcgcagcgcc acctacctgg tcagcttgct ggacagcaag   4260
ttcgaaagcc ccgccagcct gttcgccgac gagcagacca tcgaggccgc caagcgccgc   4320
tcctaccagc gcggtgtgct ggatggcgcc gaggtggcgc ggatcttcgc ctggatgcgg   4380
cccaacgacc tgatctggaa ctactgggtc aacaactacc tgctcggcaa gacaccacca   4440
gccttcgaca tcctgtactg gaacgccgac agcacgcgcc tgcccgccgc gctgcatggc   4500
gacctgctgg acttcttcaa gctcaacccg ctgacccacc cagccggcct ggaggtatgc   4560
ggcacaccca tcgacctgca gaaggtcgag ctggacagtt tcaccgtggc cggcagcaac   4620
gaccacatca ccccgtggga tgcggtgtac cgctcggcct tgctgctggg tggcgaccgg   4680
cgcttcgtgc tggccaacag cgggcacatc cagagcatca tcaacccgcc cggcaacccc   4740
aaggcctact acctggccaa ccccaagctg tccagcgacc cgcgtgcctg gctccacgat   4800
gccaagcgca gcgaaggcag ctggtggccg ttgtggctgg agtggatcac cgcgcgctcc   4860
ggcccgctca aggcaccgcg cagcgaactg ggcaatgcca cctacccacc gctgggcccc   4920
gcgccgggca cctacgtgct gacccgatga gcatgccgac tggatgaaga ctcgcgaccg   4980
tatcctcgaa tgtgccctgc agctgttcaa ccagcagggc gaaccgaacg tatccaccct   5040
ggaaattgcc aacgaactgg gcatcagccc tggcaacctc tactaccact tccacggcaa   5100
ggagccgttg gtgctggggt tgttcgagcg ctttgaagaa gcgctgatgc ccttgctcga   5160
cccgccgctg gaggtacgcc tggacgccga ggattactgg ctgttcctgc acctgatcgt   5220
cgaacgcatg gcgcagtacc gcttcctgtt ccaggacctg tcgaacctga ccgggcgcct   5280
gcccaaactg gcccgcggca tgcgcaacct gatcaacgcg ctcaagcgca cactggcggc   5340
gttgctggcc agcctcaagg gccaagggtt ggtagagagc gagacccagg cgctggggca   5400
actggtggag cagatcaccc tgacactgat gttctcgctg gattatcagc gggtactggg   5460
gcgcgagggg gatgtgggga ttgtggtgta ccaggtgatg atgctggtgg cgccgcatct   5520
gcaggcccag gcgcgggggg cggcggagca attggcggtg cggtatctgg aggggtaagc   5580
ctgttgattc ggtgtcgcgg ctttcgcggg catgcccgct cccacaggtg aaatgcagtg   5640
ctcgagtgca cacaggacct gtgggagcgg gcaagcccgc gaagatggcg acgcggtatc   5700
agatcagggt accggtgcct gtctgtgccg aaggcgggtt gctggccgga gccgcagtgg   5760
gcgccgaagc tgcgctagcg gccggagcgg cgctggccgc tggagctgcc ggcttggcgg   5820
ctgccggctt ggccggtgct ttcttcactg caggcttctt cgccacagcc ggtttggccg   5880
ctgccggttt gccgcaggct tggccgccgc agtcttggca gcaggtttag ccgctgcggc   5940
cttggctgcc ggcttggctg ccgcggtttt gccgcaggct tggccgctgc cgtcttggcc   6000
agtggcttgg ccgccgcctt gctcgcagcc ggtttggctg cagtgcgcga cgaaatcggg   6060
gtaaccgaag cgccggtgag tttctcgatc tgcttggtca ggctgtccac ctgctggtgc   6120
agggccttga tctcgttgcg gctcggcacg ccaaggcgcg agatggcact gttcaggcgc   6180
ttgtcgaagg cctcttcgag ttcgctccac ttgcctagcg cacggtcctt cacgcccgac   6240
acacgcgaag tggtcgacga cttggcagtt tcagcaacat cttctgcggt cttcttcgcc   6300
```

-continued

```
tgtttctcgg ccttctcgcc atcctttacc agcgagtcga acagcttcgg gccgtcctgg   6360

tcgatcttcg aatagatacc aagccccgcc agccagatct tgcgggagta cttctcgatc   6420

ccgccgccca ggagctgcct tctttctcgg aattc                              6455
```

<210> SEQ ID NO 9
<211> LENGTH: 5054
<212> TYPE: DNA
<213> ORGANISM: Pseudomonas putida

<400> SEQUENCE: 9

```
ctgcagtcga cctcgccttg ccagtgggcg gcgagcatca ggccctcttc atcgggcagg     60

atgaaaacct gcaaggccgg ctggcggcag tcgatctcga tgaccttgcc ctccagcgcg    120

gccagccgcg gcagggccgt gctgtccatg cgcaggacgc ggttcaggcc atgttcggcg    180

ctggcgagca gcccggccag cagcatcagg gcttgatccc ccgatgcacg gcaacgatgc    240

cgctggtcat gttgtggtag gtgacccggt cgaaaccggc ctcgaccatc atggccttca    300

gggtttcctg atcggggtgc atgcggatcg actcggcgag gtaacggtag ctctccgaat    360

cgttggtgat cagcttgccg gccagcggca tgaaggcgaa cgagtaggcg tcgtaggcct    420

tggacatcag cttgttggtc ggcttggaga actccagcac cagcaggcga ccgcctggct    480

tgagcacgcg cagcatcgag cggatggctt cgtccttgtg ggtgacgttg cgcaggccga    540

aggcgatggt cacgcagtcg aagtggttgt ccgggaatgg cagcttctcg gcgtcggcct    600

gaacgaactc gatgttgccg gccacgccac ggtcgagcag gcggtcacga ccgaccttga    660

gcatcgattc gttgatgtcg gccagcacta cctgaccggt cgggccgacc agccgcgaga    720

acttggcggc caggtcgccg gtaccgccgg cgatgtccag tacacgattg ccggcgcgta    780

cgcccgacag ctcgatggtg aagcgcttcc acaggcggtg catgccgccg gaaagcacat    840

cgttcatcag gtcgtacttg gccgctaccg agtggaacac ctcggcgact ttcttcgcct    900

tctggctttc agggacgtcc tggtaaccga aatgggtggt gggttcggcg tggtcgcctt    960

tgcgctggtc gttcatatcg cttcaccgga aaaaattacc gccattctag ggcgaacggg   1020

cagatttgtc ttggcggggt gtgccagtgg gcaggggcgg gcataatgcc cattatgtct   1080

tcatcttcag gaacacccgc atgacccaga tcagcgtcga acgcaaacat tccctcggcc   1140

gcgatgccgc ccgtgccaag gctgaagcgc tggtcgacaa actgacccgc gaatacgacc   1200

tcaaggccac ctggaacggc gacagggtcg acgtggcgcg cagcggtgcc aacggcagcg   1260

tgcacatctt cgatgaccgc atccgcgtcg aattgaagct gggcatgatg ctgtcgatga   1320

tgagcggcac catcaagggc gagatcgagc gggcgctgga caaagccctg gcctgacccc   1380

ttccgggggc catgctcgtt caccttaggg tgaagattct aatttccctc tctaccttgt   1440

gctcaagccc aacctccatg ggcggtttat cctccactca tgagcatgag gtacagagca   1500

tggccaaagt gactgtgaag aaaaaggacg acgccccggg cacgctgggc gaggtgcgcg   1560

gctacgcgcg caagatctgg ctggcgggca tcggcgccta tgcgcgtgtg ggccaggaag   1620

gctccgacta cttcaatgag ctggtcaagg ccggcgaagg cgtcgagaag cgtggcaaga   1680

agcgcatcga caaggagctc gatgctgcca acaatcagat cgaagaagcg acccaggaag   1740

tcagtcgcgt acgcggcaag gtcgaagttc aactggacaa gatcgaaaaa gctttcgacg   1800

cgcgggtagg tcgcgccttg aatcgccttg gcattccgtc taaacatgac gttgaggcgt   1860

tgtccatcaa gcttgaacag ctgcacgagc tgctcgagcg cgtcgcgcac aaaccataag   1920

gagagcagga tggctggcaa gaagaattcc gagaaagaag gcagctcctg ggtcggcggg   1980
```

```
atcgagaagt actcccgcaa gatctggctg gcggggcttg gtatctattc gaagatcgac   2040
caggacggcc cgaagctgtt cgactcgctg gtgaaggatg gcgagaaggc cgagaagcag   2100
gcgaagaaga ccgccgaaga tgttgctgaa actgccaagt cgtcgaccac ttcgcgtgtg   2160
tcgggcgtga aggaccgtgc gctgggcaag tggagcgaac tcgaagaggc cttcgacaag   2220
cgcctgaaca gcgccatctc gcgccttggc gtgccgagcc gcaacgagat caaggccctg   2280
caccagcagg tggacagcct gaccaagcag atcgagaaac ttaccggcgc ttcgcttacc   2340
ccgatttcgt cgcgcgctgc ggccaaaccg gctgcgagca aggcggcggc caagccactg   2400
gccaagacgg cagcggccaa gcctgcggcg aaaactgcgg cggccaagcc ggcggccaag   2460
actgctgcgg cgaaacctgc tgccaagact gcagcggcca agcctgcggc gaaaccggca   2520
gcggccaagc cggctgtggc gaagaagccg gcagtgaaga aagcaccggc caagccagca   2580
gccgccaagc cggcagctcc agcggcgagc gccgctccga ccgctagcgc agctcctgca   2640
ccaaccgcgg ctccggccag caatccgcct tcggcaccga caggcaccgg taccctgatc   2700
tgataccgcg tcgccttctt cgcgggcttg cccgctccca caggtcctgt gtgcactcga   2760
gcactgcatt tcacctgtgg gagcgggcat gcccgcgaaa gccgcgacac cgaaacaaca   2820
ggcttacccc tccagatacc tcaccgccaa ctgctccgcc gcccccgcg cctgggcctg    2880
cagatgcggc gccaccagca tcatcacctg gtacaccaca atccccacat ccccctcgcg   2940
ccccagtacc cgctggtaat ccagcgagaa catcagtgtc agggtgatct gctccaccag   3000
ttgccccagc gcctgggtct cgctctctac cagcccctgg cccttgaggc tggccagcaa   3060
cgccgccagt gtgcgcttga gtgcgttgat caggctgcgc atgccgcggg ccagtttggg   3120
caggcgcccg gtcaggttcg acaggtcctg gaacaggaag cggtactgcg ccatgcgttc   3180
gacgatcagg tgcaggaaca gccagtaatc ctcggcatcc aggcgtacct ccagtggcgg   3240
gtcgagcaag ggcattagcg cttcttcaaa gcgctcgaac agccccagca ccaacggctc   3300
cttgccgtgg aagtggtagt agaggttgcc ggggctgatg cccagttcgt tggcaatttc   3360
cagggtggat acgttcggtt cgccctgctg gttgaacagc tgcagggcac attccaggat   3420
acggtcgcga gtcttcatcc agtcggcatg ctcatcgggt cagcacgtag gtgcccggcg   3480
cagggcccag cggtgggtag gtggcattgc ccagttcgct gcgtggtgcc ttgagcgggc   3540
cggagcgtgg tgtgatccac tccagccaca acggccacca gctgccttcg ctgcgcttgg   3600
cgtcgtggaa ccaggcacgg gggtcgctgg acagcttggg gttggccagg taataggcct   3660
tggggttgcc gggcgggttg atgatgctct ggatgtgccc gctgttggcc agcacgaagc   3720
gacggtcgcc gcccagcagc aaggccgagc ggtacaccgc atcccacggg gtgatgtggt   3780
cgttgctgcc ggccacggtg aaactgtcca gatcgacctt ctgcaggtcg atgggggtgc   3840
cgcatacctc caggccggct gggtgagtca gcgggttgag cttgaagaag tccagcaggt   3900
cgccatgcag cgcggcgggc aggcgcgtgc tgtcggcgtt ccagtacagg atgtcgaaag   3960
ctggtggtgt cttgccgagc aggtagttgt tgacccagta gttccagatc aggtcgttgg   4020
gccgcatcca ggcgaagatc cgcgccacct cggcgccatc cagcacgcct cgttggtagg   4080
agcggcgctt ggcggcttcg atggtctgct cgtcggcgaa caggctggcg gggctttcga   4140
acttgctgtc cagaaggctg accaggtagg tggcgctgcg cacccgacgc agctggtgct   4200
tggcctgcag gtgaccctgt agcgcggcca tggtcaggcc gccggcgcag gcccccatca   4260
ggttggggtc gcggttgccg ctgatgctgc ggcaagcgtt gagcgcttct tccagggcct   4320
```

-continued

```
gcacgtagct cgacaggccc cattcgcggt ggcgcgggtc ggggttgcgc cagctcacca   4380

tgaacacctg caggccattc ttgagcatgt actggacgaa gctgttggtc gagctgaggt   4440

cgaagatgta gaacttgttg atctgtggcg gcactaccag cagtggccgg gcgtgctgct   4500

tttcgctcat cggcttgtac tggatcagct ccagcagctc gttgcgaaac accacggcgc   4560

cggcggttgc agccaggttg ccgcccactt cgaaggcgcg ctcgtcgacc tggcgtggta   4620

ggccatcgtt gtggcgcagg tcatcgagca ggtgggccac gccgcgtacc aggctctggc   4680

caccgctgtt gaacagttcc ttgaccgcca gcgggttgag cagcgagttg ctcggcgcca   4740

gtgcatcgtt gatcaggttg aacaggaagt gcgcacgggc ccggtcatcg tcgtccaggt   4800

ggctttcctc gatccacagg cgggtctgct tctgccaggc caggtaggct tgcaggccgc   4860

gccggtagaa cgggttctgg ctccatgtcg ggtcgctgaa gcgcggatcg cgcgggttcg   4920

gctgaaacgg tgtgtcaccc agcatcaccc tgcccagctg accacccagg gccaacaggt   4980

gatgcgcggt gtgcagcggg tgacgcaggc tttggcggct gacattgcgc agcgtggaaa   5040

tcaggtcacg gccg                                                     5054
```

<210> SEQ ID NO 10
<211> LENGTH: 7311
<212> TYPE: DNA
<213> ORGANISM: Pseudomonas aeruginosa

<400> SEQUENCE: 10

```
ctgcagggcc gcctgccgat ccgcgtggag ctcaaggccc tcagtccgaa cgatttcgag     60

cgcatcctca ccgagccgca tgcctcgctc accgagcagt accgcgagct gctgaagacc    120

gaggggctgg ccatcgagtt cgccgaggac ggcatcaagc gccttgccga gatcgcctgg    180

caggtcaacg agaagaccga gaacatcggt gcccgccgcc tgcatacgct gctcgagcgg    240

ctgctggaag aggtctcgtt cagcgccgcc gacctggcca gcgagcatag cgacaagccg    300

atcctgatcg atgccggcta cgtcaacagc cacctcggcg agctggccga ggacgaggac    360

ctgtcccgct acatcctttg accaccgccg ccgccacggc caacaccgtg gcggcgggcc    420

gcgcggtccc gaaccggggt atccttgtac tccgcccttc cgcgagtccg atgcgatgcg    480

tatcccttcc gccatccagc tgcacaaagc ctcgaagacc ctgaccctgc gctacggcga    540

ggatagctac gacctgcctg ccgagttcct ccgcgtgcat tcgccctcgg ccgaggtcca    600

gggccacggc aacccggtat tgcagtacgg caagctgaac gtcggcctgg tcggcgtcga    660

acccgccggc cagtacgcac tgaagctgag cttcgacgac ggccacgaca gcggcctgtt    720

cacctgggac tacctgtacg agctggcgac ccgcaaggac cagctatggg ccgactacct    780

ggcggagctg gccagcgccg gcaagtcgcg cgaccccgac gagtcggtcg tcaagctgat    840

gctctgaagc gccgggccga gtgccccttc gcggcacacg gcatccaggc gatttttctc    900

cgctgccccg aacgagggca cgtcatttgc aacattcgcc ccgcagactg ccagaccaga    960

catccggtcg gcgcggtcgc cacggcgaat gtcctaccct gcacggcagc aacgctctag   1020

tccgcaggtc ggccgctcgc cgggccagcc acgccggcca ccgatgcttc tgccagcttg   1080

cacgccagcg gaaactcgcg taaccaagac ggtgcagccc cttgtccggg ttcccttccc   1140

tgacgtgcgt ccgccccgcc ctgaaacgtg cgggtgggct ggtagtcgag cagtagccgg   1200

ccggacacct agtccccggt ttcgttgcgg tcccctgttt cgcctcgaac aatggagcgt   1260

tgccgatgag tcagaagaac aataacgagc ttcccaagca agccgcggaa aacacgctga   1320

acctgaatcc ggtgatcggc atccggggca aggacctgct cacctccgcg cgcatggtcc   1380
```

-continued

```
tgctccaggc ggtgcgccag ccgctgcaca gcgccaggca cgtggcgcat ttcagcctgg   1440
agctgaagaa cgtcctgctc ggccagtcgg agctacgccc aggcgatgac gaccgacgct   1500
tttccgatcc ggcctggagc cagaatccac tgtacaagcg ctacatgcag acctacctgg   1560
cctggcgcaa ggagctgcac agctggatca gccacagcga cctgtcgccg caggacatca   1620
gtcgtggcca gttcgtcatc aacctgctga ccgaggcgat gtcgccgacc aacagcctga   1680
gcaacccggc ggcggtcaag cgcttcttcg agaccggcgg caagagcctg ctggacggcc   1740
tcggccacct ggccaaggac ctggtgaaca acggcgggat gccgagccag gtggacatgg   1800
acgccttcga ggtgggcaag aacctggcca ccaccgaggg cgccgtggtg ttccgcaacg   1860
acgtgctgga actgatccag taccggccga tcaccgagtc ggtgcacgaa cgcccgctgc   1920
tggtggtgcc gccgcagatc aacaagttct acgtcttcga cctgtcgccg gacaagagcc   1980
tggcgcgctt ctgcctgcgc aacggcgtgc agaccttcat cgtcagttgg cgcaacccga   2040
ccaagtcgca gcgcgaatgg ggcctgacca cctatatcga ggcgctcaag gaggccatcg   2100
aggtagtcct gtcgatcacc ggcagcaagg acctcaacct cctcggcgcc tgctccggcg   2160
ggatcaccac cgcgaccctg gtcggccact acgtggccag cggcgagaag aaggtcaacg   2220
ccttcaccca actggtcagc gtgctcgact tcgaactgaa tacccaggtc gcgctgttcg   2280
ccgacgagaa gactctggag gccgccaagc gtcgttccta ccagtccggc gtgctggagg   2340
gcaaggacat ggccaaggtg ttcgcctgga tgcgccccaa cgacctgatc tggaactact   2400
gggtcaacaa ctacctgctc ggcaaccagc cgccggcgtt cgacatcctc tactggaaca   2460
acgacaccac gcgcctgccc gccgcgctgc acggcgagtt cgtcgaactg ttcaagagca   2520
acccgctgaa ccgccccggc gccctggagg tctccggcac gcccatcgac ctgaagcagg   2580
tgacttgcga cttctactgt gtcgccggtc tgaacgacca catcaccccc tgggagtcgt   2640
gctacaagtc ggccaggctg ctgggtggca agtgcgagtt catcctctcc aacagcggtc   2700
acatccagag catcctcaac ccaccgggca accccaaggc acgcttcatg accaatccgg   2760
aactgcccgc cgagcccaag gcctggctgg aacaggccgg caagcacgcc gactcgtggt   2820
ggttgcactg gcagcaatgg ctggccgaac gctccggcaa gacccgcaag gcgcccgcca   2880
gcctgggcaa caagacctat ccggccggcg aagccgcgcc cggaacctac gtgcatgaac   2940
gatgaaaagc gaccagcctg aagaacagcc gcaggagcga tccgcggcct ccgccgacga   3000
aaccccgcca gcgcctccgg cgcggccccg tgccgcgcgg aagccggcca ggccccgtat   3060
cgccgagccc gcggctgcgc cgccgaggac cccgagcatg ccccagccct tcgtcttccg   3120
gaccatcgac ctcgacggcc agaccatccg caccgcagtg cggccgggca aggaaggaag   3180
cactccgctg ctgatcttca acggcatagg cgccaacctg gaactggtgt tccccttcgt   3240
ccaggcgctc gacccggaac tggaggtgat cgccttcgac gttcccggcg tcggcggttc   3300
ctcgacgccc agcgtgccct accgctttcc cggcctggcc aagctggcgg cgcggatgct   3360
cgactacctg gactacggcc aggtcaacgc gatcggcgtg tcctggggcg gcgcgctggc   3420
ccagcagttc gcccacgact atccggaacg ctgcaagaag ctgatcctcg ccgccacttc   3480
ggctggcgcg gtgatggtgc cgggcaagcc gaaggtactg atgcgcatgg ccagcccgcg   3540
gcgctacatc cagccctcct atggcgtaca catcgccccg gacatctacg gcggggcctt   3600
ccgccgcgac cccaagctgg ccatggcgca tgccagcaag gtgcgttcgt cgggcaagct   3660
gggctactac tggcaactgt tcgccgggct cggctggacc agcatccact ggctgcatag   3720
```

-continued

```
gatccgccag ccgaccctgg tgctggccgg cgacgacgac ccgatcatcc cgctgatcaa   3780
catgcgtgtg ctggcctggc gcattcccaa cgccgaactg cacgtgatcg acgacggcca   3840
cctgttcctg gtgacccgcg ccgaatcggt ggcgccgatc atcatgaagt tcctcgccga   3900
ggagcgccgt cgcgccgtca tgcaccctcg tccgttcctg cccaagaccg gctgaactgc   3960
tgcacgggca acaccagggc agcagacact gcttcgtcat ggtgcaggtg catagtcaat   4020
gttccgcaac ggcgcatggc gcctggcttc gccgcgacag cgcaagctct gcgacgcccc   4080
tcccggcgtt gtggtacagc gcttgctgcc ccactgtcgg gcggcaacct ccctgttcag   4140
gcaggtgtgc ggttctgccc cgggtgaaac ggaattcaca ggctataact gagtattccg   4200
agccagggga cgatcgcccg tggcatccag actgtggtcc tacgacggag tgtggtccat   4260
gcgagaaaag caggaatcgg gtagcgtgcc ggtgcccgcc gagttcatga gtgcacagag   4320
cgccatcgtc ggcctgcgcg gcaaggacct gctgacgacg gtccgcagcc tggctgtcca   4380
cggcctgcgc cagccgctgc acagtgcgcg gcacctggtc gccttcggag gccagttggg   4440
caaggtgctg ctgggcgaca ccctgcacca gccgaaccca caggacgccc gcttccagga   4500
tccatcctgg cgcctcaatc ccttctaccg gcgcaccctg caggcctacc tggcgtggca   4560
gaaacaactg ctcgcctgga tcgacgaaag caacctggac tgcgacgatc gcgcccgcgc   4620
ccgcttcctc gtcgccttgc tctccgacgc cgtggcaccc agcaacagcc tgatcaatcc   4680
actggcgtta aaggaactgt tcaataccgg cgggatcagc ctgctcaatg gcgtccgcca   4740
cctgctcgaa gacctggtgc acaacggcgg catgcccagc caggtgaaca agaccgcctt   4800
cgagatcggt cgcaacctcg ccaccacgca aggcgcggtg gtgttccgca acgaggtgct   4860
ggagctgatc cagtacaagc cgctgggcga gcgccagtac gccaagcccc tgctgatcgt   4920
gccgccgcag atcaacaagt actacatctt cgacctgtcg ccggaaaaga gcttcgtcca   4980
gtacgccctg aagaacaacc tgcaggtctt cgtcatcagt tggcgcaacc ccgacgccca   5040
gcaccgcgaa tggggcctga gcacctatgt cgaggccctc gaccaggcca tcgaggtcag   5100
ccgcgagatc accggcagcc gcagcgtgaa cctggccggc gcctgcgccg gcgggctcac   5160
cgtagccgcc ttgctcggcc acctgcaggt gcgccggcaa ctgcgcaagg tcagtagcgt   5220
cacctacctg gtcagcctgc tcgacagcca gatggaaagc ccggcgatgc tcttcgccga   5280
cgagcagacc ctggagagca gcaagcgccg ctcctaccag catggcgtgc tggacgggcg   5340
cgacatggcc aaggtgttcg cctggatgcg ccccaacgac ctgatctgga actactgggt   5400
caacaactac ctgctcggca ggcagccgcc ggcgttcgac atcctctact ggaacaacga   5460
caacacgcgg ctgcccgcgg cgttccacgg cgaactgctc gacctgttca agcacaaccc   5520
gctgacccgc ccgggcgcgc tggaggtcag cgggaccgcg gtggacctgg gcaaggtggc   5580
gatcgacagc ttccacgtcg ccggcatcac cgaccacatc acgccctggg acgcggtgta   5640
tcgctcggcc ctcctgctgg gcggccagcg ccgcttcatc ctgtccaaca gcgggcacat   5700
ccagagcatc ctcaaccctc ccggaaaccc caaggcctgc tacttcgaga acgacaagct   5760
gagcagcgat ccacgcgcct ggtactacga cgccaagcgc gaagagggca gctggtggcc   5820
ggtctggctg ggctggctgc aggagcgctc gggcgagctg ggcaaccctg acttcaacct   5880
tggcagcgcc gcgcatccgc ccctcgaagc ggcccccggc acctacgtgc atatacgctg   5940
aaagatccgg cccgggcgcc tggagccggg cacctccatc cccagaagaa gtccggatga   6000
agacacgcga ccgaatcctc gaatgctcgc tgttgctgtt caacgaacag ggcgagccca   6060
acgtctcgac actggagatc gccaacgaac tgggcatcag cccgggcaat ctctactacc   6120
```

```
acttccatgg caaggaaccg ctggtgatgg cgctgttcga gcggttccag gccgagttgg   6180

cgccgctgct cgatccgccc gaggaggtgc gcctgggcgc ggaggactac tggctgttcc   6240

tgcacctgat cgtcgagcgc ctcgcccact accgcttcct gttccaggac ctgtccaacc   6300

tgaccgggcg cctgccacgg ctggctcgcg gcatccgtac ctggctcggc gcgctgaagc   6360

ggaccctggc caccctgctg gcccgcctca aggccgaccg gcagttgcgc agcgacgcgc   6420

cggcactcgg gcaactggtc gaagagatca ccctgaccct gctgttctcc ctggattacc   6480

agcgggtact gggcagcaag ggcgaggtgc gcacggtggt ctaccagatc atgatgctgg   6540

tcgccccgca tctgcgcagc gaggcccaac gctcggcgga aagcctggcg cagcgctacc   6600

tgggaccgga atgaaaaacg cccggcgagt gccgggcgtg tgccttgccg ccaggactca   6660

gccctggctg ctcggcgtcg ccggagcgtt cgctgccgga gcgctggcag ccggtgtggc   6720

ggcgggggca gcgggcgcgc tcgaagacgc ggcgggagcg gccggtttcg ccgcggcggg   6780

cttggctgcc ggcttcttcg ccgcaggctt tttcgcagcc ggcttggcgg caggtttcgc   6840

cgcgggcttg gcggcggtcg cagcggccgg cttggctgcc ggcttcgcgg caggcttggc   6900

tgcggcaggt ttcgcagcag gcttcgccgc ggccttggct gccggcttgg tcgccggttt   6960

cgctgcggcc ttcgcagtcg gtttggcggc gggcttggct gccggcttgg cggccgcggt   7020

tttcgccgcg gtttttttcg ccgcgggttt cgccgcaggc ttggcggcgg ccttggctgc   7080

cggtttagct gccggcttgg ccgctgcggt tttcgccgcg ggcttggcag ccggtttcgc   7140

cgcaggcttg gccgctgcct tcgccgccgg cttgacgctg acgccggtga gtttctcgat   7200

ctgcttggtc agcgtatcga ccttgctgtg cagctccttc acctcgttgc ggctcggcac   7260

gccgagacgc gagatggcgc tgttcaggcg cttgtcgaaa gcttcctcga g            7311
```

<210> SEQ ID NO 11
<211> LENGTH: 5051
<212> TYPE: DNA
<213> ORGANISM: Aeromonas caviae

<400> SEQUENCE: 11

```
gatatccatc agcccctgac agagagcact gatatgaccg gcaggcatcg ccatcccctg     60

ccatcccgcc gcgtactggg tgtgattgga aaactgcacc gtattgacgg gccagacctc    120

catgccgaga cggcgcatgg ggaagacggc ggcgctgttg ccggcacagc cgaaaaccac    180

gtgggactgg atagagagaa tgcgtttcat cgacaccacc actgaagaag catgaggaaa    240

gcgggcaata tatcggatgc atagcgggct ctgccagcga ttcccggcaa ccctcgccat    300

ttatgcggca aaaagcccat tcaatggagt gttacaccaa cttcccccca cgcctgctca    360

acctggcaag ccaagagcgc ctcggccccg tcggtgtgat atgggctctt cacactcttg    420

tttgatggca tatgagggca tttttaatac aaggtggcgg atggcgggag aaagcgtcga    480

ggaagagcaa tgaggcgcgg cggcaggcaa gccggggccg acgccccggg ctttgtactt    540

aaggcttaag gcctgacgaa gtgatagacc cagccttcgt ccaggggga atcggagggc    600

gcagagacaa gtgccggcag ggaggcgacg gcccctccgg cggcgtattg cagcgccatc    660

agggcgcaga gggcggcgtc gtaacgatcc gtcccggcca ccacatcagg tggcaaggag    720

gcggctatct ccgccctggc cggtgaggcc ttgcctgcta ccttggcaaa gagccgggat    780

agacctccag cacggcgcga tcggcgtggg gctgctgcct cgggcacaag ctgcagatcc    840

ccgaggcgcg gcaagatgga gagcgccagg gtggcgttgt tgcctagcct gtcgaaggtg    900
```

-continued

```
gccgacagcg gcttcttgcc gtattgctgc tgcagccagc gctcgcagtc ccgataggca    960
taggggttgt ctatctcccg ctggggcacg gcgcactcga ctcccctccc cgccagcaga   1020
tcgccgaggg ctcggggaaa ggccaggggg gcatcgatgc cgagcgccag tcgcgggcag   1080
gccagcacct gcatcagcgc catctcgtct tgcagcgccg ggcgcagcaa ggcgtccaga   1140
tccggcgcca cccgggagct caaccgaaac aggggggaga ccccgagcca gtgcaactgc   1200
tgcgtgcggg cctgccagcc caccacggcc accgcctggg cattgccctg ccagcccctt   1260
acatcccaac cgatgccgat ggcatccaag tgttccgttg tcatgcccct gtcacctctg   1320
cgcactattg atggagcaca gggtaatggc tgcgcccctc aaagcaaggc tggcggcacc   1380
gcttagaaag atttcttgaa gttgatcagc ggcaagatgg ggaagatgcc gttctctgcg   1440
tagttggcga gccctatctg caggccatcg aggtgcttgg tggcattgat gaagccaagc   1500
tggaaggtgg tgcgctcggc atagttgacg aagccgaggt tggccagggc attgcccttg   1560
gcgatgttga ccgcccccca gttcagcccc tgcacgttgt tggtcaggtt gacgaaaccc   1620
aggttgaccc cggtgtcctg cccctcatgc cagttgacgg cgttgatggc gaccccgccg   1680
aactgatggc gcacccgggc ggcgccgaag aagatgccaa gctgcaggcc ggtgaactga   1740
tccacgtcgg agagggcgaa caccggcaga tctatgccct tcacctgacc ggtgcggcca   1800
tacaggaagg aggcgcgcgc cccttccacc tggtgggagg aaggcaggtt gatgccgggc   1860
agggagatct ggaccggggt gctggcctgg gccacgccgg cgagggccag cgcggagcaa   1920
ccgagcagca gggcgagagg tttcatcggg attccttggc agtctgaatg acgtgccagc   1980
ctatcagcgc ggcgccggtg cggcgagggc gcgccggacc cagtgcgtca cctctcgtct   2040
gatccgcctc cctcgacggg cgtcgctgac aaaaaaattc aaacagaaat taacatttat   2100
gtcatttaca ccaaaccgca tttggttgca gaatgctcaa acgtgtgttt gaacagagca   2160
agcaacacgt aaacagggat gacatgcagt acccgtaaga agggccgatt ggcccacaac   2220
aacactgttc tgccgaactg gagaccgatg atgaatatgg acgtgatcaa gagctttacc   2280
gagcagatgc aaggcttcgc cgcccccctc acccgctaca accagctgct ggccagcaac   2340
atcgaacagc tgacccggtt gcagctggcc tccgccaacg cctacgccga actgggcctc   2400
aaccagttgc aggccgtgag caaggtgcag gacacccaga gcctggcggc cctgggcaca   2460
gtgcaactgg agaccgccag ccagctctcc cgccagatgc tggatgacat ccagaagctg   2520
agcgccctcg gccagcagtt caaggaagag ctggatgtcc tgaccgcaga cggcatcaag   2580
aaaagcacgg gcaaggcctg ataacccctg gctgcccgtt cgggcagcca catctcccca   2640
tgactcgacg ctacgggcta gttcccgcct cgggtgtggg tgaaggagag cacatgagcc   2700
aaccatctta tggcccgctg ttcgaggccc tggcccacta caatgacaag ctgctggcca   2760
tggccaaggc ccagacagag cgcaccgccc aggcgctgct gcagaccaat ctggacgatc   2820
tgggccaggt gctggagcag ggcagccagc aaccctggca gctgatccag gcccagatga   2880
actggtggca ggatcagctc aagctgatgc agcacaccct gctcaaaagc gcaggccagc   2940
cgagcgagcc ggtgatcacc ccggagcgca gcgatcgccg cttcaaggcc gaggcctgga   3000
gcgaacaacc catctatgac tacctcaagc agtcctacct gctcaccgcc aggcacctgc   3060
tggcctcggt ggatgccctg gagggcgtcc cccagaagag ccgggagcgg ctgcgtttct   3120
tcacccgcca gtacgtcaac gccatggccc ccagcaactt cctggccacc aaccccgagc   3180
tgctcaagct gaccctggag tccgacggcc agaacctggt gcgcggactg gccctcttgg   3240
ccgaggatct ggagcgcagc gccgatcagc tcaacatccg cctgaccgac gaatccgcct   3300
```

```
tcgagctcgg gcgggatctg gccctgaccc cgggccgggt ggtgcagcgc accgagctct   3360

atgagctcat tcagtacagc ccgactaccg agacggtggg caagacacct gtgctgatag   3420

tgccgccctt catcaacaag tactacatca tggacatgcg gccccagaac tccctggtcg   3480

cctggctggt cgcccagggc cagacggtat tcatgatctc ctggcgcaac ccgggcgtgg   3540

cccaggccca aatcgatctc gacgactacg tggtggatgg cgtcatcgcc gccctggacg   3600

gcgtggaggc ggccaccggc gagcgggagg tgcacggcat cggctactgc atcggcggca   3660

ccgccctgtc gctcgccatg ggctggctgg cggcgcggcg ccagaagcag cgggtgcgca   3720

ccgccaccct gttcactacc ctgctggact tctcccagcc cggggagctt ggcatcttca   3780

tccacgagcc catcatagcg gcgctcgagg cgcaaaatga ggccaagggc atcatggacg   3840

ggcgccagct ggcggtctcc ttcagcctgc tgcgggagaa cagcctctac tggaactact   3900

acatcgacag ctacctcaag ggtcagagcc cggtggcctt cgatctgctg cactggaaca   3960

gcgacagcac caatgtggcg ggcaagaccc acaacagcct gctgcgccgt ctctacctgg   4020

agaaccagct ggtgaagggg gagctcaaga tccgcaacac ccgcatcgat ctcggcaagg   4080

tgaagacccc tgtgctgctg gtgtcggcgg tggacgatca catcgccctc tggcagggca   4140

cctggcaggg catgaagctg tttggcgggg agcagcgctt cctcctggcg gagtccggcc   4200

acatcgccgg catcatcaac ccgccggccg ccaacaagta cggcttctgg cacaacgggg   4260

ccgaggccga gagcccggag agctggctgg caggggcgac gcaccagggc ggctcctggt   4320

ggcccgagat gatgggcttt atccagaacc gtgacgaagg gtcagagccc gtccccgcgc   4380

gggtcccgga ggaagggctg gccccccgccc ccggccacta tgtcaaggtg cggctcaacc   4440

ccgtgtttgc ctgcccaaca gaggaggacg ccgcatgagc gcacaatccc tggaagtagg   4500

ccagaaggcc cgtctcagca agcggttcgg ggcggcggag gtagccgcct tcgccgcgct   4560

ctcggaggac ttcaaccccc tgcacctgga cccggccttc gccgccacca cggcgttcga   4620

gcggcccata gtccacggca tgctgctcgc cagcctcttc tccgggctgc tgggccagca   4680

gttgccgggc aaggggagca tctatctggg tcaaagcctc agcttcaagc tgccggtctt   4740

tgtcggggac gaggtgacgg ccgaggtgga ggtgaccgcc cttcgcgagg acaagcccat   4800

cgccaccctg accacccgca tcttcaccca aggcggcgcc ctcgccgtga cgggggaagc   4860

cgtggtcaag ctgccttaag caccggcggc acgcaggcac aatcagcccg gcccctgccg   4920

ggctgattgt tctcccccgc tccgcttgcc cccttttttcg gggcaatttg gcccaggccc   4980

tttccctgcc ccgcctaact gcctaaaatg gccgccctgc cgtgtaggca ttcatccagc   5040

tagaggaatt c                                                        5051
```

<210> SEQ ID NO 12
<211> LENGTH: 2849
<212> TYPE: DNA
<213> ORGANISM: Thiococcus pfennigii

<400> SEQUENCE: 12

```
ggatcctggt cgcgagcgcg ccgcccagcc acctgccggc gcgccccgcc gggaccgctc     60

gaggacgcct cgcgaaggct ctaggggctg tatcttcaag agtctacgcc cctttgttgc    120

agtgcacaaa tttccgtgct agcttcatgc tatcacgccc cagacgagga agattcaccg    180

tgaacgatac ggccaacaag accagcgact ggctggacat ccaacgcaag tactgggaga    240

cctggtcgga gctcggccgc aagaccttgg gtctggagaa gaccccggcc aatccttggg    300
```

-continued

```
ccggcgccct cgatcattgg tggcagacgg tctcgcccgc cgccccccaac gacctggttc    360
gcgacttcat ggagaagctc gccgagcagg gcaaggcctt cttcggcctc accgactact    420
tcacgaaggg cctcggcggc agtagcggta cgcagggctg ggacaccctc tcgaagacca    480
tcgacgacat gcaaaaggcc ttcgccagcg gccggatcga aggcgacgag accttccgcc    540
gcctgatggc cttctgggag atgccgctcg acaactggca gcgcaccatg tcctcgctgt    600
ccccggtgcc cggcgacctg ctgcgcaaca tgccgcacga ccaagtcagg gacagcgtcg    660
accgcatcct ctcggcaccc gggctcggct acacgcgcga ggagcaggcc cgctaccagg    720
atctgatccg ccgctcgctg gagtaccagt cggccctgaa cgaatacaac ggcttcttcg    780
gccagctcgg tgtcaagtcc ctcgagcgga tgcgcgcctt cctgcaggga caggccgaga    840
agggcgtcgc catcgagtcg gcgcgcaccc tctacgacgc ctgggtcggc tgctgcgaag    900
aggtctatgc cgaggaggtc agctccgccg actacgcgca catccacggc cgcctcgtca    960
acgcccagat ggccctcaag cagcgcatgt cgaccatggt cgacgaggtc ctcggcgcga   1020
tgccgctgcc gacccgcagc gagctgcgca cgctccagga tcggctccag gagtcgcgcg   1080
gcgagggcaa gcgccagcgc caagagatcg agacgctgaa gcggcaggtc gcggccttgg   1140
ccggcggcgc ccagcccgcg ccccaggcct ccgcccagcc cagcacccgg cccgcgccgg   1200
cgacggcccc ggcggcgagc gcggcgccca agcgcagcac cacgacccgc cgcaagacca   1260
ccaagcccac caccggccag tgatgtcggc cgcccgtcca tcgccaccag gagagagtgc   1320
cgtgtcccca ttcccgatcg acatccggcc cgacaagctg accgaggaga tgctggagta   1380
cagccgcaag ctcggcgagg gtatgcagaa cctgctcaag gccgaccaga tcgacacagg   1440
cgtcaccccc aaggacgtcg tccaccgcga ggacaagctg gtcctctacc gctaccggcg   1500
cccggcgcag gtggcgaccc agacgatccc gctgctgatc gtctacgccc tcgtcaatcg   1560
gccctacatg accgacatcc aggaggatcg ctcgacgatc aagggcctgc tcgccaccgg   1620
tcaggacgtc tatctgatcg actggggcta cccggatcag gccgaccggg cgctgaccct   1680
cgatgactac atcaacggct acatcgaccg ctgcgtcgac tacctgcgcg agacccacgg   1740
cgtcgaccag gtcaacctgc tcgggatctg ccagggcggg gccttcagcc tctgctacac   1800
ggccctgcac tccgagaagg tcaaaaacct cgtcaccatg gtcacgccgg tcgacttcca   1860
gaccccgggc aacctgctct cggcctgggt ccagaacgtc gacgtcgacc tggccgtcga   1920
caccatgggc aacatcccgg gcgaactgct caactggacc ttcctgtcgc tcaagccctt   1980
cagcctgacc ggccagaagt acgtcaacat ggtcgacctg ctcgacgacg aggacaaggt   2040
caagaacttc ctgcggatgg agaagtggat cttcgacagc ccggaccagg ccggcgagac   2100
cttccgccag ttcatcaagg acttctacca gcgcaacggc ttcatcaacg gcggcgtcct   2160
gatcggcgat caggaggtcg acctgcgcaa catccgctgc ccggtcctga acatctaccc   2220
gatgcaggac cacctggtgc cgccggatgc ctccaaggcc ctcgcgggac tgacctccag   2280
cgaggactac acggagctcg ccttccccgg cgggcacatc ggcatctacg tcagcggcaa   2340
ggcgcaggaa ggagtcaccc cggcgatcgg ccgctggctg aacgaacgcg gctgagccgg   2400
gtcgacccac ccgctcgacg ggcgcggccg gcggcatcga aggccgccgg ccggcgccca   2460
tgagccatcc gcgccgctgg cgcccgcccc ccgaccttcg ccgccgcacc cgcatcgccc   2520
ccgcggctgg cgtacaatga cggtcttcgc gagcgagccc cgcatcgtca acggaggctg   2580
catgggcgcc gaccaccaac tgctggccgc gtacgacgcg ctggccgaga cctacgacgc   2640
ccaccgcggc ctcttcgaca tgcgcgccgt gctcgaggac atcttcgccc gcctgccggc   2700
```

```
ctgcggcacc ctcctcgacc tcggctgcgg cgccggggag ccgtgcgcgc gcgccttcct   2760

cgaccgcggc tggcgggtga ccggggtgga cttctgcccg gccatgctcg ccctcgcggc   2820

gcgctacgtc cccgagatgg agcggatcc                                      2849
```

```
<210> SEQ ID NO 13
<211> LENGTH: 2768
<212> TYPE: DNA
<213> ORGANISM: Ralstonia eutropha

<400> SEQUENCE: 13

cccgggcaag taccttgccg acatctatgc gctggcgcgc acgcgcctgg cgcgcgccgg     60

ctgtaccgag gtctacggcg gcgacgcctg caccgtggcc gacgccggtc gcttctactc    120

ctatcggcgc gatggcgtga ccggccgcat ggccagcctg gtctggctgg cggactgagc    180

ccgccgctgc ctcactcgtc cttgcccctg gccgcctgcg cgcgctcggc ttcagccttg    240

cgtcggcggc ggccgggcgt gcccatgatg tagagcacca cgccaccggc gccatgccat    300

acatcaggaa ggtggcaacg cctgccacca cgttgtgctc ggtgatcgcc atcatcagcg    360

ccacgtagag ccagccaatg gccacgatgt acatcaaaaa ttcatccttc tcgcctatgc    420

tctggggcct cggcagatgc gagcgctgca taccgtccgg taggtcggga agcgtgcagt    480

gccgaggcgg attcccgcat tgacagcgcg tgcgttgcaa ggcaacaatg gactcaaatg    540

tctcggaatc gctgacgatt cccaggtttc tccggcaagc atagcgcatg gcgtctccat    600

gcgagaatgt cgcgcttgcc ggataaaagg ggagccgcta tcggaatgga cgcaagccac    660

ggccgcagca ggtgcggtcg agggcttcca gccagttcca gggcagatgt gccggcagac    720

cctcccgctt tgggggaggc gcaagccggg tccattcgga tagcatctcc ccatgcaaag    780

tgccggccag ggcaatgccc ggagccggtt cgaatagtga cggcagagag acaatcaaat    840

catggcgacc ggcaaaggcg cggcagcttc cacgcaggaa ggcaagtccc aaccattcaa    900

ggtcacgccg gggccattcg atccagccac atggctggaa tggtcccgcc agtggcaggg    960

cactgaaggc aacggccacg cggccgcgtc cggcattccg ggcctggatg cgctggcagg   1020

cgtcaagatc gcgccggcgc agctgggtga tatccagcag cgctacatga aggacttctc   1080

agcgctgtgg caggccatgg ccgagggcaa ggccgaggcc accggtccgc tgcacgaccg   1140

gcgcttcgcc ggcgacgcat ggcgcaccaa cctcccatat cgcttcgctg ccgcgttcta   1200

cctgctcaat gcgcgcgcct tgaccgagct ggccgatgcc gtcgaggccg atgccaagac   1260

ccgccagcgc atccgcttcg cgatctcgca atgggtcgat gcgatgtcgc ccgccaactt   1320

ccttgccacc aatcccgagg cgcagcgcct gctgatcgag tcgggcggcg aatcgctgcg   1380

tgccggcgtg cgcaacatga tggaagacct gacacgcggc aagatctcgc agaccgacga   1440

gagcgcgttt gaggtcggcc gcaatgtcgc ggtgaccgaa ggcgccgtgg tcttcgagaa   1500

cgagtacttc cagctgttgc agtacaagcc gctgaccgac aaggtgcacg cgcgcccgct   1560

gctgatggtg ccgccgtgca tcaacaagta ctacatcctg gacctgcagc cggagagctc   1620

gctggtgcgc catgtggtgg agcagggaca tacggtgttt ctggtgtcgt ggcgcaatcc   1680

ggacgccagc atggccggca gcacctggga cgactacatc gagcacgcgg ccatccgcgc   1740

catcgaagtc gcgcgcgaca tcagcggcca ggacaagatc aacgtgctcg gcttctgcgt   1800

gggcggcacc attgtctcga ccgcgctggc ggtgctggcc gcgcgcggcg agcacccggc   1860

cgccagcgtc acgctgctga ccacgctgct ggactttgcc gacacgggca tcctcgacgt   1920
```

-continued

```
ctttgtcgac gagggccatg tgcagttgcg cgaggccacg ctgggcggcg gcgccggcgc   1980

gccgtgcgcg ctgctgcgcg gccttgagct ggccaatacc ttctcgttct tgcgcccgaa   2040

cgacctggtg tggaactacg tggtcgacaa ctacctgaag ggcaacacgc cggtgccgtt   2100

cgacctgctg ttctggaacg gcgacgccac caacctgccg gggccgtggt actgctggta   2160

cctgcgccac acctacctgc agaacgagct caaggtaccg ggcaagctga ccgtgtgcgg   2220

cgtgccggtg gacctggcca gcatcgacgt gccgacctat atctacggct cgcgcgaaga   2280

ccatatcgtg ccgtggaccg cggcctatgc ctcgaccgcg ctgctggcga acaagctgcg   2340

cttcgtgctg ggtgcgtcgg gccatatcgc cggtgtgatc aacccgccgg ccaagaacaa   2400

gcgcagccac tggactaacg atgcgctgcc ggagtcgccg cagcaatggc tggccggcgc   2460

catcgagcat cacggcagct ggtggccgga ctggaccgca tggctggccg ggcaggccgg   2520

cgcgaaacgc gccgcgcccg ccaactatgg caatgcgcgc tatcgcgcaa tcgaacccgc   2580

gcctgggcga tacgtcaaag ccaaggcatg acgcttgcat gagtgccggc gtgcgtcatg   2640

cacggcgccg gcaggcctgc aggttccctc ccgtttccat tgaaaggact acacaatgac   2700

tgacgttgtc atcgtatccg ccgcccgcac cgcggtcggc aagtttggcg gctcgctggc   2760

caagatcc                                                            2768
```

```
<210> SEQ ID NO 14
<211> LENGTH: 1980
<212> TYPE: DNA
<213> ORGANISM: Acinetobacter sp.

<400> SEQUENCE: 14

ctgaattcaa atcggaattt gaaaagttag ttagcgaatc tatgcctaac aataaataac     60

actgctctga aaaccatgcg ttatcaggac gaatgttacg gggaagtgtg aaaatttccc    120

cgttttagtt tcagccctgc actcaatttg attgctaaaa gccatgtgct atggagcgat    180

gaaatgaacc cgaactcatt tcaattcaaa gaaaacatac tacaattttt ttctgtacat    240

gatgacatct ggaaaaaatt acaagaattt tattatgggc aaagcccaat taatgaggct    300

ttggcgcagc tcaacaaaga agatatgtct ttgttctttg aagcactatc taaaaaccca    360

gctcgcatga tggaaatgca atggagctgg tggcaaggtc aaatacaaat ctaccaaaat    420

gtgttgatgc gcagcgtggc caaagatgta gcaccattta ttcagcctga aagtggtgat    480

cgtcgtttta acagcccatt atggcaagaa cacccaaatt ttgacttgtt gtcacagtct    540

tatttactgt ttagccagtt agtgcaaaac atggtagatg tggtcgaagg tgttccagac    600

aaagttcgct atcgtattca cttctttacc cgccaaatga tcaatgcgtt atctccaagt    660

aactttctgt ggactaaccc agaagtgatt cagcaaactg tagctgaaca aggtgaaaac    720

ttagtccgtg gcatgcaagt tttccatgat gatgtcatga atagcggcaa gtatttatct    780

attcgcatgg tgaatagcga ctctttcagc ttgggcaaag atttagctta cacccctggt    840

gcagtcgtct ttgaaaatga cattttccaa ttattgcaat atgaagcaac tactgaaaat    900

gtgtatcaaa cccctattct agtcgtacca ccgtttatca ataaatatta tgtgctggat    960

ttacgcgaac aaaactcttt agtgaactgg ttgcgccagc aaggtcatac agtcttttta   1020

atgtcatggc gtaacccaaa tgccgaacag aaagaattga cttttgccga tctcattaca   1080

caaggttcag tggaagcttt gcgtgtaatt gaagaaatta ccggtgaaaa agaggccaac   1140

tgcattggct actgtattgg tggtacgtta cttgctgcga ctcaagccta ttacgtggca   1200

aaacgcctga aaaatcacgt aaagtctgcg acctatatgg ccaccattat cgactttgaa   1260
```

-continued

```
aacccaggca gcttaggtgt atttattaat gaacctgtag tgagcggttt agaaaacctg   1320

aacaatcaat tgggttattt cgatggtcgt cagttggcag ttaccttcag tttactgcgt   1380

gaaaatacgc tgtactggaa ttactacatc gacaactact taaaaggtaa agaaccttct   1440

gattttgata ttttatattg gaacagcgat ggtacgaata tccctgccaa aattcataat   1500

ttcttattgc gcaatttgta tttgaacaat gaattgattt caccaaatgc cgttaaggtt   1560

aacggtgtgg gcttgaatct atctcgtgta aaaacaccaa gcttctttat tgcgacgcag   1620

gaagaccata tcgcactttg ggatacttgt ttccgtggcg cagattactt gggtggtgaa   1680

tcaaccttgg ttttaggtga atctggacac gtagcaggta ttgtcaatcc tccaagccgt   1740

aataaatacg gttgctacac caatgctgcc aagtttgaaa ataccaaaca atggctagat   1800

ggcgcagaat atcaccctga atcttggtgg ttgcgctggc aggcatgggt cacaccgtac   1860

actggtgaac aagtccctgc ccgcaacttg ggtaatgcgc agtatccaag cattgaagcg   1920

gcaccgggtc gctatgtttt ggtaaattta ttctaatcgg tcatataaca acagccatgc   1980
```

```
<210> SEQ ID NO 15
<211> LENGTH: 4936
<212> TYPE: DNA
<213> ORGANISM: Alcaligenes latus

<400> SEQUENCE: 15

ggttcttctc gttccggcgg gaccgggtca cggggcggca ggctgccgcc gtctggctgc     60

gcggatgaag cggtgtcctc ggcgcgcttg cgcgcccgtc gccgcgccgg cgtccccagg    120

aagtacagga cgatggacaa gggcagtacg ccatacagca gcagcgtgaa caccgcgccg    180

agcaaggtgc cgttgggcgc catggcttcg gccacggcca tcatcagcac cacgtacagc    240

catgccagag caaccaagta catagcaaaa acccgcaatt acgcagaatg acgtatttcg    300

tacaatgaaa actgttgtca tgatgcggta agacacgaag cctacaacgc gatccagcaa    360

cggttttcgt gaaaaagtcc tcaggagacg agcgtgacac tgcatcccat tcccgcactg    420

caacagcttg gcgacaacgc cacggcgctg agtgccgcca tctcggaagc gctgcgcgcg    480

atgtcgggcc tgaacctgcc gatgcaggcc atgaccaagc tgcagggcga gtacctcaac    540

gaggcgacgg cgctgtggaa ccagacgctg ggccgcctgc agcccgacgg cagcgcccaa    600

ccggccaagc tgggcgaccg gcgcttctcg gccgaggact gggccaagaa ccccgccgcg    660

gcctacctgg cgcaggtcta cctgctcaat gcccgcacgc tgatgcagat ggccgagtcc    720

atcgagggcg acgccaaggc caaggcgcgc gtgcgcttcg ccgtgcagca gtggatcgac    780

gccgcggcgc cgagcaactt cctggcgctc aatcccgagg cgcagcgcaa ggcgctggag    840

accaaggggg agagcatcag ccagggcctg cagcagctgt ggcatgacat ccagcagggc    900

cacgtgtcgc agacggacga gagcgtgttc gaggtgggca agaacgtcgc caccaccgag    960

ggcgcggtcg tgtacgagaa cgacctgttc cagctcatcg agtacaagcc gctgacgccc   1020

aaggtgcacg agaagccgat gctgttcgtg ccgccgtgca tcaacaagta ctacatcctg   1080

gacctgcagc cggacaacag cctcatccgc tacaccgtcg cccagggcca ccgggtgttc   1140

gtggtgagct ggcgcaaccc cgacgcctcc gtcgccggca agacctggga cgactacgtg   1200

gagcagggcg tgatccgcgc catccgcgtg atgcagcaga tcacggggca cgagaaggtc   1260

aacgcgctgg gcttctgcgt cggcggcacc atcctgagca cggcgctggc ggtgctggcc   1320

gcgcgcggcg agcagcccgc ggcgagcctg acgctgctga ccacgctgct ggacttcagc   1380
```

-continued

```
aacaccggcg tgctggacct gttcatcgac gaggccggcg tgcgcctgcg cgagatgacc   1440
atcggcgaga aggcgcccaa cggcccgggc ctgctcaacg gcaaggagct ggccaccacc   1500
ttcagcttcc tgcgcccgaa cgacctggtc tggaactacg tggtgggcaa ctacctcaag   1560
ggcgaggcgc cgccgccctt cgacctgctg tactggaact ccgacagcac caacatggcc   1620
gggcccatgt tctgctggta cctgcgcaac acctacctgg agaacaagtt gcgcgttccc   1680
ggtgccctga ccatctgcgg cgagaaggtg gacctctcgc gcatcgaggc gccggtgtac   1740
ttctacggtt cgcgcgagga ccacatcgtg ccctgggaat cggcctacgc cggcacgcag   1800
atgctgagcg gccccaagcg ctatgtcctg ggtgcgtctg gccacatcgc cggcgtgatc   1860
aaccccccgc agaagaagaa gcgcagctac tggaccaacg agcagctcga cggcgacttc   1920
aaccagtggc tggaaggctc caccgagcat cctggcagct ggtggaccga ctggagcgac   1980
tggctcaagc agcacgcggg caaggaaatc gccgcaccca agactcccgg caacaagacc   2040
cacaagccca tcgagcccgc ccccgggcgt tacgtgaagc agaaggcctg agccgcggcc   2100
cctgagcctt ctttaacccg accttgacaa acgaggagat aagcatgacc gacatcgtca   2160
tcgtcgccgc agcccgcacc gccgtgggca agttcggcgg cacgctggcc aagacccccg   2220
ctccggagct gggcgccgtg gtcatcaagg ccctgctgga gaagacgggc gtcaagcccg   2280
accagatcgg tgaagtcatc atgggccagg tgctggccgc cggcgcgggc cagaaccccg   2340
cgcgccaggc gatgatgaag gcgggcatcg ccaaggaaac gccggcgctg accatcaacg   2400
ccgtgtgcgg ctccggcctc aaggccgtga tgctggccgc ccaggccatc gcctggggcg   2460
acagcgacat cgtcatcgcc ggcggccagg agaacatgag cgccagcccg cacgtgctga   2520
tgggcagccg cgacggccag cgcatgggcg actggaagat ggtcgacacc atgatcaacg   2580
acggcctgtg ggacgtgtac aacaagtacc acatgggcat cacggccgag aacgtcgcca   2640
aggaacacga catcagccgc gaccagcagg acgccctggc cctggccagc cagcagaagg   2700
ccaccgccgc gcaggaagcc ggccgcttca aggacgagat cgttccggtc tcgatcccgc   2760
agcgcaaggg cgacccggtg ctgttcgaca ccgacgagtt catcaacaag aagaccaccg   2820
ccgaagcgct ggcgggcctg cgcccggcct tcgacaaggc cggcagcgtg accgcgggca   2880
acgcctcggg catcaacgac ggcgccgctg cggtgatggt gatgtccgcc gccaaggcga   2940
aggagctggg cctgacgccc atggcgcgca tcaagagctt cggcaccagc ggcctggatc   3000
cggccaccat gggcatgggc ccggtgccgg cctcgcgcaa ggcgctggag cgcgccggct   3060
ggcaggtcgg tgacgtggac ctgttcgagc tcaacgaagc cttcgccgcc caggcctgcg   3120
cggtgaacaa ggagctgggc gtggatccgg ccaaggtcaa cgtcaacggc ggtgccatcg   3180
ccatcggcca ccccatcggc gcctccggct gccgcgtgct ggtgacgctg ctgcacgaga   3240
tgcagcgccg ggacgccaag aagggcctgg ccgcgctgtg catcggcggc ggcatgggcg   3300
tgtcgctgac cgtcgagcgc tgatcagaag aaccgggcgg ccccgcgccg cccgcccggc   3360
gttccacgcg ggtgcgccgg gataccagac gaaccaaacc accaagggct tcgagacggc   3420
ccgaagaagg agagacagat ggcacagaaa ctggcttacg tgaccggcgg catgggcggc   3480
atcggcacct cgatgtgcca gcgcctgcac aaggacggct tcaaggtgat cgccggctgc   3540
ggtccgagcc gcgaccacca gaagtggatc gatgaacagg ccgcgctggg ctataccttc   3600
tacgcctccg tgggcaacgt ggccgactgg gactccaccg tggccgcctt cgagaaggtc   3660
aaggccgagc acggcaccgt ggacgtgctg gtgaacaacg ccggcatcac gcgtgacggg   3720
cagttccgca agatgagcaa ggccgattgg caggccgtga tgtcgaccaa cctcgacagc   3780
```

-continued

```
atgttcaacg tcaccaagca ggtgatcgag ggcatgctgg acaagggctg ggccggatc   3840
atcaacatct cctcggtcaa cggcgagaag ggccagttcg gccagaccaa ctactccgcc   3900
gccaaggccg gcatgcacgg cttctcgatg gcgctggcgc aggaagtggc ggccaagggc   3960
gtgacggtga acaccgtgag cccgggctac atcgccacgg acatggtcaa ggccatccgc   4020
caggacgtgc tggacaagat catcgccacc attcccatcc gtcgcctggg tacgccggag   4080
gagatcgcct ccatcgtcgc ctggctggcc ggcgaggagt cgggcttcac caccggtgcc   4140
gacttcagct gcaacggcgg cctgcacatg ggctgaggcc cgcggctcca tgcccacctg   4200
cgtgggcatg gacgggccga aggacccgag ctctgcgagg gtgcggcctg caaggctgag   4260
gcctgctgcg ccgcgtgccc gcgagggcac gtgccgaagc accaaaaggc cgcgcattgc   4320
gcggcctttt cctttctgga tcggtgcgga cgggtgccgc gtcaggcagg gcagggcccc   4380
cgggccttca ctccaccatg cccgacatga agtacttgat cagccccttg gccgcgaagc   4440
ccagcatgcc gaagcccagc gccaggaaca gcacgaaggt gccgaacttg ccggccttcg   4500
actcgcgcgc gagctgaaag atgatgaatg ccatgtagag catgaaggcc gtgacgccga   4560
cggtcaggcc cagctgggca atgttttcct cgttgatttc gaacatcgtt tgttgtctca   4620
ggctgctgca cgcggctgac gtgctcgccg cgcggccggg ccccaactgc ccgcagcggt   4680
tctcgatcag gttctcaagg catctcgtgc cactgggagg tgtccaccag gtcgcggtag   4740
gcgtgccagc tcgaatgcgc cagccacggc actaccacga tcaggcccag cagcagcgtg   4800
gccatgccca gcagcgtcag cgccatgatc agcgccgccc acagcgccag cggcagtggg   4860
tgctgcatca ccacgcgcca gctcgtgagc accgccacca gcacgcccac gtggcggtcc   4920
agcagcatcg ggatcc                                                   4936
```

<210> SEQ ID NO 16
<211> LENGTH: 1752
<212> TYPE: DNA
<213> ORGANISM: Azorhizobium caulinodans

<400> SEQUENCE: 16

```
atggaggcgt tcgcccagaa ccttgcgaag atggtggagg aaggcggcaa ggccgtcgcc     60
gcttacatgc gtccgcgcga ggagggcaag ccggacgaca tgacggacga tatcgccgat    120
gcgctcaaga ccatcggcga ggtggccaat tactggatgt ccgatccaaa gcgctccttc    180
gaggcccagt cgcgcctcat gatgggctac atgggcgtct gggcgggggc gctccagaag    240
ctctccggcg agaaggccga gcccatcgcg aaggccgacc ccaaggacgg ccgcttcaag    300
gacccggaat gggaaagccc gttcttcgac gccctgaagc agacctatct cgtgaccagc    360
aactgggccg agtccatggt caaggaggcc gaggggctcg atccccacac caagcacaag    420
gccgaattcc tggtgcgcca gctctcgaat gcggtggcgc cctcgaactt cctcatgacc    480
aacccggagc tgatccgcga aacgctctcc tccagcggcg agaacctcgt gcgcggcatg    540
aagaatctgg ccgaggatct ggtggagggc aaaggcgatc tcaagatccg ccagacggac    600
atgagcgcct tcgaggtggg ccgcaatctg gcgctcagcc ccggcaaggt catcttcgag    660
accgagctga tgcagctcat ccagtatgcg ccctcgacgc ccagcgtgaa gaagacgccg    720
gtgctgatcg tgccgccctg gatcaacaag ttctacatcc tcgacctgac gcccgagaaa    780
tccctcatca agtggatggt ggatcagggg ctgacggtct tcgtcatctc gtgggtcaat    840
ccggacgccc gtctcgccga caagggcttc gacgactaca tgcgcgatgg catcttcgcc    900
```

-continued

```
gcgctcgatg cggtggagaa ggcgaccggc gagcatcagg cgcacaccat cggctattgc    960

gtgggcggca cgctgctcgc ggtcacgctt gcctacatgg cggcgaccgg cgatgaccgg   1020

gtggcgagct ccaccttcct caccacccag atcgacttca cccacgcggg cgatctcaag   1080

gtcttcgtgg acgaggcgca gctctcggtc atcgagcgtc gcatgaagga gatgggctat   1140

cttgaaggac gcaagatggc cgacgccttc aacatgctgc ggtccaacga cctgatctgg   1200

ccctatgtgg tgaacaatta tctcaagggg aagcagccgt tccccttcga tcttctgttc   1260

tggaatgccg attccacccg catgccggcg gcgaaccact cctattacct gcgcaactgc   1320

tatctccaga acaacatcgc caaggggctg gcggagatcg cgggcgtcaa gatcgacatg   1380

ggcaaggtga cgatcccggt ctattcgctc gccacccgcg aggaccatat cgcgccgccc   1440

aactccgctt atatcggtgc aggcctgctc ggcggccccg tgcgcttcgt gctggccggg   1500

tccggccata ttgcgggcgt ggtcaatccg ccggtgaagc acaagtacca gtactggacc   1560

ggcggtccga ccggcgggga ctatgacgtc tggctgaagg gggcgcagga gcacaagggc   1620

tcgtggtggc cggattgggc gcagtggttc agcgccctgc atccggacga ggtccctgcc   1680

cgcgagccag gcggcagcgc gttcaatccc atcgaggatg cccccggccg ctacgtacgc   1740

gagaagtcct ga                                                       1752
```

<210> SEQ ID NO 17
<211> LENGTH: 3973
<212> TYPE: DNA
<213> ORGANISM: Comamonas acidovorans

<400> SEQUENCE: 17

```
cccgggcaag cggcgcagca gaccctggcc tggctgggac cctgcatcgg tccgcgctcc     60

ttcgaagtgg gagccgaggt gcgcgcggcc ttcatcgcgc atgacgcggc ggccggggcg    120

catttcaccg ccgtggcgca agagggcggg ggcgcaccca agtacctggc caacctggcc    180

gggcttgcgc gccagcgcct ggcggcgctg ggcatcaccg ccatctacgg caatgacggc    240

ggcgacgcat ggtgcacggt gctcaacggc tcacggttct tttcgcaccg gcgcgacgct    300

gcccgcctcg gcagcagcgg gcggttcgcc gcctgcatct ggaaggactg agcgcgcctg    360

cgtgccgggg ccgttttgcg aggcctgctg ctgcgcgagc caggcctcgc gctcggccaa    420

ttcgcgtgca tggcgttttc gcttgcgcgc gggcgtgccc atgatgtaga tcacgatcga    480

cagcggcagc agtccgtaga gtgcgaacgt gatcacggcg ccgagtatgc tgcccgtggg    540

gctggcggcc tcggccactg ccatcatcag agtgacatac agccaggcga taacaacgag    600

atacatggtc gaaccaaaaa aacgagcggg gcacgggttt tcgtggaggt ctgtgccggg    660

caaggcgggg ctcgcctggg tcacaatcaa aacggatgcc ccgcaagccc caggctattg    720

catggcatcc acgaacaagg atgcagcatg aattttgacc cactcgctgg cctgtcaggc    780

caatccgtcc agcaattctg gaacgagcaa tggagccgca cgctgcagac actgcagcag    840

atggggcaac caggccttcc gggaatccag ggcatgccag gcatgccgga catggcccag    900

gcctggaaag cggccgtccc cgaacccggc gccctgcccg agaacgcgct gtcgctggac    960

cccgaaaagc tgctggagct gcagcgccag tacctggatg gcgccaaggc catggccgaa   1020

cagggcggcg cccaggcgct gctggccaag gacaagcgct tcaataccga atcgtgggcc   1080

ggcaacccgc tgacggcggc cacggccgcc acctatctgc tcaacagccg catgctcatg   1140

ggcctggccg atgccgtgca ggccgatgac aagacgcgca accgcgtgcg cttcgccatc   1200

gagcaatggc tggcggccat ggcgcccagc aacttcctgg cactcaatgc cgaggcccag   1260
```

-continued

```
aagaaggcca tcgaaaccca gggcgagagc ctggcccagg gcgtggccaa cctgctggcc   1320
gacatgcgcc agggccatgt gtccatgacc gacgagagcc tgttcaccgt gggcaagaac   1380
gtcgccacca ccgaaggcgc cgtggtgttc gagaacgagc tgttccagct catcgaatac   1440
aagccgctga cggacaaggt gcacgagcgg cccttcctca tggtgccgcc ctgcatcaac   1500
aagttctaca tcctggacct gcagcctgac aactcgctga tccgctacgc cgtcagccag   1560
ggccatcgca ccttcgtgat gagctggcgc aaccccgacg aaagcctggc gcgcaagacc   1620
tgggacaact acatcgagga cggcgtgctc accggcatcc gcgtggcgcg cgagatcgcg   1680
ggagccgagc agatcaatgt gctgggcttt tgcgtgggcg gcaccatgct gtccaccgcg   1740
ctggcggtgc tgcaggcacg ccacgaccgc gagcatggcg cagttgctgc tccggcggcc   1800
aaggcgcctg cggccaagcg cgcggctggc agccgcagcg ccgcccgcac atccacagcc   1860
cgcgccacgg cgccggccgg cgtgccgttt cccgtggcca gcgtcacgct gctgaccacc   1920
ttcatcgact tcagcgacac cggcatcctc gatgtcttca tcgacgaatc cgtggtgcgc   1980
ttccgcgaga tgcagatggg cgagggcggc ctcatgaagg gccaggacct ggcgtccacc   2040
ttcagctttc tgcggcccaa cgacctggtc tggaactacg tggtgggcaa ctacctcaag   2100
ggcgagacgc ccccgccgtt cgacctgctg tactggaaca gcgactccac caacctgccc   2160
ggcccctact acgcctggta cctgcgcaac ctctacctgg aaaacaggct ggcccagccc   2220
ggcgcgctga ccgtctgcgg cgagcgcatc gacatgcacc agctgcgcct gccggcctat   2280
atctacggct cgcgcgagga ccacatcgtg cccgtgggcg gctcctatgc gtccacccag   2340
gtgctgggcg gcgacaagcg ttttgtgatg ggcgcgtcgg gccacatcgc gggcgtgatc   2400
aatccgccgg ccaagaaaaa gcgcagctac tggctgcgcg aggacggcca gctgcccgcc   2460
acgctcaagg agtggcaggc cggcgccgac gagtacccgg gcagctggtg ggccgactgg   2520
agcccctggc tggccgagca cggcggcaag ctggtcgcgg cgccaaagca gtacggcaag   2580
ggcagggaat acacggccat cgagccggcc ccgggccgct acgtactggt caaggcctga   2640
ggcacaatcg tttcgatgct gcagcgcaat aacgcttcgg cttgaatgca gggtgccgct   2700
gccgcgactg cggccgcgtg cgcccaggca tcccttcaag agtccaaaga aaggtccgtc   2760
atcatggaag acatcgtcat cgtttccgct gtccgtactg ccgttggcaa gtttggcggc   2820
acccttgcca agatccccgc caccgaactg ggctccatcg tgatccgcga ggcactgaac   2880
cgtgccaagg tcggcaccga tcaggtcggt gaagtcatca tgggccaggt gctggccgct   2940
ggcgcaggcc agaaccccgc acgccaggcc atgatgaagg ccggcgttgc caaggaaacc   3000
ccggccctca ccatcaacgc cgtctgcggc tcgggcctga aggccgtgat gctggcagcc   3060
caggccgtgg ccacgggcga cagcgagatc gtcgtggccg gcggccagga gaacatgagc   3120
ctgtcgcccc acgtgctgcc gggctcgcgc gacggccagc gcatgggcga ctggaagatg   3180
gccgacacca tgatcgtgga cggcctgtgg gacgtctaca accagtacca catgggcatc   3240
acggccgaga acgtggccaa ggaaaagagc gtcagccgcg agcagcagga tgccctggcc   3300
ctggccagcc agcaaaaggc cacggccgcg caggacgccg gcaagttcgt ggacgaaatc   3360
gttcccgtca gcattcccca gcgcaagggc gatcccgtgg tgttcgctgc cgacgagtac   3420
atcaaccgca agaccaatgc cgacgccctg gcaggcctgc gcccggcctt cgacaaggcc   3480
ggctcggtga cggccggcaa cgcctcgggc ctgaacgacg gcgcggccgc cgtggtggtg   3540
atgagcgcct ccaaggccaa ggccctgggc ctgacgccgc tggcgcgcat cgtctcctac   3600
```

-continued

```
gccaccagcg gcctggaccc cgccaccatg ggcctgggcc cggtgttcgc ctcgcgcaag   3660

gcgctggagc gtgcgggctg gaccgcgcag gacgtggacc tgttcgagct gaacgaagcc   3720

ttcgcggccc aggcctgtgc ggtgaaccag gagctgggca tcgacccggc caaggtcaac   3780

gtcaacggcg gcgccattgc catcggccac cccatcggcg catcgggcgc ccgcatcctg   3840

gtgaccctgc tgcacgagat gcagcgcagc ggcgccaaga agggcctggc cggcctgtgc   3900

atcggcggcg gcatgggcgt ggccatggcg gtggagcgcg tttgagaggc tccgggaaaa   3960

cgttagcaag ctt                                                      3973
```

<210> SEQ ID NO 18
<211> LENGTH: 3690
<212> TYPE: DNA
<213> ORGANISM: Methylobacterium extorquens

<400> SEQUENCE: 18

```
cgtgtccggg ttgaggctca ccccgaagcg ccgctggtag tagccggcct gggcgcggcg     60

caggccggca atgcccttgg aggcggagta gcggtcggtg cgcggcttgc cggccgtctc    120

gacgagcttc tcgatgacgt ggcggggcgc gtcgagatcg ggattgccca tgccgagatc    180

gatgatgtcg gcgccgcggg ctcgggcggc ggccttgatc cggttcacct gctcgaagac    240

gtaaggcgga aggcgcttga tgcggtggaa atcggtcatg gcgttggtct gtccggtgtc    300

gcggaactga tcctcccgcg aggatgcgtc ggcggtgagg agcctgcctg tttaccatcg    360

acgcgttcac gcgccgactt aaaaatcaac atcgcgaggc cccgccacga tcggggtgga    420

acgatcactc caccgggttg ggcgcgagcc cctgcgcggc attcttggcc gccccttccg    480

ccgcgcgccc tttggactcg ttgcggttgc gcgcgccttc cagctcggcc tgcagagcgc    540

tttgtccggc cgaattgcgg gcgcggacgg cgcgccgggg cgccgattcg cctaccggca    600

tgtagctcgc atcgctcttg cgggattgcg gccacgaaat cgggcgcctc caccggcttg    660

atgccggagc ccgccccgac catcgccgcc ttcagcggat tcacgtcgcc ggagcagccg    720

ccggtcgccg ccgcggcggc gaaaaccggc aaggcgatgg cgatggcgcg gacggtgcgg    780

cgcacgttca tgacaacggt ctgaaaatgg agtctgggat gggcgacttc tgctgggtgg    840

agcgttaatt tgtcggaaac gaggctcggg ccgccccacg gggcgggatg cgggcagacc    900

tttgggagga cgtgtcgcgt gggcaccgag cggacgaacc cggcagcgcc ggatttcgag    960

accatcgcgc gcaacgcgaa tcagctcgcg gaggtgttcc ggcaatcggc cgccgcctcg   1020

ctgaagccgt tcgagccggc gggccaggga gccctgctcc cgggcgcgaa cctccagggc   1080

gccagcgaga tcgacgagat gacccggacc ctcacgcggg tcgcggagac atggctgaag   1140

gatcccgaga aggcgcttca ggcccagacc aagctcggcc agtccttcgc cgcgctctgg   1200

gcctcgaccc tgacccggat gcagggggcc gtcaccgagc ccgtcgtcca gcccccgccc   1260

acggacaagc gcttcgccca tgccgattgg agcgcgaacc cggtcttcga cctgatcaag   1320

cagagctacc tgctccttgg ccgctgggcc gaggagatgg tcgagacggc cgaaggcatc   1380

gatgagcaca cccgccacaa ggcggagttc tacctgcgcc agctcctctc ggcctactcg   1440

ccctcgaact tcgtgatgac gaaccccgag ctcctgcgcc agacgctgga ggaggggggc   1500

gccaacctga tgcgcggcat gaagatgctg caggaggatc tggaagccgg cggcggtcag   1560

ctccgggtgc ggcagacgga cctgtccgcc ttcaccttcg gcaaggacgt ggcggtgacc   1620

cccggcgagg tcatcttccg caacgatctg atggagttga tccagtacgc gcccacgacc   1680

gagacggtgc tgaagcgtcc gctgctgatc gtgccgccct ggatcaacaa gttctacatc   1740
```

-continued

```
ctcgatctca acccgcagaa gagcctcatc ggctggatgg tgtctcaagg gatcacggtg   1800

ttcgtgatct cctgggtgaa cccggacgag cgccaccgcg acaaggactt cgagtcctac   1860

atgcgggaag gcatcgagac cgccatcgac atgatcggcg tggcgaccgg cgagaccgat   1920

gtcgcggcgg cgggctactg cgtcggcggc acgctgctcg ccgtcacgct ggcctaccag   1980

gcggcgaccg gcaaccgccg gatcaagagc gcgaccttcc tcaccacgca ggtcgatttc   2040

acccatgcgg gcgatctcaa ggtcttcgcc gacgaggggc agatcaaggc gatcgaggag   2100

cggatggccg agcacggcta cctggagggc gcgcgcatgg ccaacgcctt caacatgctc   2160

aggcccaacg acctgatctg gtcctacgtc gtcaacaact acgtacgcgg caaggcgccg   2220

gccgccttcg acctgctcta ctggaacgcc gacgccacgc ggatgcccgc ggccaaccac   2280

tcgttctacc tgcgcaactg ctacctcaac aacacgctcg ccaaggggca gatggtgctc   2340

ggcaacgtgc gcctcgacct caagaaggtg aaggtgccgg tcttcaacct cgccacccgc   2400

gaggaccaca tcgccccggc gctctcggtc ttcgaagggt cggccaagtt cggcggcaag   2460

gtcgattacg tgctggcggg ctcgggccac atcgccggcg tcgtcgcccc gccgggcccc   2520

aaggccaaat acggctttcg caccggcggc ccggcccgag gccggttcga ggattgggtc   2580

gcggcggcga cggagcatcc gggctcgtgg tggccctact ggtacaagtg gctcgaggag   2640

caggcgcccg agcgcgtgcc cgcccgcatt cctggaacgg gggccctgcc ttccctggcg   2700

ccagcaccgg gcacctatgt ccgcatgaag gcgtgagggc atgaaggtgt gagggatcga   2760

caggaaccgt gcacgcactg catcgctgtt gcggacacgg gaccgtgatt tgccttatct   2820

gatcctgggg ccggctcctg ccccaggagg atagaagcgc gttgcaacac gccaccgatc   2880

tcatttcgat catcgcgctg gggctggtct gcgcgttcat cggcggcatg ctggcccagc   2940

gaatgcggct tcccccgctc gtcggctacc tcgtcgccgg catcgccatc ggcccgttca   3000

cgccgggttt cgtcggcgat ccggctttag cgagccagct cgccgaactc ggcgtcatcc   3060

tgctgatgtt cggcgtcggg cttcacttct ccatcggtga cctactcgcg gtccgcacca   3120

tcgccctgcc cggtgcgatc gtgcagatca ccgtggcgac cgccatgggc gcgggtctcg   3180

cctggggctt cggctggggg gccggggcgg gcctcgtgtt cgggctggcg ctctcggtgg   3240

cgagcactgt cgtgctgttg cgggcgctcg aagggcaggg gcttctcgac tcggacaagg   3300

gccgcatcgc cgtcggctgg ctgatcgtcg aggatctcgc catggtggtg gccctggtgc   3360

tgctgccggc gttggcgccc tcgctcggcg gcgaggcgat gcaggccgcc ggccatcacg   3420

gcccgccgga gcacggcctg tgggtgacgc tcgggctgac gctcgccaag gtcggcgtgt   3480

tcgtcgccgt gatgcttgtc ggcgggcggc gcctcattcc ctacctgctg ggtctggccg   3540

cccgcaccgg ctcgcgcgag ctgttcaccc tggccgtgct ggcgagcgcc gtcggtatcg   3600

ccttcgcctc ctccgagctg ttcggcgtgt ccttcgccct cggcgcgttc ttcgccggga   3660

tggtgctcgc cgaatccgac ctcagccatc                                    3690
```

<210> SEQ ID NO 19
<211> LENGTH: 2712
<212> TYPE: DNA
<213> ORGANISM: Paracoccus denitrificans

<400> SEQUENCE: 19

```
gggcccgcgc gctggcgccc atccattcat tggtgttgcg gatcgtctcc atcgcatcat     60

agagagatga tccctctcaa acccttgtac gtcgtcattg caaccttctc ccatgaaccc    120
```

-continued

```
gccggattcg gccttgccgg ggaaggacac ggctttacct gcgtattgtg ctgggcataa    180

tgattttacg gttcagggag gattgtcaat tatggcgggc aaggacgaaa aaccggaagc    240

tgcgggcgcg gccgaagccg ggggcaaacc acgcaggggc cgcggggcag gggccaaggg    300

ccgtaccggg gacagcgaaa caggagccga agcctgccga ttcggaaaag ccggcgcgac    360

cgcggcgcga aaaggccgcg gtgaagaccc cgcccgagcc cgtgccggag cccgcggcgc    420

ctgccaggtc caaggcggcc gcggcctccg atcccgccaa gcctgccgcc aaggccggca    480

cacgcaaacg ccgcgttgcg cgcgggcggg ggccggtcgc agcgatccgc gccccggtcc    540

gcgccgaaag ccctcgggca aggccgccgc gaaggcgcag gccgagaccg cctcgctcag    600

tatggccgac gaggcgctgc gtccgctggg cgccgtcgga ccgggcggcg gcgtgccgcc    660

catggccgcg ccccgcgccc aggctgccgc cccggcgggg accggccagt ctgccggact    720

cgctgccgag ccgcatccag cccgaacacc gccgccttcg tcgaggcggc cttcggtccc    780

ggcagccgcc tcccaacagc tggcccagaa catcgagcgc atcgaatcgc tgacccagcg    840

cctgatcagc gcgctggcgc agcgccgtcc ctcgaatccc ggcgtcgaga tgccgggccc    900

cgaccttttc gccaccgcga cctcggcctg gatcaagctt ctggccgagc agcccgagcg    960

ggtgatcggc cagcaggtca gctattgggg cgaaaccttg cgccatttcg ccgaggccca   1020

ggccgccttt gcccgcggca ccgtgacgcc gccgcccagc gaagggccgc gggaccggcg   1080

ctttgccaac ccgctgtggg aggcgcatcc cttcttcaac ttcatcaagc ggcaatacca   1140

gatcaacgcc caggccctgc aggaggcggc cagcacactg gacctgcccg agatgaccga   1200

ccggcgccgg atcgaatggt tcacccgcca gatgatcgac atgatggcgc cgacgaattt   1260

tctggccacc aatcccgacg acagctggaa aaggcgctgg agaccgaggg acgaaagcct   1320

ggtcaggggc cttgagaacc tggtgcgcga cgtcgagcag aacagcggcg agctgatcgt   1380

gtcgctggcc gaccgcgatg ccttccgtgt gggcgagaac atcggcacca ccgagggcac   1440

ggtggtcgcg cgcaccaagc tttacgagct gatccagtac aagcccacca ccgcgcaggt   1500

gcatgagatc ccgctggtga tctttccgcc ctggatcaac aaattctaca tcctcgacct   1560

caagccgcag aacagcctga tcaaatggat cgtggaccag ggccatacgc tgttcgtggt   1620

ggcctggaag aaccccgacc ccagctatgg cgacaccggc atggacgatt acgtcagcgc   1680

ctatctggag gtgatggacc gggttctgga tctgaccgac cagaaaaagc tgaatgcggt   1740

gggctattgc atcgccggca ccaccctggc gctgacccct gtcgtgctga agcagcgcgg   1800

cgacgaccgg gtgaacgcgg ccaccttctt caccgcgctg accgatttcg ccgaccaggg   1860

cgagttcact gcctatctgc aggaggattt cgtctcaggc atcgaggagg aggcggcgcg   1920

gaccggcatc ctgggcgcgc agctgatgac gcgcaccttc agcttcctgc gcgccaacga   1980

cctggtctgg gggccggcga tccgcagcta catgctgggc gagacgccgc cggccttcga   2040

cctgctgttc tggaacggcg acggcaccaa cctgcccggg cgcatggccg tggaatacct   2100

gcgcggcctg tgccagcaga accgcttcgt caaggagggg ttcgatctga tgggccaccg   2160

cctgcatgtc ggcgacgtga ccgtgccgct ttgcgccatc gcctgcgaga ccgaccatat   2220

cgcgccctgg aaggacagct ggcgcggcat cgcgcagatg ggctccaggg acaagacctt   2280

catcctgtcc gaatcgggcc atatcgccgg catcgtcaac ccgcccagca agaagaaata   2340

cggccattat acctcggacg ccggtttcgg tcagggcgag cagcactggc tggacaaggc   2400

cagccatcac gagggcagct ggtggggccg ctggggcgaa tggctggccc ggcgggcggg   2460

gggcatggtc gatgcccgcg acccgggcga gggcttcggc cctgcgccgg gcctttacgt   2520
```

ccacgagcgg gcgtaaaatt tttctgcacc gcagcaagaa aaccttgcaa tgctgcggtg 2580
cagaaagtat atgttggaca gaacagttca accggtgccg aagcttcgcg ccgacctagg 2640
agagagcaaa tggccaagac ccctgacttt accaagacca tgcaagaagt tatggcgaaa 2700
ttcccggtcg ac 2712

<210> SEQ ID NO 20
<211> LENGTH: 2587
<212> TYPE: DNA
<213> ORGANISM: Zoogloea ramigera

<400> SEQUENCE: 20
gtcgacctgg gcaaggtcgg gccgcagcaa gtgcccgagg cggacgccag catgaccacc 60
atcgccggca aggtgtgctg gtgatgacgg ccgactgcct gccggtgctg ttttgcgaca 120
cgcgcggcac cgttcgtggc tgccgcccac gccggtcggc gcggcctggc cgctggcgtg 180
ctggaaaaca cctacgcgag cagtgcgcgt ccgcggcgcc ggcgactgat ggcctggatg 240
gggccggcca tcggcgccta ccagttcgag gtgggcggcg atgtgcgcca ggcctttctg 300
caaaccgcac ctgacgattc aagcgtgcgg cacgtgacgg cagcgtttac gccactcgaa 360
caccggccgg gcaagttcct ggccgacatc tacgcgctgg cccggcatcg catgctgcgc 420
gccggcgtgg cgcaagtgca tggcggcgaa tactgcacgg tggccaattc cgggcgcttc 480
tattcgttcc gtcgcgacgg cgtcaccgga cgccaggcaa gtttgatctg gctcaaataa 540
gtatcaggta gggggcgctg gactttttag cgtctcgcgc cgcctgtcgc gctttgcggc 600
gtgctttctc ttgcccgttc ccgcgatgta aatcaaggtc cccagcggca gcacgcaata 660
gaacaaaaac gcaatagcaa caatcagcat gtagcaaccc aggttaagag atattcaata 720 ttttttttagg gaatcacaca tgaatttgcc cgatccgcaa gccattgcca acgcctggat 780
gtcccaggtg ggcgacccca gccaatggca atcctggttc agcaaggcgc ccaccaccga 840
ggcgaacccg atggccacca tgttgcagga tatcggcgtt gcgctcaaac cggaagcgat 900
ggagcagctg aaaaacgatt atctgcgtga cttcaccgcg ttgtggcagg attttttggc 960
tggcaaggcg ccagccgtcc agcgaccgcg cttcagctcg gcagcctggc agggcaatcc 1020
gatgtcggcc ttcaatgccg catcttacct gctcaacgcc aaattcctca gtgccatggt 1080
ggaggcggtg gacaccgcac cccagcaaaa gcagaaaata cgctttgccg tgcagcaggt 1140
gattgatgcc atgtcgcccg cgaacttcct cgccaccaac ccggaagcgc agcaaaaact 1200
gattgaaacc aagggcgaga gcctgacgcg tggcctggtc aatatgctgg gcgatatcaa 1260
tatgctgggc gatatcaaca acggccatat ctcgctgtcg gacgaatcgg cctttgaagt 1320
gggccgcaac ctggccatta ccccgggcac cgtgatttac gaaaatccgc tgttccagct 1380
gatccagtac acgccgacca cgccgacggt cagccagcgc ccgctgttga tggtgccgcc 1440
gtgcatcaac aagttctaca tcctcgacct gcaaccggaa aattcgctgg tgcgctacgc 1500
ggtggagcag ggcaacaccg tgttcctgat ctcgtggagc aatccggaca agtcgctggc 1560
cggcaccacc tgggacgact acgtggagca gggcgtgatc gaagcgatcc gcatcgtcca 1620
ggacgtcagc ggccaggaca agctgaacat gttcggcttc tgcgtgggcg gcaccatcgt 1680
tgccaccgca ctggcggtac tggcggcgcg tggccagcac ccggcggcca gcctgaccct 1740
gctgaccacc ttcctcgact tcagcgacac cgggtgctcg acgtcttgtc gagaaaccca 1800
ggtcgcgctg cgtgaacagc aattgcgcga tggcggcctg atgccgggcc gtgacctggc 1860

-continued

```
ctcgaccttc tcgagcctgc gtccgaacga cctggtatgg aactatgtgc agtcgaacta   1920

cctcaaaggc aatgagccgg cggcgtttga cctgctgttc tggaattcgg acagcaccaa   1980

tttgccgggc ccgatgttct gctggtacct gcgcaacacc tacctggaaa acagcctgaa   2040

agtgccgggc aagctgacgg tggccggcga aaagatcgac ctcggcctga tcgacgcccc   2100

ggccttcatc tacggttcgc gcgaagacca catcgtgccg tggatgtcgg cgtacggttc   2160

gctcgacatc ctgaaccagg gcaagccggg cgccaaccgc ttcgtgctgg gcgcgtccgg   2220

ccatatcgcc ggcgtgatca actcggtggc caagaacaag cgcacgtact ggatcaacga   2280

cggtggcgcc gccgatgccc aggcctggtt cgatggcgcg caggaagtgc cgggcagctg   2340

gtggccgcaa tgggccgggt tcctgaccca gcatggcggc aagaaggtca agcccaaggc   2400

caagcccggc aacgcccgct acaccgcgat cgaggcggcg cccggccgtt acgtcaaagc   2460

caagggctga ccacggggaa ctgccagact accggactcg gctattggaa gcgttgcaat   2520

aaatgccagc actattgcga gtttctgcaa tctttctact ttcccctcta taataggatc   2580

cgtcgac                                                             2587
```

```
<210> SEQ ID NO 21
<211> LENGTH: 3187
<212> TYPE: DNA
<213> ORGANISM: Aeromonas caviae

<400> SEQUENCE: 21

agatctggac cggggtgctg gcctgggcca cgccggcgag ggccagcgcg gagcaaccga     60

gcagcagggc gagaggtttc atcgggattc cttggcagtc tgaatgacgt gccagcctat    120

cagcgcggcg ccggtgcggc gagggcgcgc cggacccagt gcgtcacctc tcgtctgatc    180

cgcctccctc gacgggcgtc gctgacaaaa aaattcaaac agaaattaac atttatgtca    240

tttacaccaa accgcatttg gttgcagaat gctcaaacgt gtgtttgaac agagcaagca    300

acacgtaaac agggatgaca tgcagtaccc gtaagaaggg ccgattggcc cacaacaaca    360

ctgttctgcc gaactggaga ccgatgatga atatggacgt gatcaagagc tttaccgagc    420

agatgcaagg cttcgccgcc cccctcaccc gctacaacca gctgctggcc agcaacatcg    480

aacagctgac ccggttgcag ctggcctccg ccaacgccta cgccgaactg ggcctcaacc    540

agttgcaggc cgtgagcaag gtgcaggaca cccagagcct ggcggccctg ggcacagtgc    600

aactggagac cgccagccag ctctcccgcc agatgctgga tgacatccag aagctgagcg    660

ccctcggcca gcagttcaag gaagagctgg atgtcctgac cgcagacggc atcaagaaaa    720

gcacgggcaa ggcctgataa cccctggctg cccgttcggg cagccacatc tccccatgac    780

tcgacgctac gggctagttc ccgcctcggg tgtgggtgaa ggagagcaca tgagccaacc    840

atcttatggc ccgctgttcg aggccctggc ccactacaat gacaagctgc tggccatggc    900

caaggcccag acagagcgca ccgcccaggc gctgctgcag accaatctgg acgatctggg    960

ccaggtgctg gagcagggca gccagcaacc ctggcagctg atccaggccc agatgaactg   1020

gtggcaggat cagctcaagc tgatgcagca caccctgctc aaaagcgcag gccagccgag   1080

cgagccggtg atcaccccgg agcgcagcga tcgccgcttc aaggccgagg cctggagcga   1140

acaacccatc tatgactacc tcaagcagtc ctacctgctc accgccaggc acctgctggc   1200

ctcggtggat gccctggagg gcgtccccca gaagagccgg gagcggctgc gtttcttcac   1260

ccgccagtac gtcaacgcca tggcccccag caacttcctg gccaccaacc ccgagctgct   1320

caagctgacc ctggagtccg acggccagaa cctggtgcgc ggactggccc tcttggccga   1380
```

```
ggatctggag cgcagcgccg atcagctcaa catccgcctg accgacgaat ccgccttcga   1440

gctcgggcgg gatctggccc tgaccccggg ccgggtggtg cagcgcaccg agctctatga   1500

gctcattcag tacagcccga ctaccgagac ggtgggcaag acacctgtgc tgatagtgcc   1560

gcccttcatc aacaagtact acatcatgga catgcggccc cagaactccc tggtcgcctg   1620

gctggtcgcc cagggccaga cggtattcat gatctcctgg cgcaacccgg gcgtggccca   1680

ggcccaaatc gatctcgacg actacgtggt ggatggcgtc atcgccgccc tggacggcgt   1740

ggaggcggcc accggcgagc gggaggtgca cggcatcggc tactgcatcg gcggcaccgc   1800

cctgtcgctc gccatgggct ggctggcggc gcggcgccag aagcagcggg tgcgcaccgc   1860

caccctgttc actaccctgc tggacttctc ccagcccggg gagcttggca tcttcatcca   1920

cgagcccatc atagcggcgc tcgaggcgca aaatgaggcc aagggcatca tggacgggcg   1980

ccagctggcg gtctccttca gcctgctgcg ggagaacagc ctctactgga actactacat   2040

cgacagctac ctcaagggtc agagcccggt ggccttcgat ctgctgcact ggaacagcga   2100

cagcaccaat gtggcgggca agacccacaa cagcctgctg cgccgtctct acctggagaa   2160

ccagctggtg aagggggagc tcaagatccg caacacccgc atcgatctcg gcaaggtgaa   2220

gacccctgtg ctgctggtgt cggcggtgga cgatcacatc gccctctggc agggcacctg   2280

gcagggcatg aagctgtttg gcggggagca gcgcttcctc ctggcggagt ccggccacat   2340

cgccggcatc atcaacccgc cggccgccaa caagtacggc ttctggcaca acggggccga   2400

ggccgagagc ccggagagct ggctggcagg ggcgacgcac cagggcggct cctggtggcc   2460

cgagatgatg ggctttatcc agaaccgtga cgaagggtca gagcccgtcc ccgcgcgggt   2520

cccggaggaa gggctggccc ccgcccccgg ccactatgtc aaggtgcggc tcaaccccgt   2580

gtttgcctgc ccaacagagg aggacgccgc atgagcgcac aatccctgga agtaggccag   2640

aaggcccgtc tcagcaagcg gttcggggcg gcggaggtag ccgccttcgc cgcgctctcg   2700

gaggacttca accccctgca cctggacccg gccttcgccg ccaccacggc gttcgagcgg   2760

cccatagtcc acggcatgct gctcgccagc ctcttctccg ggctgctggg ccagcagttg   2820

ccgggcaagg ggagcatcta tctgggtcaa agcctcagct tcaagctgcc ggtctttgtc   2880

ggggacgagg tgacggccga ggtggaggtg accgcccttc gcgaggacaa gcccatcgcc   2940

accctgacca cccgcatctt cacccaaggc ggcgccctcg ccgtgacggg ggaagccgtg   3000

gtcaagctgc cttaagcacc ggcggcacgc aggcacaatc agcccggccc ctgccgggct   3060

gattgttctc cccgctccg cttgcccccct ttttcggggc aatttggccc aggccctttc   3120

cctgccccgc ctaactgcct aaaatggccg ccctgccgtg taggcattca tccagctaga   3180

ggaattc                                                              3187
```

<210> SEQ ID NO 22
<211> LENGTH: 2535
<212> TYPE: DNA
<213> ORGANISM: Rattus norvegicus

<400> SEQUENCE: 22

```
gagcagtacc ccggccactg ccagtgtgtg cgtggtgcag gatagactca tggcttcgcc     60

tctgaggttc gacgggcgtg tggtcctggt caccggcgcc gggggagggt tgggcagagc    120

ttatgccctg gcttttgcag aaagaggagc attagttgtt gtgaatgact taggagggga    180

cttcaaaggc gttgggaaag gctcttctgc cgcagacaag gtcgtggaag aaataagaag    240
```

-continued

```
gagaggcggg aaagcggtgg ccaattacga ttcaggcgaa gcaggcgaga agcttgtgaa    300
gacagcactg gacacattcg gcagaataga tgttgtggtg aacaatgctg ggatcctgag    360
ggaccgttcc ttctctagga taagtgatga agactgggat ataattcaaa gagttcattt    420
gcggggctcc ttccaagtga cccgggcagc atgggatcat atgaagaagc agaattatgg    480
aagaatcatt atgacggcct cagcttctgg aatatacagc aactttggcc aggcaaatta    540
tagtgctgca aagctgggcc ttctgggtct cgccaatact ctcgtgattg aaggcaggaa    600
gaacaacatt cattgtaaca ccattgcccc aaacgctggg tcacggatga cagagacggt    660
gatgccagaa gacctcgttg aagccctgaa gccagagtat gtggcaccgc tggtcctttg    720
gctttgccat gagagctgtg aggaaaatgg tggcttgttt gaggttggag caggatggat    780
tggaaaattg cgctgggaga ggaccctggg agccattgtc aggaagcgga atcagcccat    840
gactcccgag gcagtgaggg acaactgggt gaagatctgt gacttcagca atgccagcaa    900
gccgaagagc attcaagagt ccacaggtgg tataatcgaa gttttacata aaatagattc    960
agaaggaatc tcacaaaatc acaccggtca agtggcatct gcagatgcat caggatttgc   1020
tggcgtcgtt ggccacaaac ttccttcatt ttcttcttca tatacggaac tgcagtgcat   1080
tatgtatgcc ctcggagtag gagcttcagt caaaaatcca aaggacttga agtttgttta   1140
tgaagggagt gctgacttct cctgtttgcc tacatttgga gtcattgtcg ctcagaagtc   1200
cttgacgagt ggaggcttag cagaggttcc tgggctgtca atcaactttg caaaggttct   1260
tcatggggag cagtacttgg agttgtataa gccacttccc cgatcagggg aattaaaatg   1320
tgaagcagtt attgctgaca tcctggataa aggctctggc atagtgattg ttatggacgt   1380
ctattcttat tctggcaagg aacttatatg ctataatcag ttctctgtct tcgttgttgg   1440
ctctggaggc tttggtggaa aacggacatc agaaaaactc aaagcagctg tagccgtacc   1500
ggatcggcct ccagatgctg tactgagaga taccacttca ctgaatcagg ccgctctgta   1560
ccgcctcagt ggagactcga atcctttaca cattgacccg agctttgcga gcattgccgg   1620
ttttgagaaa cccatattac acggattatg tacttttggg ttttctgcaa ggcatgtttt   1680
acagcagttt gcggataatg atgtgtcaag attcaaggcc attaaggttc gttttgccaa   1740
accagtgtat ccaggacaaa ctctacaaac tgagatgtgg aaggaaggaa acagaattca   1800
ttttcaaacc aaggtccaag agactggaga cattgtcatt tccaatgcat atgtggatct   1860
tgttcctaca tctggagttt ccgctcagac accttctgag ggtggagcac tgcagagtgc   1920
tcttgtattt ggggaaatag gtcgacgcct caaggatgtt ggacgtgagg tggtaaagaa   1980
agtaaatgct gtatttgaat ggcatatcac gaaaaatggg aatgttgcag ccaagtggac   2040
cattgacctg aagaacggct ctggagaggt ttaccaaggc cctgccaaag gctctgctga   2100
cacgaccatc acaatttctg atgaggattt catggaagtg gtcctgggca agcttaaccc   2160
acagaatgcc ttcttcagtg gcagactgaa ggcccgagga aacatcatgc tgagccagaa   2220
gctacagatg attctgaaag actatgccaa gctctgaagg acccactgcg tgctttaata   2280
aaaccagaat cattacgttc tgtctacgca gtcatgctcc agccttcttt gaaacgatcc   2340
acggtaatgt gcagcagaaa tcgcttaaca ttttcagatt cagataactt tcagattttc   2400
attttctact aatttttcac atattatttt tataaggaac tgtaatctag ctagcaaata   2460
attgttctgt tcatagatct gtatcttaat aaaaaaaaag tcaaccgaaa aaaaaaaaaa   2520
aaaaaaaaaa aaaaa                                                    2535
```

<210> SEQ ID NO 23
<211> LENGTH: 2328
<212> TYPE: DNA
<213> ORGANISM: Ralstonia eutropha

<400> SEQUENCE: 23

```
ctgcaggttc cctcccgttt ccattgaaag gactacacaa tgactgacgt tgtcatcgta      60

tccgccgccc gcaccgcggt cggcaagttt ggcggctcgc tggccaagat cccggcaccg     120

gaactgggtg ccgtggtcat caaggccgcg ctggagcgcg ccggcgtcaa gccggagcag     180

gtgagcgaag tcatcatggg ccaggtgctg accgccggtt cgggccagaa ccccgcacgc     240

caggccgcga tcaaggccgg cctgccggcg atggtgccgg ccatgaccat caacaaggtg     300

tgcggctcgg gcctgaaggc cgtgatgctg gccgccaacg cgatcatggc gggcgacgcc     360

gagatcgtgg tggccggcgg ccaggaaaac atgagcgccg ccccgcacgt gctgccgggc     420

tcgcgcgatg gtttccgcat gggcgatgcc aagctggtcg acaccatgat cgtcgacggc     480

ctgtgggacg tgtacaacca gtaccacatg ggcatcaccg ccgagaacgt ggccaaggaa     540

tacggcatca cacgcgaggc gcaggatgag ttcgccgtcg gctcgcagaa caaggccgaa     600

gccgcgcaga aggccggcaa gtttgacgaa gagatcgtcc cggtgctgat cccgcagcgc     660

aagggcgacc cggtggcctt caagaccgac gagttcgtgc gccagggcgc cacgctggac     720

agcatgtccg gcctcaagcc cgccttcgac aaggccggca cggtgaccgc ggccaacgcc     780

tcgggcctga acgacggcgc cgccgcggtg gtggtgatgt cggcggccaa ggccaaggaa     840

ctgggcctga ccccgctggc cacgatcaag agctatgcca acgccggtgt cgatcccaag     900

gtgatgggca tgggcccggt gccggcctcc aagcgcgccc tgtcgcgcgc cgagtggacc     960

ccgcaagacc tggacctgat ggagatcaac gaggcctttg ccgcgcaggc gctggcggtg    1020

caccagcaga tgggctggga cacctccaag gtcaatgtga acggcggcgc catcgccatc    1080

ggccacccga tcggcgcgtc gggctgccgt atcctggtga cgctgctgca cgagatgaag    1140

cgccgtgacg cgaagaaggg cctggcctcg ctgtgcatcg gcggcggcat gggcgtggcg    1200

ctggcagtcg agcgcaaata aggaaggggt tttccggggc cgcgcgcggt tggcgcggac    1260

ccggcgacga taacgaagcc aatcaaggag tggacatgac tcagcgcatt gcgtatgtga    1320

ccggcggcat gggtggtatc ggaaccgcca tttgccagcg gctggccaag gatggctttc    1380

gtgtggtggc cggttgcggc cccaactcgc cgcgccgcga aaagtggctg gagcagcaga    1440

aggccctggg cttcgatttc attgcctcgg aaggcaatgt ggctgactgg gactcgacca    1500

agaccgcatt cgacaaggtc aagtccgagg tcggcgaggt tgatgtgctg atcaacaacg    1560

ccggtatcac ccgcgacgtg gtgttccgca agatgacccg cgccgactgg gatgcggtga    1620

tcgacaccaa cctgacctcg ctgttcaacg tcaccaagca ggtgatcgac ggcatggccg    1680

accgtggctg gggccgcatc gtcaacatct cgtcggtgaa cgggcagaag ggccagttcg    1740

gccagaccaa ctactccacc gccaaggccg gcctgcatgg cttcaccatg gcactggcgc    1800

aggaagtggc gaccaagggc gtgaccgtca acacggtctc tccgggctat atcgccaccg    1860

acatggtcaa ggcgatccgc caggacgtgc tcgacaagat cgtcgcgacg atcccggtca    1920

agcgcctggg cctgccggaa gagatcgcct cgatctgcgc ctggttgtcg tcggaggagt    1980

ccggtttctc gaccggcgcc gacttctcgc tcaacggcgg cctgcatatg ggctgacctg    2040

ccggcctggt tcaaccagtc ggcagccggc gctggcgccc gcgtattgcg gtgcagccag    2100

cgcggcgcac aaggcggcgg gcgtttcgtt tcgccgcccg tttcgcgggc cgtcaaggcc    2160
```

-continued

```
cgcgaatcgt ttctgcccgc gcggcattcc tcgctttttg cgccaattca ccgggttttc   2220

cttaagcccc gtcgcttttc ttagtgcctt gttgggcata gaatcagggc agcggcgcag   2280

ccagcaccat gttcgtgcag cgcggccctc gcgggggcga ggctgcag                2328


<210> SEQ ID NO 24
<211> LENGTH: 1462
<212> TYPE: DNA
<213> ORGANISM: Raphanus sativus

<400> SEQUENCE: 24

gactagtcgc gcgctctctg aactgaagta caagatttcc cgatggccca ttcagcagat     60

tcctccgaca atcccagaga tgtttgcatc gtgggtgttg cacgcactcc tatgggtggc    120

tttctcggat ctctctcctc cttacccgcc acaaagcttg gatcccttgc catcacagct    180

gctctgaaga gagaaatgtt gacccgtctc tggtccaagg aagttgtgtt tgggaatgtt    240

ctcagtgcta atttgggtca agctcccgct cgtcaggccg ctttaggtgc tgggatctct    300

aactctgtta tctgtaccac tgtcaacaag gtctgtgcct caggcatgaa agctgtgatg    360

attgctgctc agagtatcca gctggggatc aatgatgtag tcgtggcggg tggtatggaa    420

agcatgtcta atacaccaaa gtatcttgca gaagcaagaa aaggatctag gtttggtcat    480

gattctctcg tagatgggat gcttaaggat ggactgtggg atgtctataa cgactgtggg    540

atgggaagct gtgcagagtt atgcgctgag aagtttgaga taaccaggga gcagcaagat    600

gattacgctg ttcagagctt tgagcgtggt attgctgctc aggaatctgg cgccttcaca    660

tgggagatcg tcccggttga agtttctgga ggaaggggta ggccatcaac cattgttgac    720

aaggatgaag gtcttgggaa gtttgatgct gcaaaactga ggaaactccg tccgagtttc    780

aaggagaatg gaggcacagt tacagctgga aatgcctcta gcataagtga tggtgcagct    840

gctattgtcc tagtgagtgg agagaaggcg cttcagctag gacttcaagt acttgcaaaa    900

gttaaaggtt atggtgatgc agctcaggag ccagagtttt tcactactgc tcctgctctg    960

gcaataccaa aagctattgc acccaattcg ccctatagtg agtcgtatca agttgattac   1020

tatgagatca atgaagcatt tgcagttgta gcacttgcaa atcaaaagct acttgggatt   1080

agtccggaga aggtgaatgt aaatggagga gccgtctcct taggacatcc tctaggctgc   1140

agtggagccc gtattctaat cacattgctt gggatactga agaagagaaa cggcaagtac   1200

ggtgtgggag gagtgtgcaa cggaggagga ggtgcttctg ctcttgttct tgaagtcgtg   1260

tgatgcattt atatgaatcc caggttgttg aactatatag agcgtatcta ctatcattct   1320

accaacttgc acttcaagtt tgatattggt tggtctctct caataaatga gtgatgatga   1380

tctttgatgt tgttaagttt atttagttat attatatgaa aactatgttt ctgttaaaaa   1440

aaaaaaaaaa aaaaaaaaaa ac                                            1462


<210> SEQ ID NO 25
<211> LENGTH: 1440
<212> TYPE: DNA
<213> ORGANISM: Pichia membranifaciens

<400> SEQUENCE: 25

atggcactcg tcctgcgcag gttcttctcc ggctccgtgg ccagggccac ggcgccagcc     60

agcctgatca agctccaccc ggtctcgcag ctcaaacaga gacagctgcc cacctacgtg    120

ggccagtcga actcgatcgt gaagtcgctg gtgtggacca cgccgcccag caacgtgctc    180

attgtgaaga agccgtggca ctccaaggtg ctcgacgccg ccatcacctt catcaagcat    240
```

```
ctccacgcaa actacccgtc cgtgaacatc atcgtggtgc ccgaggtcgc cgaggagctc    300

aactcgatcg aacgcaagag ctccgaccca gacacgccca tcggcatcta cacaggcccg    360

ctcaacgaga tcatctccaa gacagacctc attgtctccc tcggcggaga cggcaccatc    420

ctccggggcg tgtcgctctt ctccaacacg acggtcccac ccgtcttgtc cttctccctc    480

ggcacactag ggttccttct cccgttcgac ttcaacaact acgcggaggc gttcaaacag    540

atgttcgagt cccgctccag catcctcaaa agagaacgca tagagtgcca catcgtcaag    600

gctagcccgc aatcggaggc gctcaaccag cagcggaagg acctcgaaac gtcctaccag    660

aacacacgct ccctaaacgc acaagaagag gtggaaaggt tgaagcgctt gtccgcagcc    720

atggatgctc cgttcgacaa tctgacagtc tcctccgagc tcgaggccct caagaaattg    780

aaaatccacg ccatgaacga cattgtcctc cacagaggct ctctcccggg attggtcaac    840

ctcgacgtct acatcaacgg caacctactc acacggacaa ccgcagacgg cctcatcttt    900

gccaccccaa caggctccac agcgtactct ctttcggcag gcggttccat cgtccaccca    960

gtcgtcaagt gcatccttct caccccgatc tgtccgcgaa gcttgtcctt caggcccttg   1020

atcctcccac taaactccca tatcttgatc aaggtcatcg gcaaggaaaa cgtgaagatc   1080

gactacacca agtgcaacgc caaattgagc atagacggaa ttccgcaact gaaaatggtc   1140

cccggcgacg agatccacat catctccgag tccgtctcca gacttaactc cgtaaacgac   1200

gacgaagacg acatcgcctc cggaacaact gcagacgcac cggactgcgt caatgcttcc   1260

actactgtct cgaaggaatc taagacgaag tctctgggaa gacgccgtgg cgtccaaaag   1320

agaaccgccg aacgaagtgg cgtctggtgt gttgtccaga gtaagggcga ctgggtcaac   1380

ggcatcaacg gaatgttggg attcaaccta ggattcaagt cttccaagtc caacaaatga   1440
```

```
<210> SEQ ID NO 26
<211> LENGTH: 3967
<212> TYPE: DNA
<213> ORGANISM: Saccharomyces cerevisiae

<400> SEQUENCE: 26

gatcaattct gttaagctct ttacgcatgc ttttattttc ttcactttgg cacattcgct     60

aaagagaaag cgtttgatag ccgcttttgc gatttggtcc tatggtatct ttacactatt    120

catcaatcaa aaaatgaaaa atctcccctt taataatatt gctatcatcc taagtcccat    180

ggatcaatgg tataagggta tcgttcctcg atgggatttt tttttcaatt ttacattatt    240

gcgtttgtta agttactcca tggatttttt ggaaagatgg catgaacaat tgagccgcca    300

accttcgata gattacgatg atagacgacc tgaattcaga aaaagtttat ctggttctac    360

tctacaaacc atttatgagt caggtaagaa tgttctggag gaaaaggaac gactggtagc    420

agaacatcac atccaggatt acaactttat caattttatc gcttatatta cttacgcgcc    480

attgttttta gtgggcccaa ttatcacttt taatgactac ctttatcaat cagaaaataa    540

gcttccttcg ctaacgaaaa aaaacatagg cttctatgcc ctcaaagtat tttcgagttt    600

gcttttgatg gaaattatcc tacattatat ctatgtgggt gcaatagcaa ggaccaaggc    660

atggaacaat gatacaccct tgcaacaggc tatgatcgcg ctgttcaact tgaacattat    720

gtatttaaaa cttttgatcc catggaggct ctttcggctg tgggccatgg tcgatggtat    780

tgatgcacct gaaaatatgc tacgatgtgt ggataataat tatagtacag tgggattctg    840

gagagcctgg catacaagtt ttaacaagtg ggtaatccgt tacatctatg ttccatttgg    900
```

-continued

```
cgggtccaat aacaaaatat taacgagctt tgccgtattc tcatttgtag caatatggca     960
tgacatccaa ttacgagtgt tgttttgggg gtggttaaca gtccttttat tattaggcga    1020
aacctacatt actaactgtt ttagtagata tagattcaga agctggtaca ggtttgtttg    1080
cggtatcggt gctgcaataa atatttgcat gatgatgatt attaatgtct atggattttg    1140
cttgggtgca gagggaacga agcttctatt gaagggcata tttaacaatt cacatagtcc    1200
ggagtttttg actgcggtaa tggtaagcct atttattgct gttcaggtaa tgtttgagat    1260
tagagaagaa gaaaaaagac atggcatcaa cttgaaatgt tgatctagtt attagataag    1320
ctatgaaagt caatcctttt aatcgagaat gtaaatatgt ggaatacaca attttaacca    1380
aagtactata tatgcgttac aagtaattta aatttaagtt caccgaagta aaactaactg    1440
caagattgtt acaaagaaca atgcactatt taaatcacac aatggctatt gaaaactgta    1500
actgtcagaa atgctgcatg tatctatatg catcactaag ttgcgacttt taagaaactt    1560
ccacagttct caactcttct ttgtgctttt cacacatttt cacaattttc cgaaatctcc    1620
aaattgaaaa aaaaataaaa ataaaaaaag gcaggagaag actaagtatt cattattcgc    1680
tgtttcataa ataaaaggat aaaaaggtta aggatactga ttaaaatgtt tgtcagggtt    1740
aaattgaata aaccagtaaa atggtatagg ttctatagta cgttggattc acattcccta    1800
aagttacaga gcggctcgaa gtttgtaaaa ataaagccag taaataactt gaggagtagt    1860
tcatcagcag atttcgtgtc cccaccaaat tccaaattac aatctttaat ctggcagaac    1920
cctttacaaa atgtttatat aactaaaaaa ccatggactc catccacaag agaagcgatg    1980
gttgaattca taactcattt acatgagtca taccccgagg tgaacgtcat tgttcaaccc    2040
gatgtggcag aagaaatttc ccaggatttc aaatctcctt tggagaatga tcccaaccga    2100
cctcatatac tttatactgg tcctgaacaa gatatcgtaa acagaacaga cttattggtg    2160
acattgggag gtgatgggac tattttacac ggcgtatcaa tgttcggaaa tacgcaagtt    2220
cctccggttt tagcatttgc tctgggcact ctgggctttc tatcaccgtt tgattttaag    2280
gagcataaaa aggtctttca ggaagtaatc agctctagag ccaaatgttt gcatagaaca    2340
cggctagaat gtcatttgaa aaaaaaggat agcaactcat ctattgtgac ccatgctatg    2400
aatgacatat tcttacatag gggtaattcc cctcatctca ctaacctgga cattttcatt    2460
gatggggaat tttgacaag aacgacagca gatggtgttg cattggccac tccaacgggt     2520
tccacagcat attcattatc agcaggtgga tctattgttt ccccattagt ccctgctatt    2580
ttaatgacac caatttgtcc tcgctctttg tcattccgac cactgatttt gcctcattca    2640
tcccacatta ggataaagat aggttccaaa ttgaaccaaa aaccagtcaa cagtgtggta    2700
aaactttctg ttgatggtat tcctcaacag gatttagatg ttggtgatga aatttatgtt    2760
ataaatgagg tcggcactat atacatagat ggtactcagc ttccgacgac aagaaaaact    2820
gaaaatgact ttaataattc aaaaaagcct aaaaggtcag ggatttattg tgtcgccaag    2880
accgagaatg actggattag aggaatcaat gaacttttag gattcaattc tagctttagg    2940
ctgaccaaga gacagactga taatgattaa acgctctgaa tgcaaagatt caatgagatt    3000
ctctaagaat tctattgata agatttaaag gtatttgaca agtagagatc tttatttttt    3060
cttgcatttt gtctagagaa atctcaactg acatactcga catgaaattt ttggtattgt    3120
gtcttttatt ctattgcttt aagaaaactg tgacatatag ggaagacatg cttaacaaga    3180
agatataatt atataatata tatattatta ataataacat ccttactgca gtcctgttgt    3240
gggagaaaat ggagagagac tatgtttcgt atcaattcct aaaatcaaaa aaaaaaaaaa    3300
```

-continued

```
aaaaaagtta aacaagcact cgctgttcat ttgttttaca agtattcata ctctaatagg   3360

tcattgagct tcttttcttg aggagagatc caatttgaag tcggaataag atttgctttc   3420

attagcgtag gcaataatta tgagataaat ggtgcagcac tattaagtag tgtggatttc   3480

aataatttcc gaattaggaa taaatgcgct aaatagacat cccgttctct ttggtaatct   3540

gcataattct gatgcaatat ccaacaacta tttgtgcaat tatttaacaa aatccaatta   3600

actttcctaa ttagtccttc aatagaacat ctgtattcct ttttttatg aacaccttcc   3660

taattaggcc atcaacgaca gtaaattttg ccgaatttaa tagcttctac tgaaaaacag   3720

tggaccatgt gaaaagatgc atctcattta tcaaacacat aatattcaag tgagccttac   3780

ttcaattgta ttgaagtgca agaaaaccaa aaagcaacaa caggttttgg ataagtacat   3840

atataagagg gccttttgtt cccatcaaaa atgttactgt tcttacgatt catttacgat   3900

tcaagaatag ttcaaacaag aagattacaa actatcaatt tcatacacaa tataaacgat   3960

taaaaga                                                              3967
```

<210> SEQ ID NO 27
<211> LENGTH: 1728
<212> TYPE: DNA
<213> ORGANISM: *Saccharomyces cerevisiae*

<400> SEQUENCE: 27

```
gttattagat aagctatgaa agtcaatcct tttaatcgag aatgtaaata tgtggaatac     60

acaattttaa ccaaagtact atatatgcgt tacaagtaat ttaaatttaa gttcaccgaa    120

gtaaaactaa ctgcaagatt gttacaaaga acaatgcact atttaaatca cacaatggct    180

attgaaaact gtaactgtca gaaatgctgc atgtatctat atgcatcact aagttgcgac    240

ttttaagaaa cttccacagt tctcaactct tctttgtgct tttcacacat tttcacaatt    300

ttccgaaatc tccaaattga aaaaaaaata aaaataaaaa aaggcaggag aagactaagt    360

attcattatt cgctgtttca taaataaaag gataaaaagg ttaaggatac tgattaaaat    420

gtttgtcagg gttaaattga ataaaccagt aaaatggtat aggttctata gtacgttgga    480

ttcacattcc ctaaagttac agagcggctc gaagtttgta aaaatagagg cagtaaataa    540

cttgaggagt agttcatcag cagatttcgt gtccccacca aattccaaat tacaatcttt    600

aatctggcag aaccctttac aaaatgttta tataactaaa aaaccatgga ctccatccac    660

aagagaagcg atggttgaat tcataactca tttacatgag tcatacccg aggtgaacgt    720

cattgttcaa cccgatgtgg cagaagaaat ttcccaggat ttcaaatctc ctttggagaa    780

tgatcccaac cgacctcata tactttatac tggtcctgaa caagatatcg taaacagaac    840

agacttattg gtgacattgg gaggtgatgg gactatttta cacggcgtat caatgttcgg    900

aaatacgcaa gttcctccgg ttttagcatt tgctctgggc actctgggct ttctattacc    960

gtttgatttt aaggagcata aaaaggtctt tcaggaagta atcagctcta gagccaaatg   1020

tttgcataga acacggctag aatgtcattt gaaaaaaaag gatagcaact catctattgt   1080

gacccatgct atgaatgaca tattcttaca taggggtaat tcccctcatc tcactaacct   1140

ggacattttc attgatgggg aatttttgac aagaacgaca gcagatggtg ttgcattggc   1200

cactccaacg ggttccacag catattcatt atcagcaggt ggatctattg tttccccatt   1260

agtccctgct attttaatga caccaatttg tcctcgctct ttgtcattcc gaccactgat   1320

tttgcctcat tcatcccaca ttaggataaa gataggttcc aaattgaacc aaaaaccagt   1380
```

-continued

```
caacagtgtg gtaaaacttt ctgatgatgg tattcctcaa caggatttag atgttggtga   1440

tgaaagttat gttataaatg aggtcggcac tatatacata gatggtactc agcttccgac   1500

gacaagaaaa actgaaaatg actttaataa ttcaaaaaag cctaaaaggt cagggattta   1560

ttgtgtcgcc aagaccgaga atgactggat tagaggaatc aatgaacttt gtaggattca   1620

ttctagcttt aggctgacca agagacagac tgataatgat taaacgctct gaatgcaaag   1680

attcaatgag attctctaag aattctattg ataagattta aaggtacc                1728
```